(12) United States Patent
Breining et al.

(10) Patent No.: US 7,402,592 B2
(45) Date of Patent: Jul. 22, 2008

(54) PHARMACEUTICAL COMPOSITIONS AND METHODS FOR RELIEVING PAIN AND TREATING CENTRAL NERVOUS SYSTEM DISORDERS

(75) Inventors: Scott R. Breining, Winston-Salem, NC (US); Balwinder S. Bhatti, Winston-Salem, NC (US); Gregory D. Hawkins, Charlotte, NC (US); Lan Miao, Advance, NC (US); Anatoly Mazurov, Greensboro, NC (US); Teresa Y. Phillips, Greensboro, NC (US); Craig H. Miller, Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 500 days.

(21) Appl. No.: 10/711,969

(22) Filed: Oct. 15, 2004

(65) Prior Publication Data

US 2005/0282823 A1   Dec. 22, 2005

Related U.S. Application Data

(60) Provisional application No. 60/511,697, filed on Oct. 15, 2003.

(51) Int. Cl.
*A61K 31/439*   (2006.01)
*C07D 221/22*   (2006.01)
(52) U.S. Cl. .................... 514/299; 546/112
(58) Field of Classification Search ............... 514/305, 514/299; 546/125, 133, 112
See application file for complete search history.

(56) References Cited

U.S. PATENT DOCUMENTS

| | | | |
|---|---|---|---|
| 4,922,901 A | 5/1990 | Brooks | |
| 4,965,074 A | 10/1990 | Leeson | |
| 5,187,166 A | 2/1993 | Kikuchi | |
| 5,210,076 A | 5/1993 | Berliner | |
| 5,212,188 A | 5/1993 | Caldwell | |
| 5,227,391 A | 7/1993 | Caldwell | |
| 5,242,935 A | 9/1993 | Lippiello | |
| 5,583,140 A | 12/1996 | Bencherif | |
| 5,597,919 A | 1/1997 | Dull | |
| 5,604,231 A | 2/1997 | Smith | |
| 5,616,716 A | 4/1997 | Dull | |
| 5,663,356 A | 9/1997 | Ruecroft | |
| 5,672,601 A | 9/1997 | Cignarella | |
| 5,852,041 A | 12/1998 | Cosford | |
| 5,853,696 A | 12/1998 | Elmaleh | |
| 5,861,423 A | 1/1999 | Caldwell | |
| 5,952,339 A | 9/1999 | Bencherif | |
| 5,969,144 A | 10/1999 | London | |
| 6,310,043 B1 | 10/2001 | Bundle | |
| 6,638,925 B2 | 10/2003 | Czollner | |
| 2001/0056084 A1 | 12/2001 | Allgeier | |
| 2002/0016371 A1 | 2/2002 | Shytle | |

FOREIGN PATENT DOCUMENTS

| | | |
|---|---|---|
| EP | 0 239 309 A2 | 9/1987 |
| EP | 0 297 858 A2 | 1/1989 |
| EP | 0 588 917 B1 | 3/1994 |
| EP | 0 978 280 A1 | 2/2000 |
| GB | 2 295 387 A | 5/1996 |
| WO | WO 94/08992 | 4/1994 |
| WO | WO 96/30372 A1 | 10/1996 |
| WO | WO 96/31475 | 10/1996 |
| WO | WO 96/36637 | 11/1996 |
| WO | WO 97/30998 | 8/1997 |
| WO | WO 98/25619 | 6/1998 |
| WO | WO 99/03859 | 1/1999 |
| WO | WO 99/21834 | 5/1999 |
| WO | WO 99/62505 | 12/1999 |
| WO | WO 99/65876 | 12/1999 |
| WO | WO 00/23424 | 4/2000 |
| WO | WO 01/36417 A1 | 5/2001 |
| WO | WO 02/15662 A2 | 2/2002 |
| WO | WO 02/16355 A2 | 2/2002 |
| WO | WO 02/16356 A2 | 2/2002 |
| WO | WO 02/16357 A2 | 2/2002 |

(Continued)

OTHER PUBLICATIONS

Yuen, Darren; Richardson, Robert M. A.; Fenton, Stanley S. A.; McGrath-Chong, Margaret E.; Chan, Christopher T. "Quotidian Nocturnal Hemodialysis Improves Cytokine Profile and Enhances Erythropoietin Responsiveness." ASAIO Journal. 51(3):236-241, May/Jun. 2005. Abstract only.*

(Continued)

*Primary Examiner*—Rita Desai
*Assistant Examiner*—David K O'Dell
(74) *Attorney, Agent, or Firm*—Womble Carlyle Sandridge & Rice, PLLC

(57) ABSTRACT

Patients susceptible to or suffering from disorders, such as central nervous system disorders, which are characterized by an alteration in normal neurotransmitter release, such as dopamine release (e.g., Parkinsonism, Parkinson's Disease, Tourette's Syndrome, attention deficient disorder, or schizophrenia), are treated by administering a compound of Formulas 1 or 2, as described herein. The compounds of Formulas 1 and 2 are also useful for treating pain, and treating drug addiction, nicotine addiction, and/or obesity. The compounds can exist as individual stereoisomers, racemic mixtures, diastereomers and the like.

17 Claims, No Drawings

FOREIGN PATENT DOCUMENTS

| WO | WO 02/16358 A2 | 2/2002 |
| --- | --- | --- |
| WO | WO 02/17358 A2 | 2/2002 |
| WO | WO 2004/016604 A2 | 2/2004 |

OTHER PUBLICATIONS

Birch, et. al. "Reduction by Dissolving Metals" Australian Journal of Chemistry 1954, 7, 256-260.*
Dorwald F. A. Side Reactions in Organic Synthesis, 2005, Wiley: VCH, Weinheim p. IX of Preface, p. 41, 279-308.*
("Lithium Aluminum Hydride" Paquette, L. in Encyclopedia of Reagents for Organic Synthesis Online Posting Date: Oct. 15, 2004 2004 John Wiley & Sons, Ltd. "http://www.mrw.interscience.wiley.com/eros/articles/rl036/frame.html".*
Amundsen, L.H. et. al. J. Am. Chem. Soc. 1951, 73, 242-244.*
F. Ivy Carroll "Epibatidine structure-activity relationships" Bioorganic & Medicinal Chemistry Letters 2004 14, 1889-1896.*
Huabei Zhang, Hua Li, Qinqin M. "QSAR study of a large set of 3-pyridyl ethers as ligands of the a4b2 nicotinic acetylcholine receptor." Journal of Molecular Graphics and Modelling 2007, 26, 226-235.*
Desphande et. al. "Nicotine inhibits apoptosis induced by chemotherapeutic drugs by up-regulating XIAP and survivin" PNAS 2006, 6332-6337.*
Wong et. al. "Nicotine Promotes Colon Tumor Growth and Angiogenesis through b-Adrenergic Activation" Toxicological Sciences 2007, 97, 279-287.*
Borisy et. al. "Systematic discovery of multicomponent therapeutics" PNAS 2003, 100, 7977-7982.*
Grant R. Zimmermann "Multi-target therapeutics: when the whole is greater than the sum of the parts." Drug Discovery Today 2007, 12, 34-42.*
Dorwald F. A. Side Reactions in Organic Synthesis, 2005, Wiley: VCH, Weinheim p. IX of Preface p. 1-15.*
Adler, et al., "Normalization by Nicotine of Deficient Auditory Sensory Gating in the Relatives of Schizophrenics," *Biol. Psychiatry*, 32(7): 607-616 (1992).
Afify, E.A., "Turnover of μ-opiod receptors in neuroblastoma cells," *Molecular Brain Research*, 106: 83-87 (2002).
Arneric, S., et al., "Preclinical Pharmacology of ABT-418: A Prototypical Cholinergic Channel Activator for the Potential Treatment of Alzheimer's Disease," *CNS Drug Rev.* 1(1): 1-26 (1995).
Arneric, S., et al., "Cholinergic channel modulators as a novel therapeutic strategy for Alzheimer's disease," *Exp. Opin. Invest. Drugs*, 5(1): 79-100 (1996).
Asaoka, M., et al., "A New Synthetic Route to Functionalized 2-Azabicyclo[2.2.2]Octane," *Heterocycles*, 38(11): 2455-2462 (1994).
Bannon, A.W., et al., "ABT-594[(R)-5-(2-azetidinylmethoxy)-2-chloropyridine]: A Novel, Orally Effective Antinociceptive Agent Acting via Neuronal Nicotinic Acetylcholine Receptors: II. In Vivo Characterization," *J. Pharmaco.l Exp. Ther.*, 285(2): 787-794 (1998).
Bannon, A.W., et al., "Broad-Spectrum, Non-Opioid Analgesic Activity by Selective Modulation of Neuronal Nicotinic Acetylcholine Receptors," *Science*, 279: 77-81 (1998).
Baron, J.A., "Cigarette smoking and Parkinson's Disease," *Neurology*, 36:1490-1496 (1986).
Bencherif, M., and J. D. Schmitt, "Targeting Neuronal Nicotinic Receptors: a Path to New Therapies," *Current Drug Targets*, 1(4): 349-357 (2002).
Bencherif, M., et al., "RJR-2403: A Nicotinic Agonist with CNS Selectivity I: In Vitro Characterization," *J. Pharmacol. Exper. Therapeutics*, 279(3): 1413-1421 (1996).
Bencherif M. and R.J. Lukas, "Differential Regulation of Nicotinic Acetylcholine Receptor Expression by Human TE671/RD Cells Following Second Messenger Modulation and Sodium Butyrate Treatments," *Mol Cell Neurosci.*,2(1): 52-65 (1991).
Bencherif, M., and R.J. Lukas, "Ligand Binding and Functional Characterization of Muscarinic Acetylcholine Receptors on the TE671/RD Human Cell Line," *J. Pharmacol. Exp. Ther.*, 257(3): 946-953 (1991).

Bennett, G.J., and Y.-K. Xie, "A peripheral mononeuropathy in rat that produced disorders of pain sensation like those seen in man," *Pain*, 33: 87-107 (1988).
Boger, D.L., et al., "Synthetic Analgesics: Preparation of Racemic 6,7-Benzomorphans," *Tet. Lett.*, 23(44): 4559-4562 (1982).
Bok, Th. R., and W.N. Speckamp, "Synthesis and Conformational Analysis of EXO-and ENDO-7-Substituted-3-Azabicyclo[3.3.1.]Nonanes," *Tetrahedron*, 35: 267-272 (1979).
Bok, Th. R. and Speckamp, W.N., "3-Azanoradamantanes," *Heterocycles*, 12(3): 343-347 (1979).
Brioni, J.D., et al., "The Pharmacology of (−)-Nicotine and Novel Cholinergic Channel Modulators," *Adv. Pharmacol.*, 37: 153-214 (1997).
Calderon-Gonzalez, R., and R.F. Calderon-Sepulveda, "Tourette Syndrome Current Concepts," *Intern. Pediat.*, 8(2): 176-188 (1993).
Cheng, Yung-Chi, and W.H. Prusoff, "Relationship Between the Inhibition Constant ($K_1$) and the Concentration of Inhibitor which Causes 50 Per Cent inhibition ($I_{50}$) of an Enzymatic Reaction," *Biochem. Pharmacol.*, 22(23): 3099-3108 (1973).
Chiari, A., et al., "Sex Differences in Cholinergic Analgesia I: A Supplemental Nicotinic Mechanism in Normal Females," *Anesthesiology*, 91(5): 1447-1454 (1999).
Clarke, P.B.S., et al., "Electrophysiological actions of nicotine on substantia nigra single units," *Br. J. Pharm.*, 85(4): 827-835 (1985).
D'amour, F.E., and D.L. Smith, "A Method for Determining Loss of Pain Sensation," *J. Pharmacol. Exp. Ther.*, 72: 74-79 (1941).
Damaj, M.I., et al., "The antinociceptive effects of α7 nicotinic agonists in an acute pain model," *Neuropharmacology*, 39: 2785-2791 (2000).
Damaj, M.I., et al., "Antinociceptive and Pharmacological Effects of Metanicotine, a Selective Nicotinic Agonist," *J. Pharmacol. Exp. Ther.* 291(1): 390-398 (1999).
Davies, A.R.L., et al., "Characterisation of the binding of [$^3$H]methyllycaconitine: a new radioligand for labeling α7-type neuronal nicotinic acetylcholine receptors," *Neuropharmacol.*, 38: 679-690 (1999).
Decina, P., et al., "Cigarette Smoking and Neuroleptic-Induced Parkinsonism," *Biol. Psychiatry*, 28(6): 502-508 (1990).
Devor, E.J., and Keith E. Isenberg, "Nicotine and Tourette's Syndrome," *The Lancet* 2(8670): 1046 (1989).
Dolle, F., et al., "Synthesis and preliminary evaluation of a carbon-11-labelled agonist of the α-7 nicotinic acetylcholine receptor," *J. Labelled Comp. Radiopharm.*, 44: 785-795 (2001).
Dwoskin, L.P., et al., "Recent developments in neuronal nicotinic acetylcholine receptor antagonists," *Exp. Opin. Ther. Patents*, 10(10): 1561-1581 (2000).
Faraone, S.V., et al., "An Exploratory Study of ADHD among Second-Degree Relatives of ADHD Children," *Biol. Psychiatry*, 35(6): 398-402 (1994).
Freeman, P.K., et al., "A Method for the Addition of the Elements of Ketene to Some Selected Dienes in Diels-Alder Fashion," *J. Org. Chem.*, 33(6): 2211-2214 (1968).
Freedman, R., et al., "Evidence in Postmortem Brain Tissue for Decreased Numbers of Hippocampal Nicotinic Receptors in Schizophrenia," *Biol. Psychiatry*, 38(1): 22-33 (1995).
Freedman, R., et al., "Linkage of a neurophysiological deficit in schizophrenia to a chromosome 15 locus," *Proc. Natl. Acad. Sci.*, 94: 587-592 (1997).
Furstoss, R., et al., "Synthesis of N-Methyl-6-azabicyclo[3,2.1]octan-3-one, an Alkaloid Sub-unit," *J. Chem. Soc. Chem. Comm.*, 6: 384-385 (1970).
Gensler, W.J., et al., "Synthesis of 6-Benzyl-3 oxo-6-azabicyclo[3.2.1]octane," *J. Org. Chem.*, 33(7): 2968-2971 (1968).
Giacobini, E., "Cholinergic Receptors in Human Brain: Effects of Aging and Alzheimer Disease," *J. Neurosci. Res.*, 27(4): 548-560 (1990).
Glassman, A. H., "Cigarette Smoking: Implications for Psychiatric Illness," *Amer. J. Psychiatry*, 150(4): 546-553 (1993).
Grady, S., et al., "Characterization of nicotinic receptor mediated [3H]dopamine release from synaptosomes prepared from mouse striatum," *J. Neurochem.* 59: 848-856 (1992).

Grossman, M.L., et al., "Afferent and Efferent Connections of the Rat Tail Flick Reflex (A Model Used to Analyze Pain Control Mechanisms," *J. Comp. Neurol.*, 206: 9-16 (1982).

Hall, G.H., and D.M. Turner, "Effects of Nicotine on the Release of $^3$H-Noradrenaline from the Hypothalamus," *Biochemical Pharmacology*, 21: 1829-1838 (1972).

Hamon, M., "Neuropharmacology of anxiety: perspectives and prospects," *TiPS*, 15: 36-39 (1994).

Hansch, C., et al., "A Survey of Hammett Substituent Constants and Resonance and Field Parameters," *Chem. Rev.*, 91(2): 165-195 (1991).

Harsing, L.G., Jr., et al., "Dopamine Efflux from Striatum After Chronic Nicotine: Evidence for Autoreceptor Desensitization," *J. Neurochem.*, 59(1): 48-54 (1992).

Hechtman, L., "Genetic and Neurobiological Aspects of Attention Deficit Hyperactive Disorder: A Review" *J. Psychiatry Neurosci,.* 19(3): 193-201 (1994).

Heeschen, C., et al., "A novel angiogenic pathway mediated by non-neuronal nicotinic acetylcholine receptors," *J. Clin. Invest.*, 110(4): 527-536 (2002).

Hery, F., et al., "Control of the Release of Newly Synthetized $^3$H-5-Hydroxytryptamine by Nicotinic and Muscarinic Receptors in Rat Hypothalamic Slices," *Naunyn-Schmiedeberg's Arch. Pharmacol.*, 296: 91-97 (1977).

Hodges, H., et al., "Nicotine as a Tool to Characterise the Role of the Forebrain Cholinergic Projection System in Cognition," *Bio. of Nic.*, Edit. by Lippiello, et al., 157-182 (1992).

Holladay, M.W., et al., "Neuronal Nicotinic Acetylcholine Receptors as Targets for Drug Discovery," *J. Med. Chem.*, 40(26): 4169-4194 (1997).

Hoyer, D. and H.W.G.M. Boddeke, "Partial agonists, full agonists, antagonists: dilemmas of definition," *TiPS Reviews*, 14: 270-275 (1993).

Huffman, J.W., et al., "The Synthesis of Desethylibogamine," *J. Org. Chem.* 32: 697-700 (1967).

Ishiyama, T., et al., "Palladium (0)-Catalyzed Cross-Coupling Reaction of Alkoxydiboron with Haloarenes: A Direct Procedure for Arylboronic Esters," *J. Org. Chem.*, 60:7508-7510 (1995).

Jarvik, M.E., "Beneficial effects of nicotine," *Brit. J. of Addic.*, 86(5): 571-575 (1991).

Jeyarasasingam, G., et al., "Stimulation of Non-α7 Nicotinic Receptors Partially Protects Dopaminergic Neurons from 1-Methyl-4 Phenylpyridinium-Induced Toxicity in Culture," *Neuroscience*, 109(2): 275-285 (2002).

Johnson, R.A., et al., "The Microbiologicla Oxygenation of Some Azabicycloalkanes," *J. Org. Chem.* 33(8): 3195-3201 (1968).

Johnson, R.A., et al., "Sterochemistry of Microbiological Hydroxylation. III. Hydroxylation of 3-Benzoyl-3-azabicyclo[3.3.1]nonane with Rhizopus arrhizus. Novel Chromic Acid Oxidations of Substrate and Product," *J. Org. Chem.*, 34(12): 3834-3837 (1969).

Jones, A.W.R., and J. Steven Richardson, "Alzheimer's Disease: Clinical and Pathological Characteristics," *Intern. J. Neurosci.* 50(3-4): 147-168 (1990).

Krow, G.R., et al., "A Sterospecific Route to 6-Substituted," *Syn. Comm.*, 13(7): 575-579 (1983).

Kuehne, M.E., and D.A. Horne, "Photochemical Cyclization of Olefinic N-Chloromides," *J. Org. Chem.*, 40(9): 1287-1292 (1975).

Kwak, Y-S., and J.D. Winkler, "Synthesis of 6-Azabicyclo[3,2,1]octan-3-ones via Vinylogous Imide Photochemistry: An Approach to the Synthesis of the Hetisine Alkaloids," *J. Am. Chem. Soc.*, 123: 7429-7430 (2001).

Lavand'homme, P., and J.C. Eisenach, "Sex Differences in Cholinergic Analgesia II: Differing Mechanisms in Two Models of Allodyina," *Anesthesiology*, 91(5): 1455-1461 (1999).

Le Drian, C. and A.E. Greene, et al., "Efficient Stereocontrolled Total Syntheses of Racemic and Natural Brefeldin-A," *J. Am. Chem. Soc.*, 104: 5473-5483 (1982).

Levin, E.D., and A.H. Rezvani, "Nicotinic Treatment for Cognitive Dysfunction," *Current Drug Targets: CNS and Neurological Disorders*, 1(4): 423-431 (2002).

Levin, L.D., et al., "Nicotine effects on adults with attention-deficit/hyperactivity disorder," *Psychopharmacology*, 123: 55-63 (1996).

Lepifre, F., et al., "Palladium-catalysed coupling of vinyl phosphates with aryl or heteroaryl boronic acids. Application to the synthesis of substituted nitrogen containing heterocyles," *Tetrahedron Lett.*, 40(35): 6373-6376 (1999).

Leonard, S., et al., "Nicotinic Receptor Function in Schizophrenia," *Schizophrenia Bulletin*, 22(3): 431-445 (1996).

Li, W., et al., "An Improved Protocol for the Preparation of 3-Pyridyl- and Some Arylboronic Acids," *J. Org. Chem.* 67(15): 5394-5397 (2002).

Lin, X., et al., "A mild new procedure of production, cyclization and trapping of amidyl radicals: application to a formal total synthesis of peduncularine," *Tetrahedron Letters*, 41: 2333-2337 (2000).

Lippiello, P.M., et al., "RJR-2403: A Nicotinic Agonist with CNS Selectivity II. In Vivo Characterization," *J. Pharmacol. Exp. Ther.* 279(3): 1422-1429 (1996).

Lieberman, Jeffrey A., and Amy R. Koreen, "Neurochemistry and Neuroendocrinology of Schizophrenia: A Selective Review," *Schizophr. Bull.*, 19(2): 371-429 (1993).

Lowry, O.H., et al., "Protein Measurement with the Folin Phenol Reagent," *J. Biol. Chem.*, 193: 265-275 (1951).

Lukas, R.J., and M.J. Cullen, "An Isotopic Rubidium Ion Efflux Assay for the Functional Characterization of Nicotinic Acetylcholine Receptors on Clonal Cell Lines," *Anal. Biochem.* 175(1): 212-218 (1988).

Lukas, R.J., et al., "Characterization of Nicotinic Acetylcholine Receptors Expressed by Cells of the SH-SY5Y Human Neuroblastoma Clonal Line," *Molec Cellular Neurosci* 4(1): 1-12 (1993).

Luther, M.A., et al., "A Muscle Acetylcholine Receptor is Expressed in the Human Cerebellar Medulloblastoma Cell Line TE671," *J. Neurosci.*, 9(3): 1082-1096 (1989).

Macor, J.E., et al., "The 5-HT$_3$ Antagonist Tropisetron (ICS 205-930) is a Potent and Selective α7 Nicotinic Receptor Partial Agonist," *Bioorg. Med. Chem. Lett.*, 11: 319-321 (2001).

Mackiewicz, P., et al., "Peroxide-Initiated Cyclizations of Olefinic N-Chloro Amides. Electronic Configuration of Amido Radicals," *J. Org. Chem.*, 43(19): 3746-3750 (1978).

Malone, M.A., et al., "Hemispheric Processing and Methylphenidate Effects in Attention-Deficit Hyperactivity Disorder," *J. Child Neurol.*, 9(2): 181-189 (1994).

Marks, M.J., et al., "Nicotinic Binding Sites in Rat and Mouse Brain: Comparison of Acetylcholine, Nicotine, and α-Bungarotoxin," *Mol. Pharmacol.*, 30(5): 427-436 (1986).

Marks, M.J., et al., "Effects of Chronic Nicotine Infusion on Tolerance Development and Nicotinic Receptors," *J. Pharmacol. Exp. Ther.*, 226(3): 817-825 (1983).

Mazzocchi, P.H., et al., "Synthesis of Diphenyl Ether Models of Thyroid Hormones. Diphenyl Ethers Linked to the 3-Oxo-2-azabicyclo[2.2.1]heptane Ring System as Substrates for Conformational Analysis," *J. Org. Chem.*, 46: 4530-4536 (1981).

McConville, B.J., et al., "Nicotine Potentiation of Haloperidol in Reducing Tic Frequency in Tourette's Disorder," *Am. J. Psychiatry*, 148(6): 793-794 (1991).

McConville, B.J., et al., "The Effects of Nicotine Plus Haloperidol Compared to Nicotine Only and Placebo Nicotine Only in Reducing Tic Severity and Frequency-in Tourette's Disorder," *Biol. Psychiatry*, 31(8): 832-840 (1992).

Merriam, A.E., et al., "Schizophrenia as a Neurobehavioral Disorder," *Psychiatr. Annals*, 23(4): 171-178 (1993).

Murata, M., et al., "Palladium-Catalyzed Borylation of Aryl Halides or Triflates with Dialkoxyborane: A Novel and Facile Synthetic Route to Arylboronates," *J. Org. Chem.*, 65: 164-168 (2000).

Nan, Y., and Zhen Yang, "Nickel-Catalyzed Cross-Couplings of Cyclohexenyl Phosphate and Arylboronic Acids," *Tetrahedron Lett.*, 40(17): 3321-3324 (1999).

Newhouse, P.A., and John R. Hughes, "The role of nicotine and nicotinic mechanisms in neuropsychiatric disease," *Brit. J. Addic,.* 86: 521-525 (1991).

Oh-e, T., et al., "Palladium—Catalyzed Cross-Coupling Reaction of Organoboron Compounds with Organic Triflates," *J. Org. Chem.*, 58: 2201-2208 (1993).

O'Neill, M.J., et al., "The Role of Neuronal Nicotinic Acetylcholine Receptors in Acute and Chronic Neurodegeneration," *Current Drug Targets: CNS and Neurological Disorders*, 1(4): 399-411 (2002).

Onaivi, E.S., et al., "Chronic Nicotine Reverses Age-Associated Increases in Tail-Flick Latency and Anxiety in Rats," *Life Sciences*, 54(3): 193-202 (1993).

Oswald, R.E., et al., "Characterization of nicotinic acetylcholine receptor channels of the TE671 human medulloblastoma clonal line," *Neurosci. Lett.*, 96: 207-212 (1989).

Perry, E.K., "The Cholinergic Hypothesis—Ten Years On," *Br. Med. Bull.*, 42(1): 63-69 (1986).

Pitner, J.B., et al., "Synthesis and Stereoselective Reduction of (±), (+)-and (−)-6-Substituted-6-azabicyclo[3.2.1]octan-3-one," *J. Chem. Soc. Perkin Trans. I*, 1375-1381 (1991).

Pomerleau, O.F., et al., "The Effects of Cigarette Smoking on Pain and Anxiety," *Addictive Behaviors*, 9: 265-271 (1984).

Pullan, R.D., et al. "Transdermal Nicotine for Active *Ulcerative colitis,*" *New England J. Med.*, 330(12): 811-815 (1994).

Quirante, J., et al., "Synthesis of enantiopure 2-azabicyclo[3.3.1]nonanes by a radical ring closure," *Tetrahedron: Asymmetry*, 10(12): 2399-2410 (1999).

Rapier, C., et al., "Nicotinic Modulation of [$^3$H]Dopamine Release from Striatal Synaptosomes: Pharmacological Characterisation," *J. Neurochem.*, 54(3): 937-45 (1990).

Rapier, C., et al., "Stereoselective Nicotine-Induced Release of Dopamine from Striatal Synaptosomes: Concentration Dependence and Repetitive Stimulation," *J. Neurochem.*, 50(4): 1123-1130 (1988).

Rinne, J.O., et al., "A postmortem study of brain nicotinic receptors in Parkinson's and Alzheimer's disease," *Brain Res.*, 547(1): 167-170 (1991).

Romano, C., and Avram Goldstein, "Stereospecific Nicotine Receptors on Rat Brain Membranes," *Science*, 210(7): 647-650 (1980).

Rowell, P.P. and Donald L. Winkler, "Nicotinic Stimulation of [$^3$H] Acetylcholine Release from Mouse Cerebral Cortical Synaptosomes," *J. Neurochem.*, 43(6): 1593-1598 (1984).

Rowell, P.P., "Current Concepts on the Effects of Nicotine on Neurotransmitter Release in the Central Nervous System," *Adv. Behav. Biol.*, 31: 191-208 (1987).

Sahakian, B., et al., "The Effects of Nicotine on Attention, Information Processing, and Short-Term Memory in Patients with Dementia of the Alzheimer Type," *Br. J. Psych.*, 154: 797-800 (1989).

Sanberg, P.R., et al., "Nicotine Potentiation of Haloperidol-Induced Catalepsy: Striatal Mechanisms," *Pharmacol. Biochem. & Behavior*, 46: 303-307 (1993).

Sanberg, P.R., and Archie A. Silver, "Beneficial Effects of Nicotine in Tourette's Syndrome," *Proceedings from Intl. Symp. Nic.*, S39 (1994).

Sandor, M.T., et al. "Effect of nicotine on dopaminergic-cholinergic interaction in the striatum," *Brain Res.*, 567: 313:316 (1991).

Sato, T., et al., "Regioselective Synthesis of Bridged Azabicyclic Compounds Using Radical Translocation/Cyclization Reactions of 4-Alkynyl-1-(*o*-Iodobenzoyl) Piperidines," *Heterocycles*, 54(2): 747-755 (2001).

Sjak-Shie, N.N., and E.M. Meyer, "Effects of chronic nicotine and pilocarpine administration on neocortocal neuronal density and [$^3$H]GABA uptake in nucleus basalis lesioned rats," *Brain Res.*, 624: 295-298 (1993).

Schmitt, J.D., and Merouane Bencherif, "Chapter 5. Targeting Nicotinic Acetylcholine Receptors: Advances in Molecular Design and Therapies," *Ann. Rep. Med. Chem.*, 35: 41-51 (2000).

Sherwood, N., "Effects of Nicotine on Human Psychomotor Performance," *Human Psychopharm.*, 8: 155-184 (1993).

Sitaram, N., et al., "Human Serial Learning: Enhancement with Arecholine and Choline and Impairment with Scopolamine," *Science*, 201: 274-276 (1978).

Soliakov, L., and S. Wonnacott, "Voltage-sensitive $Ca^{2+}$ channels involved in nicotinic receptor-mediated [$^3$H]dopamine release from rat striatal synaptosomes," *J. Neurochem.*, 67: 163-170 (1996).

Smith, C.J., and E. Giacobini, "Nicotine, Parkinson's and Alzheimer's Disease," *Rev. Neurosci.*, 3(1): 25-43 (1992).

Stevens, K.E., et al., "Selective $\alpha_{-7}$-nicotinic agonists normalize inhibition of auditory response in DBA mice," *Psychopharm.*, 136: 320-327 (1998).

Stratton, M.R., et al., "Characterization of the human cell line TE671," *Carcinogenesis*, 10(5): 899-905 (1989).

Toth, E., et al., "Effect of Nicotine of Extracellular Levels of Neurotransmitters Assessed by Microdialysis in Various Brain Regions: Role of Glutamic Acid," *Neurochem. Res.*, 17(3): 265-270 (1992).

Tracey, K. J., "The Inflammatory Reflex," *Nature*, 420:853-859 (2002).

Tripathi, H.L., et al., "Nicotine-Induced Antinociception of Rats and Mice: Correlation with Nicotine Brain Levels," *J. Pharmacol. Exp. Ther.*, 221(1): 91-96 (1982).

Trost, B.M., and J.P.Genêt, "Palladium Catalyzed Cyclizations to Alkaloid Skeletons. Facile Synthesis of Desethylibogamine," *J. Am. Chem. Soc.*, 98(26): 8516-8517 (1976).

Tufariello, J.J., et al., "The use of Nitrones in the Synthesis of Anatoxin-a, very fast death factor," *Tetrahedron*, 41(7): 3447-3453 (1985).

Villemagne, V.V., et al., "Nicotine and Related Compounds as PET and SPECT Ligands," *Neuronal Nicotinic Receptors Pharmacology and Therapeutic Opportunities*, 235-250 (1999).

Vinson, D.C., "Therapy for Attention-Deficit Hyperactivity Disorder," *Arch. Fam. Med.*, 3(5): 445-451 (1994).

Vizi, E.S., "Acetylcholine release from guinea-pig ileum by parasympathetic ganglion stimulants and gastrin-like polypeptides," *Br. J. Pharmac.*, 47: 765-777 (1973).

Wagner, B., et al., "Does Smoking Reduce the Risk of Neuroleptic Parkinsonoids?," *Pharmacopsychiat,*. 21: 302-303 (1988).

Wang, H., et al., "Nicotinic acetylcholine receptor α7 subunit is an essential regulator of inflammation," *Nature*, 421: 384-388 (2003).

Warburton, D.M., and J.M. Rusted, "Cholinergic Control of Cognitive Resources," *Neuropsychobiology*, 28: 43-46 (1993).

Whiting, P. J., et al., "Functional acetylcholine receptor in PC12 cells reacts with a monoclonal antibody to brain nicotinic receptors," *Nature*, 327: 515-518 (1987).

Whiting, P.J., et al., "Expression of nicotinic acetylcholine receptor subtypes in brain and retina," *Mol Brain Res.*, 10(1): 61-70 (1991).

Williams, M., et al., "Neuronal Nicotinic Acetylcholine Receptors," *Drug News Perspec.*, 7(4): 205-223 (1994).

Xiao, H-S., et al., "Identification of gene expression profile of dorsal root ganglion in the rat peripheral axotomy model of neuropathic pain," *Proc. Nat. Acad. Sci.*, 99(12): 8360-8365 (2002).

\* cited by examiner

PHARMACEUTICAL COMPOSITIONS AND METHODS FOR RELIEVING PAIN AND TREATING CENTRAL NERVOUS SYSTEM DISORDERS

FIELD OF THE INVENTION

The present invention relates to pharmaceutical compositions, particularly pharmaceutical compositions incorporating compounds that are capable of affecting nicotinic acetylcholinergic receptors (nAChRs). The present invention also relates to methods for treating a wide variety of conditions and disorders, particularly conditions and disorders associated with dysfunction of the central and autonomic nervous systems, and the treatment of addiction, including smoking addiction and addiction to narcotics and other drugs, and obesity.

BACKGROUND OF THE INVENTION

Nicotine has been proposed to have a number of pharmacological effects. See, for example, Pullan et al., *N. Engl. J. Med.* 330:811 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem. Res.* 17:265 (1992). Confirmatory reports and additional recent studies have included the modulation, in the central nervous system (CNS), of glutamate, nitric oxide, GABA, takykinins, cytokines and peptides (reviewed in Brioni et al., *Adv. Pharmacol.* 37:153 (1997)). In addition, nicotine reportedly potentiates the pharmacological behavior of certain pharmaceutical compositions used for the treatment of certain CNS disorders. See Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, for example, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *J. Pharmacol. Exp. Ther.* 221:91 (1982) and Hamon, *Trends in Pharmacol. Res.* 15:36.

Various nicotinic compounds have been reported as being useful for treating a wide variety of conditions and disorders. See, for example, Williams et al., *Drug News & Perspectives* 7(4):205 (1994); Arneric et al., *CNS Drug Rev.* 1(1):1 (1995); Arneric et al., *Exp. Opin. Invest. Drugs* 5(1):79 (1996); Bencherif et al., *J. Pharmacol. Exp. Ther.* 279:1413 (1996); Lippiello et al., *J. Pharmacol Exp. Ther.* 279:1422 (1996); Damaj et al., *J. Pharmacol Exp. Ther.* 291:390 (1999); Chiari et al., *Anesthesiology* 91:1447 (1999); Lavand'homme and Eisenbach, *Anesthesiology* 91:1455 (1999); Holladay et al., *J. Med. Chem.* 40(28): 4169 (1997); Bannon et al., *Science* 279:77 (1998); PCT WO 94/08992, PCT WO 96/31475, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al. Nicotinic compounds are particularly useful for treating a wide variety of CNS disorders. Indeed, a wide variety of nicotinic compounds have been reported to have therapeutic properties. See, for example, Bencherif and Schmitt, *Current Drug Targets: CNS and Neurological Disorders* 1(4): 349 (2002); Levin and Rezvani, *Current Drug Targets: CNS and Neurological Disorders* 1(4): 423 (2002); O'Neill et al., *Current Drug Targets: CNS and Neurological Disorders* 1(4): 399 (2002); U.S. Pat. No. 5,1871,166 to Kikuchi et al., U.S. Pat. No. 5,672,601 to Cignarella, PCT WO 99/21834 and PCT WO 97/40049, UK Patent Application GB 2295387 and European Patent Application 297,858.

Pain can be classified in various ways and can be characterized by a variety of geneses and etiologies (e.g., inflammatory pain, neuropathic pain, chronic pain). Current pain therapy is dominated by two classes of drugs, the non-steroidal anti-inflammatory drugs (NSAIDs) and the opioids, both of which have significant therapeutic liabilities. Various compounds which target nAChRs have been shown to be effective in treating one or more kinds of pain in animal models. See for instance, Damaj et al., *J. Pharmacol. Exp. Ther.* 291:390 (1999); Damaj et al., *Neuropharmacology* 39:2785-2791 (2000); Chiari et al., *Anesthesiology* 91:1447 (1999); Lavand'homme and Eisenbach, *Anesthesiology* 91:1455 (1999); Holladay et al., *J. Med. Chem.* 40(28): 4169 (1997); Bannon et al., *Science* 279:77 (1998); and Bannon et al., *J Pharmacol Exp Ther.* 285:787-794 (1998). Depending on the etiology of the pain, both the (4(2 and the (7 nAChR subtypes (which are CNS nAChR subtypes) have been identified as targets for analgesia. It would be beneficial to provide, with a single pharmaceutical agent, relief from multiple kinds of pain. It would also be beneficial to provide such relief without the gastrointestinal liabilities of the NSAIDs or the abuse potential of the opioids.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin. Relatively common CNS disorders include presenile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, Lewy body dementia, progressive supranuclear palsy, Huntington's chorea, tardive dyskinesia, hyperkinesia, mania, attention deficit disorder, anxiety, dyslexia, schizophrenia, depression, obsessive-compulsive disorders, and Tourette's syndrome.

Senile dementia of the Alzheimer's type (SDAT) is a debilitating neurodegenerative disease, mainly afflicting the elderly, characterized by a progressive intellectual and personality decline, as well as a loss of memory, perception, reasoning, orientation, and judgment. One feature of the disease is an observed decline in the function of cholinergic systems, and specifically, a severe depletion of cholinergic neurons (i.e., neurons that release acetylcholine, which is believed to be a neurotransmitter involved in learning and memory mechanisms). See, for example, Jones et al., *Intern. J. Neurosci.* 50:147 (1990); Perry, *Br. Med. Bull.* 42:63 (1986); and Sitaram et al., *Science* 201:274 (1978). It has been observed that nicotinic acetylcholine receptors, which bind nicotine and other nicotinic agonists with high affinity, are depleted during the progression of SDAT. See Giacobini, *J. Neurosci. Res.* 27:548 (1990) and Baron, *Neurology* 36:1490 (1986). As such, it would seem desirable to provide therapeutic compounds that either directly modulate (for example, that directly activate) nicotinic receptors in place of acetylcholine or act to minimize the loss of those nicotinic receptors.

Certain attempts have been made to treat SDAT. For example, nicotine has been suggested to possess an ability to activate nicotinic cholinergic receptors upon acute administration, and to elicit an increase in the number of such receptors upon chronic administration to animals. See, for example, Rowell, *Adv. Behav. Biol.* 31:191 (1987) and Marks, *J. Pharmacol. Exp. Ther.* 226:817 (1983). It also has been proposed that nicotine can act directly to elicit the release of acetylcholine in brain tissue, to improve cognitive functions, and to enhance attention. See Rowell et al., *J. Neurochem.* 43:1593 (1984); Sherwood, *Human Psychopharm.* 8:155 (1993); Hodges et al., *Bio. of Nic.* Edit. by Lippiello et al., p. 157 (1991); Sahakian et al., *Br J. Psych.* 154:797 (1989); and U.S. Pat. No. 4,965,074 to Leeson and U.S. Pat. No. 5,242,935 to Lippiello et al. Other methods for treating SDAT have been proposed, including U.S. Pat. No. 5,212,188 to Caldwell et al. and U.S. Pat. No. 5,227,391 to Caldwell et al., European Patent Application No. 588,917 and PCT WO 96/30372. Another proposed treatment for SDAT is COGNEX®, which is a capsule containing tacrine hydrochloride, available from Parke-Davis Division of Warner-Lambert Company, which reportedly preserves existing acetylcholine levels in patients treated therewith.

Parkinson's disease (PD) is a debilitating neurodegenerative disease, presently of unknown etiology, characterized by tremors and muscular rigidity. A feature of the disease appears to involve the degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See Rinne et al., *Brain Res.* 54:167 (1991) and Clark et al., *Br. J. Pharm.* 85:827 (1985). It also has been proposed that nicotine can ameliorate the symptoms of PD, as discussed in Smith et al., *Rev. Neurosci.* 3(1):25 (1992).

Certain attempts have been made to treat PD. One proposed treatment for PD is SINEMET CR®, which is a sustained-release tablet containing a mixture of carbidopa and levodopa, available from The DuPont Merck Pharmaceutical Co. Another proposed treatment for PD is ELDEPRYL®, which is a tablet containing selegiline hydrochloride, available from Somerset Pharmaceuticals, Inc. Another proposed treatment for PD is PARLODEL®, which is a tablet containing bromocriptine mesylate, available from Sandoz Pharmaceuticals Corporation. Another method for treating PD and a variety of other neurodegenerative diseases has been proposed in U.S. Pat. No. 5,210,076 to Berliner et al.

Tourette's syndrome (TS) is an autosomal dominant neuropsychiatric disorder characterized by a range of neurological and behavioral symptoms. Typical symptoms include (i) the onset of the disorder before the age of 21 years, (ii) multiple motor and phonic tics although not necessarily concurrently, (iii) variance in the clinical phenomenology of the tics, and (iv) occurrence of quasi-daily tics throughout a period of time exceeding a year. Motor tics generally include eye blinking, head jerking, shoulder shrugging and facial grimacing; while phonic or vocal tics include throat clearing, sniffling, yelping, tongue clicking and uttering words out of context. The pathophysiology of TS presently is unknown, however it is believed that neurotransmission dysfunction is implicated with the disorder. For further discussion, see Calderon-Gonzalez et al., *Intern. Pediat.* 8 (2):176 (1993) and Oxford Textbook of Medicine, Weatherall et al., eds., p. 218 (1987).

It has been proposed that nicotine pharmacology is beneficial in suppressing the symptoms associated with TS. See Devor et al., *The Lancet* 8670: 1046 (1989); Jarvik, *Brit. J. of Addic.* 86: 571 (1991); McConville et al., *Am. J. Psychiatry* 48(6): 793 (1991); Newhouse et al., *Brit. J. Addic.* 86: 521 (1991); McConville et al., *Biol. Psychiatry* 31: 832 (1992); and Sanberg et al., *Proceedings from Intl Symp. Nic.* S39 (1994). It also has been proposed to treat TS using HALDOL®, which is haloperidol available from McNeil Pharmaceutical; CATAPRES®, which is clonidine available from Boehringer Ingelheim Pharmaceuticals, Inc., ORAP®, which is pimozide available from Gate Pharmaceuticals; PROLIXIN®, which is fluphenazine available from Apothecon Division of Bristol-Myers Squibb Co.; and KLONOPIN®, which is clonazepam available from Hoffmann-LaRoche Inc.

Attention deficit disorder (ADD) is a disorder that affects mainly children, although ADD can affect adolescents and adults. See Vinson, *Arch. Fam. Med.* 3(5): 445 (1994); Hechtman, *J. Psychiatry Neurosci* 19(3): 193 (1994); Faraone et al., *Biol. Psychiatry* 35(6): 398 (1994) and Malone et al., *J. Child Neurol.* 9(2): 181 (1994). Subjects suffering from the disorder typically have difficulty concentrating, listening, learning and completing tasks; and are restless, fidgety, impulsive, and easily distracted. Attention deficit disorder with hyperactivity (ADHD) includes the symptoms of ADD as well as a high level of activity (e.g., restlessness and movement). Attempts to treat ADD have involved administration of DEXEDRINE®, which is a sustained release capsule containing dextroamphetamine sulfate, available from SmithKline Beecham Pharmaceuticals; RITALIN®, which is a tablet containing methylphenidate hydrochloride, available from Ciba Pharmaceutical Company; and CYLERT®, which is a tablet containing premoline, available from Abbott Laboratories. In addition, it has been reported that administration of nicotine to an individual improves that individual's selective and sustained attention. See Warburton et al., Cholinergic Control of Cognitive Resources, Europsychobiology, Mendlewicz et al., eds., p. 43 (1993) and Levin et al., *Psychopharmacology* 123: 55 (1996).

Schizophrenia is characterized by psychotic symptoms including delusions, catatonic behavior, and prominent hallucinations, and ultimately results in a profound decline in the psychosocial affect of the subject suffering therefrom. Traditionally, schizophrenia has been treated with KLONOPIN®, which is available as a tablet containing clonezepam, available from Hoffmann-LaRoche Inc.; THORAZINE®, which is available as a tablet containing chlorpromazine, available from SmithKline Beecham Pharmaceuticals; and CLORAZIL®, which is a tablet containing clozapine, available from Sandoz Pharmaceuticals. Such neuroleptics are believed to be effective as a result of interaction with the dopaminergic pathways of the CNS. In addition, a dopaminergic dysfunction possessed by individuals suffering from schizophrenia has been proposed. See Lieberman et al., *Schizophr. Bull.* 0.19:371 (1993) and Glassman, *Amer. J. Psychiatry* 150:546

(1993). Nicotine has been proposed to be effective in modulating neurotransmitter dysfunction associated with schizophrenia. See Merriam et al., *Psychiatr. Annals* 23:171 (1993) and Adler et al., *Biol. Psychiatry* 32:607 (1992). See also Freedman et al., *Proc. Natl. Acad. Sci.* 94:587 (1997).

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology which has a beneficial effect (e.g., upon the functioning of the CNS), but does not provide any significant associated side effects. It would be highly desirable to provide a pharmaceutical composition incorporating a compound that interacts with nicotinic receptors, such as those that have the potential to affect the functioning of the CNS, and methods of treatment using the compounds and compositions. The present invention provides such compounds, compositions, and methods.

There exist subtypes of nAChRs in both the central and peripheral nervous systems, but the distribution of subtypes is heterogeneous. For instance, the subtypes which are predominant in vertebrate brain are (4(2, (7, and (3(2, whereas those which predominate at the autonomic ganglia are (3(4 and those of neuromuscular junction are (1(1(( and (1(1((( (see for instance Dwoskin et al., *Exp. Opin. Ther. Patents* 10:1561 (2000) and Schmitt and Bencherif, *Annual Reports in Med. Chem.* 35: 41 (2000)). A limitation of some nicotinic compounds is that they elicit various undesirable pharmacological effects because of their interaction with nAChRs in peripheral tissues (for example, by stimulating muscle and ganglionic nAChR subtypes). It would be desirable to have compounds, compositions and methods for preventing and/or treating various conditions or disorders (e.g., CNS disorders), including alleviating the symptoms of these disorders, where the compounds exhibit nicotinic pharmacology with a beneficial effect on the CNS nAChRs (e.g., upon the functioning of the CNS), but without significant associated effects on the peripheral nAChRs (compounds specific for CNS nAChRs, without significant effects on cardiovascular and/or skeletal muscle receptor sites).

Dopamine release is believed to be associated with the physiological "reward" associated with consumption of these substances of addiction. Modulation of dopamine release has been proposed for use in treating addiction. Modulation of the (4(2 receptor is one way to modulate dopamine release, and may be at least part of the mechanism by which mecamylamine is effective at treating drug addiction. However, it may be desirable in some instances to modulate dopamine release without antagonizing (4(2 activity. Thus, the availability of a variety of ligands that bind with high affinity and selectivity for receptors other than (4(2, and that modulate dopamine release, are of interest.

A limitation of some nicotinic compounds is that they are associated with various undesirable side effects, for example, by stimulating muscle and ganglionic receptors. It would be desirable to have compounds, compositions and methods for treating and/or preventing central nervous system disorders, and treating and/or preventing drug addiction, promoting smoking cessation, and inhibiting obesity, where the compounds exhibit pharmacology with a beneficial effect (e.g., inhibition of dopamine secretion), but without significant associated side effects. The present invention provides such compounds, compositions and methods.

SUMMARY OF THE INVENTION

Compounds and methods for preventing and/or treating conditions or disorders, such as CNS disorders, are disclosed. The methods involve administering to a subject an effective amount of a heteroaryl-substituted azabicycloalkene or azabicycloalkane, including enantiomerically enriched forms thereof. Also disclosed are pharmaceutical compositions comprising an effective amount of these compounds and the methods of preparing the compounds. The compositions incorporate a compound which, when employed in effective amounts, has the capability of interacting with relevant nAChRs of a subject, and hence has the capability of acting as a therapeutic agent in the prevention or treatment of conditions or disorders. Preferred pharmaceutical compositions comprise novel compounds of the present invention.

The pharmaceutical compositions are useful for preventing and/or treating conditions or disorders, such as CNS disorders and pain. The pharmaceutical compositions provide therapeutic benefit to individuals suffering from such conditions or disorders and exhibiting clinical manifestations of such conditions or disorders. The compounds, administered with the pharmaceutical compositions, can be employed in effective amounts to (i) exhibit nicotinic pharmacology and affect relevant nicotinic receptors sites (e.g., act as a pharmacological modulators at nicotinic receptors), and (ii) modulate neurotransmitter secretion, and hence prevent or suppress the symptoms associated with those diseases. In addition, the compounds have the potential to (i) increase the number of nAChRs of the brain of the patient, (ii) exhibit neuroprotective effects and (iii) when employed in effective amounts, not cause appreciable adverse side effects (e.g., significant increases in blood pressure and heart rate, significant negative effects upon the gastrointestinal tract, and significant effects upon skeletal muscle). The compounds and pharmaceutical compositions including them are believed to be safe and effective with regards to prevention and treatment of various conditions or disorders.

In one embodiment, the compounds and pharmaceutical compositions including them can also be used in methods of treating nicotine addiction, drug addiction, and/or obesity. In this embodiment, the compounds function by decreasing dopamine release, without significantly affecting the (4(2 receptor. Decreased dopamine release results in a decreased physiological "reward" associated with administration of nicotine or illicit drugs, and thus helps overcome addiction.

The foregoing and other aspects of the present invention are explained in detail in the detailed description and examples set forth below.

DETAILED DESCRIPTION OF THE INVENTION

The compounds, compositions and methods described herein will be better understood with reference to the following preferred embodiments. The following definitions will be useful in defining the scope of the invention:

As used herein, "aromatic" refers to 3 to 10, preferably 5 and 6-membered ring aromatic and heteroaromatic rings.

As used herein, "aromatic group-containing species" refer to moieties that are or include an aromatic group. Accordingly, phenyl and benzyl moieties are included in this definition, as both are or include an aromatic group.

As used herein, $C_{1-6}$ alkyl radicals (lower alkyl radicals) contain from 1 to 6 carbon atoms in a straight or branched chain, and also include $C_{3-6}$ cycloalkyl moieties and alkyl radicals that contain $C_{3-6}$ cycloalkyl moieties.

As used herein, $C_{1-6}$ alkoxy radicals contain from 1 to 6 carbon atoms in a straight or branched chain, and also include $C_{3-6}$ cycloalkoxy radicals and alkoxy radicals that contain $C_{3-6}$ cycloalkyl moieties.

As used herein, aryl radicals are selected from phenyl, naphthyl and indenyl.

As used herein, heteroaryl radicals contain from 3 to 10 members, preferably 5 or 6 members, including one or more heteroatoms selected from oxygen, sulfur and nitrogen. Examples of suitable 5-membered ring heteroaryl moieties include furyl, thienyl, pyrrolyl, imidazolyl, oxazolyl, thiazolyl, isoxazolyl, isothiazolyl, tetrazolyl, triazolyl, and pyrazolyl. Examples of suitable 6-membered ring heteroaryl moieties include pyridinyl, pyrimidinyl, pyrazinyl, and pyridazinyl, of which pyridinyl and pyrimidinyl are preferred.

As used herein, halogen is chlorine, iodine, fluorine or bromine.

As used herein, heterocyclyl radicals contain from 3 to 10 members including one or more heteroatoms selected from oxygen, sulfur and nitrogen. Examples of suitable heterocyclyl moieties include, but are not limited to, piperidinyl, morpholinyl, pyrrolidinyl, imidazolidinyl, pyrazolidinyl, isothiazolidinyl, thiazolidinyl, isoxazolidinyl, oxazolidinyl, piperazinyl, oxanyl (tetrahydropyranyl), and oxolanyl (tetrahydrofuranyl).

As used herein, cycloalkyl radicals contain from 3 to 8 carbon atoms. Examples of suitable cycloalkyl radicals include, but are not limited to, cyclopropyl, cyclobutyl, cyclopentyl, cyclohexyl, cycloheptyl, and cyclooctyl.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" is a substance that provides a level of stimulation to its binding partner that is intermediate between that of a full or complete antagonist and an agonist defined by any accepted standard for agonist activity. It will be recognized that stimulation, and hence, inhibition is defined intrinsically for any substance or category of substances to be defined as agonists, antagonists, or partial agonists.

As used herein, a "partial antagonist" is a substance that provides a level of inhibition to its binding partner that is intermediate between that of a full or complete antagonist and an inactive ligand.

As used herein, "intrinsic activity", or "efficacy," relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer and Boddeke, *Trends Pharmacol Sci.* 14(7): 270 (1993). Where such contextually specific evaluations are relevant, and how they might be relevant in the context of the present invention, will be apparent to one of ordinary skill in the art.

As used herein, modulation of a receptor includes agonism, partial agonism, antagonism, partial antagonism, or inverse agonism of a receptor.

As used herein, neurotransmitters whose release is modulated by the compounds described herein include, but are not limited to, acetylcholine, dopamine, norepinephrine, serotonin, and glutamate, and the compounds described herein function as agonists or partial agonists at one or more of the Central Nervous System (CNS) nAChRs.

I. Compounds

The present invention relates to compounds having general Formulas 1 and 2,

Formula 1

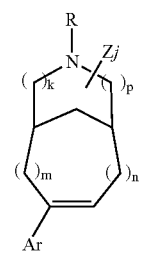

Formula 2

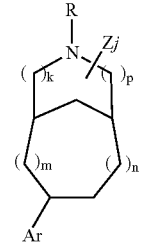

wherein k, m, n, and p are individually 0, 1, 2 or 3, provided that, when k+p=1, m or n or both must be greater than 0;

R is hydrogen, lower alkyl, arylalkyl (including heteroarylalkyl), acyl, alkoxycarbonyl, or aryloxycarbonyl;

Ar is heteroaryl, either monocyclic or polycyclic, optionally substituted at any position with a substituent Z as defined below, with the proviso that in the compounds of Formula 2, when the azabicyclic ring is a 6-azabicyclo[3.2.1]octane, Ar is not pyridine or substituted pyridine;

Z is a non-hydrogen substituent species (attached at a carbon atom of the azabicycle) chosen from among alkyl, substituted alkyl, alkenyl, substituted alkenyl, heterocyclyl, substituted heterocyclyl, cycloalkyl, substituted cycloalkyl, aryl (including heteroaryl), substituted aryl (including heteroaryl), alkylaryl, substituted alkylaryl, arylalkyl, substituted arylalkyl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", —NR'C(=O)O R", —SO$_2$R', —SO$_2$NR'R", and —NR'SO$_2$R", where R' and R" are individually hydrogen, lower alkyl (e.g., straight chain or branched alkyl including C$_1$-C$_6$, preferably C$_1$-C$_4$, such as methyl, ethyl, or isopropyl), cycloalkyl, heterocyclyl, aryl, or arylalkyl (such as benzyl), and r is an integer from 1 to 6. R' and R" can combine to form a cyclic functionality. The term "substituted" as applied to alkyl, aryl (including heteroaryl), cycloalkyl and the like refers to the substituents described above, starting with halo and ending with —NR'SO$_2$R"; and j is 0, 1, or 2.

It is preferred that Ar be a 5-membered or 6-membered heteroaromatic ring. Thus Ar can be depicted as follows:

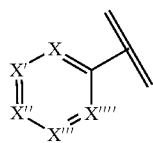

wherein each of X, X', X", X''', and X'''' is individually nitrogen, nitrogen bonded to oxygen (e.g., an N-oxide or N-O functionality), or carbon bonded to H or a non-hydrogen substituent species (such as a substituent species Z as defined herein). No more than three of X, X', X", X''', and X'''' are nitrogen or nitrogen bonded to oxygen, and it is preferred that only one or two of X, X', X", X''', and X'''' be nitrogen or nitrogen bonded to oxygen. In addition, it is highly preferred that not more than one of X, X', X", X''', and X'''' be nitrogen bonded to oxygen; and it is preferred that if one of those species is nitrogen bonded to oxygen, that species is X'''. Most preferably, X''' is nitrogen. In certain preferred circumstances, both X' and X''' are nitrogen. Typically, X, X", and X'''' are carbon bonded to a substituent species, and it is typical that the substituent species at X, X", and X'''' are hydrogen. For certain other preferred compounds where X''' is carbon bonded to a substituent species such as hydrogen, X and X' are both nitrogen. In certain other preferred compounds where X' is carbon bonded to a substituent species such as hydrogen, X and X''' are both nitrogen.

When the value of k+p (as defined above) is greater than 0 (zero), Ar can also be a five 5-membered heteroaromatic ring, such as pyrrole, furan, thiophene, isoxazole, isothiazole, oxazole, thiazole, pyrazole, 1,2,4-oxadiazole, 1,3,4-oxadiazole, or 1,2,4-triazole. Other examples of such rings are described in U.S. Pat. No. 6,022,868 to Olesen et al., the contents of which are incorporated herein by reference in their entirety. Thus, another way of depicting Ar is as follows:

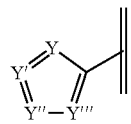

wherein Y and Y" are individually nitrogen, nitrogen bonded to a substituent species, oxygen, sulfur or carbon bonded to a substituent species, and Y' and Y''' are nitrogen or carbon bonded to a substituent species. The dashed lines indicate that the bonds (between Y and Y' and between Y' and Y") can be either single or double bonds. However, when the bond between Y and Y' is a single bond, the bond between Y' and Y" must be a double bond and vice versa. In cases in which Y or Y" is oxygen or sulfur, only one of Y and Y" is either oxygen or sulfur. At least one of Y, Y', Y", and Y''' must be oxygen, sulfur, nitrogen, or nitrogen bonded to a substituent species. It is preferred that no more than three of Y, Y', Y", and Y''' be oxygen, sulfur, nitrogen, or nitrogen bonded to a substituent species. It is further preferred that at least one, but no more than three, of Y, Y', Y", and Y''' be nitrogen. However, when m+n=0, Ar is neither 1,2,5-oxadiazole nor 1,2,5-thiadiazole nor a substituted version thereof.

Substituent species associated with any of X, X', X", X''', X'''', Y, Y', Y", and Y''' (when any is carbon bonded to a substituent species), typically have a sigma m value between about −0.3 and about 0.75, frequently between about −0.25 and about 0.6; and each sigma m value individually can be 0 or not equal to zero; as determined in accordance with Hansch et al., Chem. Rev. 91:165 (1991).

Examples of suitable substituent species associated with any of X, X', X", X''', X'''', Y, Y', Y", and Y''' (when any is carbon bonded to a substituent species), include hydrogen, alkyl, substituted alkyl, alkenyl, substituted alkenyl, heterocyclyl, substituted heterocyclyl, cycloalkyl, substituted cycloalkyl, aryl (including heteroaryl), substituted aryl (including heteroaryl), alkylaryl, substituted alkylaryl, arylalkyl, substituted arylalkyl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", —NR'C(=O)O R", —SO$_2$R', —SO$_2$NR'R", and —NR'SO$_2$R", where R' and R" are individually hydrogen, lower alkyl (e.g., straight chain or branched alkyl including C$_1$-C$_6$, preferably C$_1$-C$_4$, such as methyl, ethyl, or isopropyl), cycloalkyl, heterocyclyl, aryl, or arylalkyl (such as benzyl), and r is an integer from 1 to 6. R' and R" can combine to form a cyclic functionality. The term "substituted" as applied to alkyl, aryl (including heteroaryl), cycloalkyl and the like refers to the substituents described above, starting with halo and ending with —NR'SO$_2$R".

Examples of suitable Ar groups include 3-pyridinyl (unsubstituted or substituted in the 5 and/or 6 position(s) with any of the aforementioned substituents), 5-pyrimidinyl (unsubstituted or substituted in the 2 position with any of the aforementioned substituents), 2-pyrazinyl and 3-pyridazinyl, 4 and 5-isoxazolyl, 4 and 5-isothiazolyl, 5-oxazolyl, 5-thiazolyl, 5-(1,2,4-oxadiazolyl), 2-(1,3,4-oxadiazolyl), or 3-(1,2,4-triazolyl).

Adjacent substituents of X, X', X", X'", X"", Y, Y', Y", and Y'" (when substituents are present) can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities.

The compounds can occur in stereoisomeric forms, including both single enantiomers and racemic mixtures of such compounds, as well as mixtures of varying degrees of enantiomeric excess. Compounds with a plane of symmetry, such that the compound is not chiral, can be preferred for ease of preparation.

The compounds can be in a free base form or in a salt form (e.g., as pharmaceutically acceptable salts). Examples of suitable pharmaceutically acceptable salts have been listed above. Representative salts are provided as described in U.S. Pat. No. 5,597,919 to Dull et al., U.S. Pat. No. 5,616,716 to Dull et al. and U.S. Pat. No. 5,663,356 to Ruecroft et al., the disclosures of which are incorporated herein by reference in their entirety. The compounds of the present invention are nitrogenous bases, and, in some cases, are capable of forming quaternary ammonium salts by reaction with alkylating agents (e.g., alkyl halides). Such quaternary ammonium salts are also compounds of the present invention.

Specific sub-structures falling within the scope of Formulas 1 and 2 are shown below:

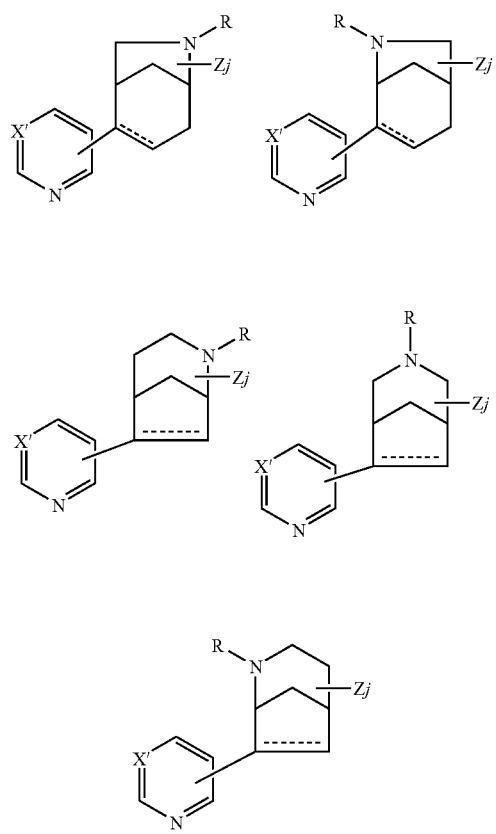

where the hashed bond indicates the optional presence of a double bond (and wherein the presence of adjacent hashed bonds indicates that one (but not both) of the hashed bonds can be a double bond), X' is N, or carbon bonded to H or a substituent Z as defined above, and R, Z, and j are defined as above.

Within the group of structures shown above as falling within Formulas 1 and 2, the following group of structures is a preferred subset:

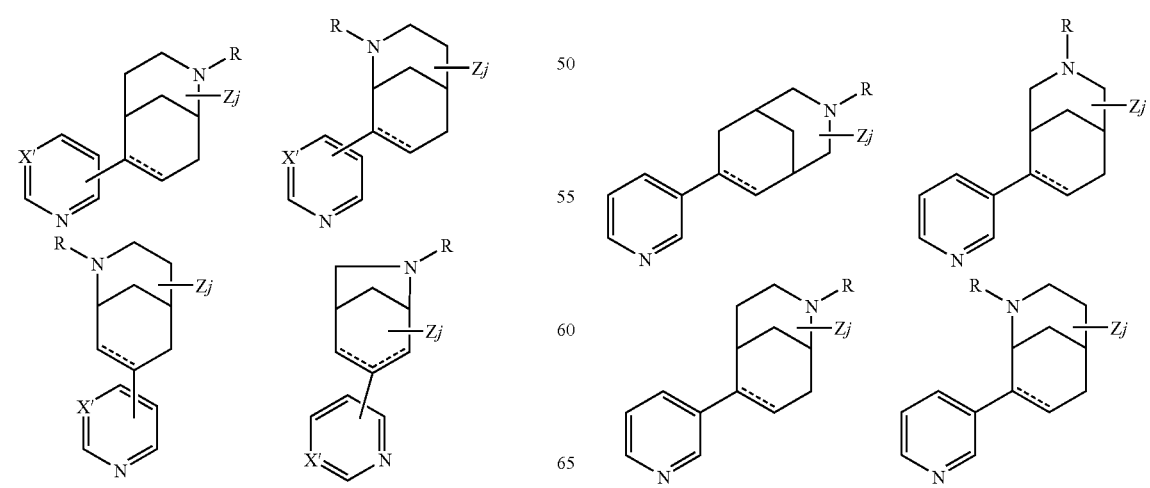

-continued
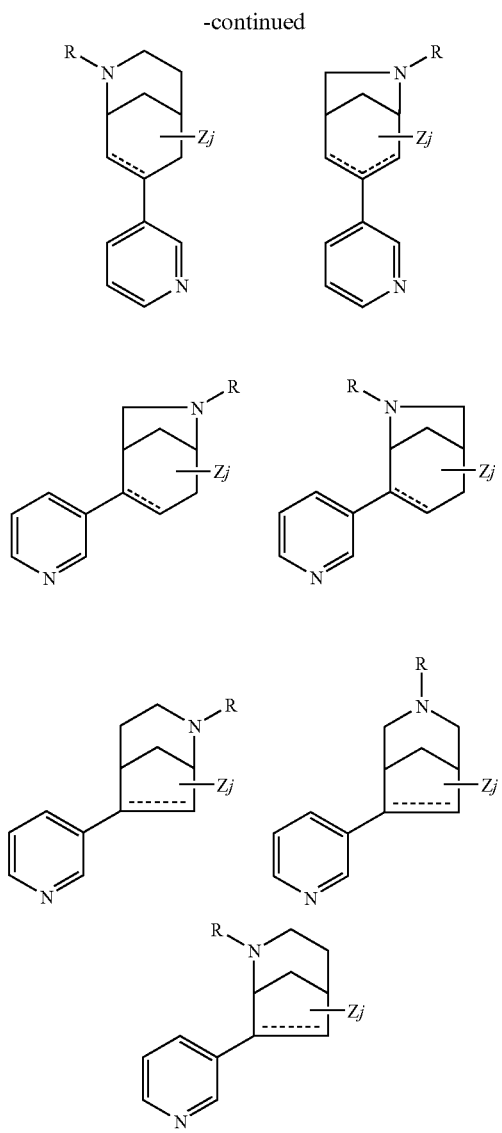
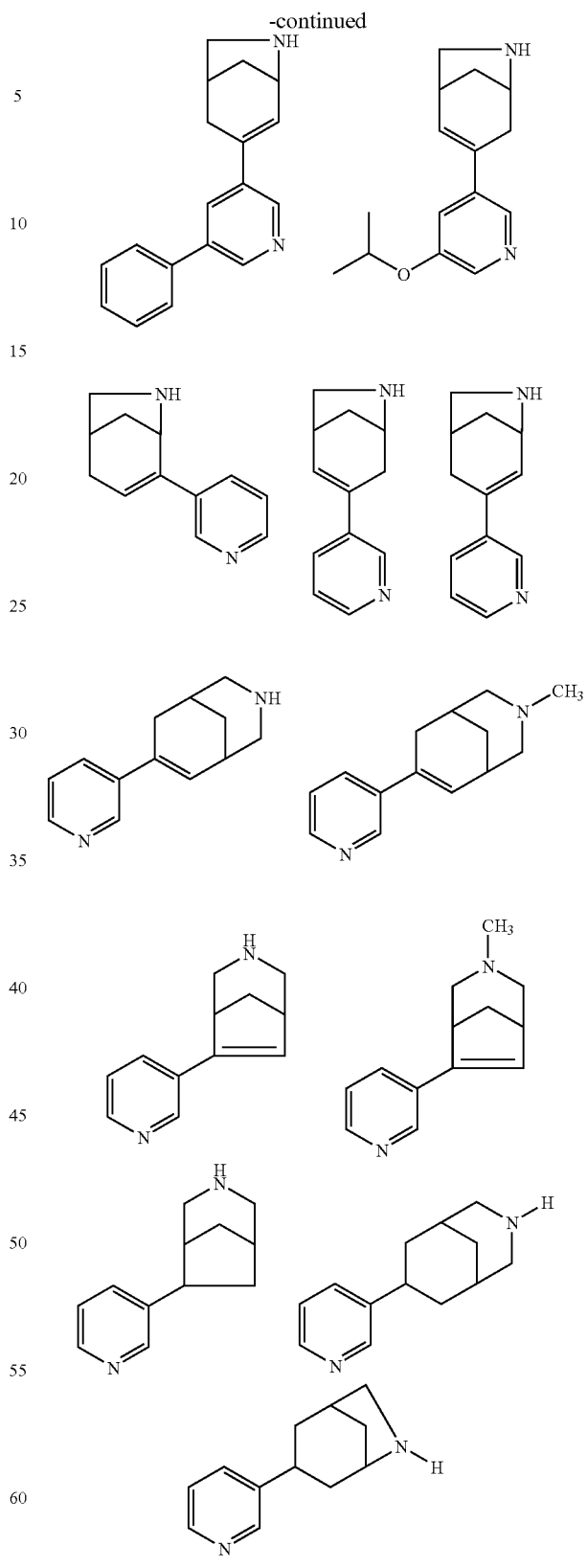
where R, Z and j are as defined above, and the ashed bond indicates the optional presence of a double bond. Specific compounds within this subset include the following:
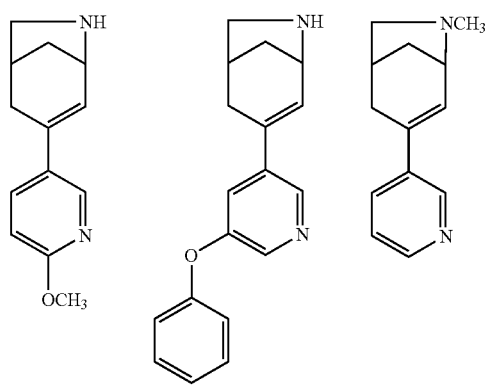
Representative compounds of the present invention include the following:
2-(3-pyridinyl)-6-azabicyclo[3.2.1]oct-2-ene, 3-(3-pyridinyl)-6-azabicyclo[3.2.1]oct-2-ene,
3-(3-pyridinyl)-6-azabicyclo[3.2.1]oct-3-ene,
4-(3-pyridinyl)-6-azabicyclo[3.2.1]oct-3-ene,
6-(3-pyridinyl)-2-azabicyclo[3.2.1]oct-6-ene,
7-(3-pyridinyl)-2-azabicyclo[3.2.1]oct-6-ene,
6-(3-pyridinyl)-3-azabicyclo[3.2.1]oct-6-ene,
6-(3-pyridinyl)-2-azabicyclo[3.3.1]non-6-ene,
7-(3-pyridinyl)-2-azabicyclo[3.3.1]non-6-ene,
6-(3-pyridinyl)-3-azabicyclo[3.3.1]non-6-ene,
7-(3-pyridinyl)-3-azabicyclo[3.3.1]non-6-ene,
7-(3-pyridinyl)-2-azabicyclo[3.3.1]non-7-ene,
8-(3-pyridinyl)-2-azabicyclo[3.3.1]non-7-ene,
4-(3-pyridinyl)-8-azabicyclo[5.1.1]non-3-ene,
3-(3-pyridinyl)-8-azabicyclo[4.3.1]dec-3-ene,
8-(3-pyridinyl)-4-azabicyclo[5.2.1]dec-8-ene,
9-(3-pyridinyl)-4-azabicyclo[5.3.1]undec-8-ene,
6-(3-pyridinyl)-2-azabicyclo[3.2.1]octane,
7-(3-pyridinyl)-2-azabicyclo[3.2.1]octane,
6-(3-pyridinyl)-3-azabicyclo[3.2.1]octane,
6-(3-pyridinyl)-2-azabicyclo[3.3.1]nonane,
7-(3-pyridinyl)-2-azabicyclo[3.3.1]nonane,
8-(3-pyridinyl)-2-azabicyclo[3.3.1]nonane,
6-(3-pyridinyl)-3-azabicyclo[3.3.1]nonane,
7-(3-pyridinyl)-3-azabicyclo[3.3.1]nonane,
4-(3-pyridinyl)-8-azabicyclo[5.1.1]nonane,
3-(3-pyridinyl)-8-azabicyclo[4.3.1]decane,
8-(3-pyridinyl)-4-azabicyclo[5.2.1]decane,
and 9-(3-pyridinyl)-4-azabicyclo[5.3.1]undecane.

Further representative compounds of the present invention include the following:
2-(5-methoxy-3-pyridinyl)-6-azabicyclo[3.2.1]oct-2-ene,
3-(5-methoxy-3-pyridinyl)-6-azabicyclo[3.2.1]oct-2-ene,
3-(5-methoxy-3-pyridinyl)-6-azabicyclo[3.2.1]oct-3-ene,
4-(5-methoxy-3-pyridinyl)-6-azabicyclo[3.2.1]oct-3-ene,
6-(5-methoxy-3-pyridinyl)-2-azabicyclo[3.2.1]oct-6-ene,
7-(5-methoxy-3-pyridinyl)-2-azabicyclo[3.2.1]oct-6-ene,
6-(5-methoxy-3-pyridinyl)-3-azabicyclo[3.2.1]oct-6-ene,
6-(5-methoxy-3-pyridinyl)-2-azabicyclo[3.3.1]non-6-ene,
7-(5-methoxy-3-pyridinyl)-2-azabicyclo[3.3.1]non-6-ene,
6-(5-methoxy-3-pyridinyl)-3-azabicyclo[3.3.1]non-6-ene,
7-(5-methoxy-3-pyridinyl)-3-azabicyclo[3.3.1]non-6-ene,
7-(5-methoxy-3-pyridinyl)-2-azabicyclo[3.3.1]non-7-ene,
8-(5-methoxy-3-pyridinyl)-2-azabicyclo[3.3.1]non-7-ene,
4-(5-methoxy-3-pyridinyl)-8-azabicyclo[5.1.1]non-3-ene,
3-(5-methoxy-3-pyridinyl)-8-azabicyclo[4.3.1]dec-3-ene,
8-(5-methoxy-3-pyridinyl)-4-azabicyclo[5.2.1]dec-8-ene,
9-(5-methoxy-3-pyridinyl)-4-azabicyclo[5.3.1]undec-8-ene,
6-(5-methoxy-3-pyridinyl)-2-azabicyclo[3.2.1]octane,
7-(5-methoxy-3-pyridinyl)-2-azabicyclo[3.2.1]octane,
6-(5-methoxy-3-pyridinyl)-3-azabicyclo[3.2.1]octane,
6-(5-methoxy-3-pyridinyl)-2-azabicyclo[3.3.1]nonane,
7-(5-methoxy-3-pyridinyl)-2-azabicyclo[3.3.1]nonane,
8-(5-methoxy-3-pyridinyl)-2-azabicyclo[3.3.1]nonane,
6-(5-methoxy-3-pyridinyl)-3-azabicyclo[3.3.1]nonane,
7-(5-methoxy-3-pyridinyl)-3-azabicyclo[3.3.1]nonane,
4-(5-methoxy-3-pyridinyl)-8-azabicyclo[5.1.1]nonane,
3-(5-methoxy-3-pyridinyl)-8-azabicyclo[4.3.1]decane,
8-(5-methoxy-3-pyridinyl)-4-azabicyclo[5.2.1]decane,
and 9-(5-methoxy-3-pyridinyl)-4-azabicyclo[5.3.1]undecane.

Further representative compounds of the present invention include the following:
2-(6-methoxy-3-pyridinyl)-6-azabicyclo[3.2.1]oct-2-ene,
3-(6-methoxy-3-pyridinyl)-6-azabicyclo[3.2.1]oct-2-ene,
3-(6-methoxy-3-pyridinyl)-6-azabicyclo[3.2.1]oct-3-ene,
4-(6-methoxy-3-pyridinyl)-6-azabicyclo[3.2.1]oct-3-ene,
6-(6-methoxy-3-pyridinyl)-2-azabicyclo[3.2.1]oct-6-ene,
7-(6-methoxy-3-pyridinyl)-2-azabicyclo[3.2.1]oct-6-ene,
6-(6-methoxy-3-pyridinyl)-3-azabicyclo[3.2.1]oct-6-ene,
6-(6-methoxy-3-pyridinyl)-2-azabicyclo[3.3.1]non-6-ene,
7-(6-methoxy-3-pyridinyl)-2-azabicyclo[3.3.1]non-6-ene,
6-(6-methoxy-3-pyridinyl)-3-azabicyclo[3.3.1]non-6-ene,
7-(6-methoxy-3-pyridinyl)-3-azabicyclo[3.3.1]non-6-ene,
7-(6-methoxy-3-pyridinyl)-2-azabicyclo[3.3.1]non-7-ene,
8-(6-methoxy-3-pyridinyl)-2-azabicyclo[3.3.1]non-7-ene,
4-(6-methoxy-3-pyridinyl)-8-azabicyclo[5.1.1]non-3-ene,
3-(6-methoxy-3-pyridinyl)-8-azabicyclo[4.3.1]dec-3-ene,
8-(6-methoxy-3-pyridinyl)-4-azabicyclo[5.2.1]dec-8-ene,
9-(6-methoxy-3-pyridinyl)-4-azabicyclo[5.3.1]undec-8-ene,
6-(6-methoxy-3-pyridinyl)-2-azabicyclo[3.2.1]octane,
7-(6-methoxy-3-pyridinyl)-2-azabicyclo[3.2.1]octane,
6-(6-methoxy-3-pyridinyl)-3-azabicyclo[3.2.1]octane,
6-(6-methoxy-3-pyridinyl)-2-azabicyclo[3.3.1]nonane,
7-(6-methoxy-3-pyridinyl)-2-azabicyclo[3.3.1]nonane,
8-(6-methoxy-3-pyridinyl)-2-azabicyclo[3.3.1]nonane,
6-(6-methoxy-3-pyridinyl)-3-azabicyclo[3.3.1]nonane,
7-(6-methoxy-3-pyridinyl)-3-azabicyclo[3.3.1]nonane,
4-(6-methoxy-3-pyridinyl)-8-azabicyclo[5.1.1]nonane,
3-(6-methoxy-3-pyridinyl)-8-azabicyclo[4.3.1]decane,
8-(6-methoxy-3-pyridinyl)-4-azabicyclo[5.2.1]decane,
and 9-(6-methoxy-3-pyridinyl)-4-azabicyclo[5.3.1]undecane.

Further representative compounds of the present invention include the following:
2-(5-isopropoxy-3-pyridinyl)-6-azabicyclo[3.2.1]oct-2-ene,
3-(5-isopropoxy-3-pyridinyl)-6-azabicyclo[3.2.1]oct-2-ene,
3-(5-isopropoxy-3-pyridinyl)-6-azabicyclo[3.2.1]oct-3-ene,
4-(5-isopropoxy-3-pyridinyl)-6-azabicyclo[3.2.1]oct-3-ene,
6-(5-isopropoxy-3-pyridinyl)-2-azabicyclo[3.2.1]oct-6-ene,
7-(5-isopropoxy-3-pyridinyl)-2-azabicyclo[3.2.1]oct-6-ene,
6-(5-isopropoxy-3-pyridinyl)-3-azabicyclo[3.2.1]oct-6-ene,
6-(5-isopropoxy-3-pyridinyl)-2-azabicyclo[3.3.1]non-6-ene,
7-(5-isopropoxy-3-pyridinyl)-2-azabicyclo[3.3.1]non-6-ene,
6-(5-isopropoxy-3-pyridinyl)-3-azabicyclo[3.3.1]non-6-ene,
7-(5-isopropoxy-3-pyridinyl)-3-azabicyclo[3.3.1]non-6-ene,
7-(5-isopropoxy-3-pyridinyl)-2-azabicyclo[3.3.1]non-7-ene,
8-(5-isopropoxy-3-pyridinyl)-2-azabicyclo[3.3.1]non-7-ene,
4-(5-isopropoxy-3-pyridinyl)-8-azabicyclo[5.1.1]non-3-ene,
3-(5-isopropoxy-3-pyridinyl)-8-azabicyclo[4.3.1]dec-3-ene,
8-(5-isopropoxy-3-pyridinyl)-4-azabicyclo[5.2.1]dec-8-ene,
9-(5-isopropoxy-3-pyridinyl)-4-azabicyclo[5.3.1]undec-8-ene,
6-(5-isopropoxy-3-pyridinyl)-2-azabicyclo[3.2.1]octane,
7-(5-isopropoxy-3-pyridinyl)-2-azabicyclo[3.2.1]octane,
6-(5-isopropoxy-3-pyridinyl)-3-azabicyclo[3.2.1]octane,
6-(5-isopropoxy-3-pyridinyl)-2-azabicyclo[3.3.1]nonane,
7-(5-isopropoxy-3-pyridinyl)-2-azabicyclo[3.3.1]nonane,
8-(5-isopropoxy-3-pyridinyl)-2-azabicyclo[3.3.1]nonane,
6-(5-isopropoxy-3-pyridinyl)-3-azabicyclo[3.3.1]nonane,
7-(5-isopropoxy-3-pyridinyl)-3-azabicyclo[3.3.1]nonane,
4-(5-isopropoxy-3-pyridinyl)-8-azabicyclo[5.1.1]nonane,
3-(5-isopropoxy-3-pyridinyl)-8-azabicyclo[4.3.1]decane,
8-(5-isopropoxy-3-pyridinyl)-4-azabicyclo[5.2.1]decane,
and 9-(5-isopropoxy-3-pyridinyl)-4-azabicyclo[5.3.1]undecane.

Further representative compounds of the present invention include the following:
2-(5-phenoxy-3-pyridinyl)-6-azabicyclo[3.2.1]oct-2-ene,
3-(5-phenoxy-3-pyridinyl)-6-azabicyclo[3.2.1]oct-2-ene,
3-(5-phenoxy-3-pyridinyl)-6-azabicyclo[3.2.1]oct-3-ene,
4-(5-phenoxy-3-pyridinyl)-6-azabicyclo[3.2.1]oct-3-ene,
6-(5-phenoxy-3-pyridinyl)-2-azabicyclo[3.2.1]oct-6-ene,
7-(5-phenoxy-3-pyridinyl)-2-azabicyclo[3.2.1]oct-6-ene,
6-(5-phenoxy-3-pyridinyl)-3-azabicyclo[3.2.1]oct-6-ene,
6-(5-phenoxy-3-pyridinyl)-2-azabicyclo[3.3.1]non-6-ene,
7-(5-phenoxy-3-pyridinyl)-2-azabicyclo[3.3.1]non-6-ene,
6-(5-phenoxy-3-pyridinyl)-3-azabicyclo[3.3.1]non-6-ene,
7-(5-phenoxy-3-pyridinyl)-3-azabicyclo[3.3.1]non-6-ene,
7-(5-phenoxy-3-pyridinyl)-2-azabicyclo[3.3.1]non-7-ene,
8-(5-phenoxy-3-pyridinyl)-2-azabicyclo[3.3.1]non-7-ene,
4-(5-phenoxy-3-pyridinyl)-8-azabicyclo[5.1.1]non-3-ene,
3-(5-phenoxy-3-pyridinyl)-8-azabicyclo[4.3.1]dec-3-ene,
8-(5-phenoxy-3-pyridinyl)-4-azabicyclo[5.2.1]dec-8-ene,
9-(5-phenoxy-3-pyridinyl)-4-azabicyclo[5.3.1]undec-8-ene,
6-(5-phenoxy-3-pyridinyl)-2-azabicyclo[3.2.1]octane,
7-(5-phenoxy-3-pyridinyl)-2-azabicyclo[3.2.1]octane,
6-(5-phenoxy-3-pyridinyl)-3-azabicyclo[3.2.1]octane,
6-(5-phenoxy-3-pyridinyl)-2-azabicyclo[3.3.1]nonane,
7-(5-phenoxy-3-pyridinyl)-2-azabicyclo[3.3.1]nonane,
8-(5-phenoxy-3-pyridinyl)-2-azabicyclo[3.3.1]nonane,
6-(5-phenoxy-3-pyridinyl)-3-azabicyclo[3.3.1]nonane,
7-(5-phenoxy-3-pyridinyl)-3-azabicyclo[3.3.1]nonane,
4-(5-phenoxy-3-pyridinyl)-8-azabicyclo[5.1.1]nonane,
3-(5-phenoxy-3-pyridinyl)-8-azabicyclo[4.3.1]decane,
8-(5-phenoxy-3-pyridinyl)-4-azabicyclo[5.2.1]decane,
and 9-(5-phenoxy-3-pyridinyl)-4-azabicyclo[5.3.1]undecane.

Further representative compounds of the present invention include the following:
2-(5-phenyl-3-pyridinyl)-6-azabicyclo[3.2.1]oct-2-ene,
3-(5-phenyl-3-pyridinyl)-6-azabicyclo[3.2.1]oct-2-ene,
3-(5-phenyl-3-pyridinyl)-6-azabicyclo[3.2.1]oct-3-ene,
4-(5-phenyl-3-pyridinyl)-6-azabicyclo[3.2.1]oct-3-ene,
6-(5-phenyl-3-pyridinyl)-2-azabicyclo[3.2.1]oct-6-ene,
7-(5-phenyl-3-pyridinyl)-2-azabicyclo[3.2.1]oct-6-ene,
6-(5-phenyl-3-pyridinyl)-3-azabicyclo[3.2.1]oct-6-ene,
6-(5-phenyl-3-pyridinyl)-2-azabicyclo[3.3.1]non-6-ene,
7-(5-phenyl-3-pyridinyl)-2-azabicyclo[3.3.1]non-6-ene,
6-(5-phenyl-3-pyridinyl)-3-azabicyclo[3.3.1]non-6-ene,
7-(5-phenyl-3-pyridinyl)-3-azabicyclo[3.3.1]non-6-ene,
7-(5-phenyl-3-pyridinyl)-2-azabicyclo[3.3.1]non-7-ene,
8-(5-phenyl-3-pyridinyl)-2-azabicyclo[3.3.1]non-7-ene,
4-(5-phenyl-3-pyridinyl)-8-azabicyclo[5.1.1]non-3-ene,
3-(5-phenyl-3-pyridinyl)-8-azabicyclo[4.3.1]dec-3-ene,
8-(5-phenyl-3-pyridinyl)-4-azabicyclo[5.2.1]dec-8-ene,
9-(5-phenyl-3-pyridinyl)-4-azabicyclo[5.3.1]undec-8-ene,
6-(5-phenyl-3-pyridinyl)-2-azabicyclo[3.2.1]octane,
7-(5-phenyl-3-pyridinyl)-2-azabicyclo[3.2.1]octane,
6-(5-phenyl-3-pyridinyl)-3-azabicyclo[3.2.1]octane,
6-(5-phenyl-3-pyridinyl)-2-azabicyclo[3.3.1]nonane,
7-(5-phenyl-3-pyridinyl)-2-azabicyclo[3.3.1]nonane,
8-(5-phenyl-3-pyridinyl)-2-azabicyclo[3.3.1]nonane,
6-(5-phenyl-3-pyridinyl)-3-azabicyclo[3.3.1]nonane,
7-(5-phenyl-3-pyridinyl)-3-azabicyclo[3.3.1]nonane,
4-(5-phenyl-3-pyridinyl)-8-azabicyclo[5.1.1]nonane,
3-(5-phenyl-3-pyridinyl)-8-azabicyclo[4.3.1]decane,
8-(5-phenyl-3-pyridinyl)-4-azabicyclo[5.2.1]decane,
and 9-(5-phenyl-3-pyridinyl)-4-azabicyclo[5.3.1]undecane.

Further representative compounds of the present invention include the following:
2-(6-chloro-3-pyridinyl)-6-azabicyclo[3.2.1]oct-2-ene,
3-(6-chloro-3-pyridinyl)-6-azabicyclo[3.2.1]oct-2-ene,
3-(6-chloro-3-pyridinyl)-6-azabicyclo[3.2.1]oct-3-ene,
4-(6-chloro-3-pyridinyl)-6-azabicyclo[3.2.1]oct-3-ene,
6-(6-chloro-3-pyridinyl)-2-azabicyclo[3.2.1]oct-6-ene,
7-(6-chloro-3-pyridinyl)-2-azabicyclo[3.2.1]oct-6-ene,
6-(6-chloro-3-pyridinyl)-3-azabicyclo[3.2.1]oct-6-ene,
6-(6-chloro-3-pyridinyl)-2-azabicyclo[3.3.1]non-6-ene,
7-(6-chloro-3-pyridinyl)-2-azabicyclo[3.3.1]non-6-ene,
6-(6-chloro-3-pyridinyl)-3-azabicyclo[3.3.1]non-6-ene,
7-(6-chloro-3-pyridinyl)-3-azabicyclo[3.3.1]non-6-ene,
7-(6-chloro-3-pyridinyl)-2-azabicyclo[3.3.1]non-7-ene,
8-(6-chloro-3-pyridinyl)-2-azabicyclo[3.3.1]non-7-ene,
4-(6-chloro-3-pyridinyl)-8-azabicyclo[5.1.1]non-3-ene,
3-(6-chloro-3-pyridinyl)-8-azabicyclo[4.3.1]dec-3-ene,
8-(6-chloro-3-pyridinyl)-4-azabicyclo[5.2.1]dec-8-ene,
9-(6-chloro-3-pyridinyl)-4-azabicyclo[5.3.1]undec-8-ene,
6-(6-chloro-3-pyridinyl)-2-azabicyclo[3.2.1]octane,
7-(6-chloro-3-pyridinyl)-2-azabicyclo[3.2.1]octane,
6-(6-chloro-3-pyridinyl)-3-azabicyclo[3.2.1]octane,
6-(6-chloro-3-pyridinyl)-2-azabicyclo[3.3.1]nonane,
7-(6-chloro-3-pyridinyl)-2-azabicyclo[3.3.1]nonane,
8-(6-chloro-3-pyridinyl)-2-azabicyclo[3.3.1]nonane,
6-(6-chloro-3-pyridinyl)-3-azabicyclo[3.3.1]nonane,
7-(6-chloro-3-pyridinyl)-3-azabicyclo[3.3.1]nonane,
4-(6-chloro-3-pyridinyl)-8-azabicyclo[5.1.1]nonane,
3-(6-chloro-3-pyridinyl)-8-azabicyclo[4.3.1]decane,
8-(6-chloro-3-pyridinyl)-4-azabicyclo[5.2.1]decane,
and 9-(6-chloro-3-pyridinyl)-4-azabicyclo[5.3.1]undecane.

Further representative compounds of the present invention include the following:
2-(5-pyrimidinyl)-6-azabicyclo[3.2.1]oct-2-ene,
3-(5-pyrimidinyl)-6-azabicyclo[3.2.1]oct-2-ene,
3-(5-pyrimidinyl)-6-azabicyclo[3.2.1]oct-3-ene,
4-(5-pyrimidinyl)-6-azabicyclo[3.2.1]oct-3-ene,
6-(5-pyrimidinyl)-2-azabicyclo[3.2.1]oct-6-ene,
7-(5-pyrimidinyl)-2-azabicyclo[3.2.1]oct-6-ene,
6-(5-pyrimidinyl)-3-azabicyclo[3.2.1]oct-6-ene,
6-(5-pyrimidinyl)-2-azabicyclo[3.3.1]non-6-ene,
7-(5-pyrimidinyl)-2-azabicyclo[3.3.1]non-6-ene,
6-(5-pyrimidinyl)-3-azabicyclo[3.3.1]non-6-ene,
7-(5-pyrimidinyl)-3-azabicyclo[3.3.1]non-6-ene,
7-(5-pyrimidinyl)-2-azabicyclo[3.3.1]non-7-ene,
8-(5-pyrimidinyl)-2-azabicyclo[3.3.1]non-7-ene,
4-(5-pyrimidinyl)-8-azabicyclo[5.1.1]non-3-ene,
3-(5-pyrimidinyl)-8-azabicyclo[4.3.1]dec-3-ene,
8-(5-pyrimidinyl)-4-azabicyclo[5.2.1]dec-8-ene,
9-(5-pyrimidinyl)-4-azabicyclo[5.3.1]undec-8-ene,
2-(5-pyrimidinyl)-6-azabicyclo[3.2.1]octane,
3-(5-pyrimidinyl)-6-azabicyclo[3.2.1]octane,
4-(5-pyrimidinyl)-6-azabicyclo[3.2.1]octane,
6-(5-pyrimidinyl)-2-azabicyclo[3.2.1]octane,
7-(5-pyrimidinyl)-2-azabicyclo[3.2.1]octane,
6-(5-pyrimidinyl)-3-azabicyclo[3.2.1]octane,
6-(5-pyrimidinyl)-2-azabicyclo[3.3.1]nonane,
7-(5-pyrimidinyl)-2-azabicyclo[3.3.1]nonane,
8-(5-pyrimidinyl)-2-azabicyclo[3.3.1]nonane,
6-(5-pyrimidinyl)-3-azabicyclo[3.3.1]nonane,
7-(5-pyrimidinyl)-3-azabicyclo[3.3.1]nonane,
4-(5-pyrimidinyl)-8-azabicyclo[5.1.1]nonane,
3-(5-pyrimidinyl)-8-azabicyclo[4.3.1]decane,
8-(5-pyrimidinyl)-4-azabicyclo[5.2.1]decane,
and 9-(5-pyrimidinyl)-4-azabicyclo[5.3.1]undecane.

Further representative compounds of the present invention include the following:
2-(3-pyrrolyl)-6-azabicyclo[3.2.1]oct-2-ene,
3-(3-pyrrolyl)-6-azabicyclo[3.2.1]oct-2-ene,
3-(3-pyrrolyl)-6-azabicyclo[3.2.1]oct-3-ene,
4-(3-pyrrolyl)-6-azabicyclo[3.2.1]oct-3-ene, 6-(3-pyrrolyl)-2-azabicyclo[3.2.1]oct-6-ene,
7-(3-pyrrolyl)-2-azabicyclo[3.2.1]oct-6-ene,
6-(3-pyrrolyl)-3-azabicyclo[3.2.1]oct-6-ene,
6-(3-pyrrolyl)-2-azabicyclo[3.3.1]non-6-ene,
7-(3-pyrrolyl)-2-azabicyclo[3.3.1]non-6-ene,
6-(3-pyrrolyl)-3-azabicyclo[3.3.1]non-6-ene,
7-(3-pyrrolyl)-3-azabicyclo[3.3.1]non-6-ene,
7-(3-pyrrolyl)-2-azabicyclo[3.3.1]non-7-ene,
8-(3-pyrrolyl)-2-azabicyclo[3.3.1]non-7-ene,
4-(3-pyrrolyl)-8-azabicyclo[5.1.1]non-3-ene,
3-(3-pyrrolyl)-8-azabicyclo[4.3.1]dec-3-ene,
8-(3-pyrrolyl)-4-azabicyclo[5.2.1]dec-8-ene,
9-(3-pyrrolyl)-4-azabicyclo[5.3.1]undec-8-ene,
2-(3-pyrrolyl)-6-azabicyclo[3.2.1]octane,
3-(3-pyrrolyl)-6-azabicyclo[3.2.1]octane,
4-(3-pyrrolyl)-6-azabicyclo[3.2.1]octane,
6-(3-pyrrolyl)-2-azabicyclo[3.2.1]octane,
7-(3-pyrrolyl)-2-azabicyclo[3.2.1]octane,
6-(3-pyrrolyl)-3-azabicyclo[3.2.1]octane,
6-(3-pyrrolyl)-2-azabicyclo[3.3.1]nonane,
7-(3-pyrrolyl)-2-azabicyclo[3.3.1]nonane,
8-(3-pyrrolyl)-2-azabicyclo[3.3.1]nonane,
6-(3-pyrrolyl)-3-azabicyclo[3.3.1]nonane,
7-(3-pyrrolyl)-3-azabicyclo[3.3.1]nonane,
4-(3-pyrrolyl)-8-azabicyclo[5.1.1]nonane,
3-(3-pyrrolyl)-8-azabicyclo[4.3.1]decane,
8-(3-pyrrolyl)-4-azabicyclo[5.2.1]decane,
and 9-(3-pyrrolyl)-4-azabicyclo[5.3.1]undecane.

Further representative compounds of the present invention include the following:
2-(4-pyrazolyl)-6-azabicyclo[3.2.1]oct-2-ene,
3-(4-pyrazolyl)-6-azabicyclo[3.2.1]oct-2-ene,
3-(4-pyrazolyl)-6-azabicyclo[3.2.1]oct-3-ene,
4-(4-pyrazolyl)-6-azabicyclo[3.2.1]oct-3-ene,
6-(4-pyrazolyl)-2-azabicyclo[3.2.1]oct-6-ene,
7-(4-pyrazolyl)-2-azabicyclo[3.2.1]oct-6-ene,
6-(4-pyrazolyl)-3-azabicyclo[3.2.1]oct-6-ene,
6-(4-pyrazolyl)-2-azabicyclo[3.3.1]non-6-ene,
7-(4-pyrazolyl)-2-azabicyclo[3.3.1]non-6-ene,
6-(4-pyrazolyl)-3-azabicyclo[3.3.1]non-6-ene,
7-(4-pyrazolyl)-3-azabicyclo[3.3.1]non-6-ene,
7-(4-pyrazolyl)-2-azabicyclo[3.3.1]non-7-ene,
8-(4-pyrazolyl)-2-azabicyclo[3.3.1]non-7-ene,
4-(4-pyrazolyl)-8-azabicyclo[5.1.1]non-3-ene,
3-(4-pyrazolyl)-8-azabicyclo[4.3.1]dec-3-ene,
8-(4-pyrazolyl)-4-azabicyclo[5.2.1]dec-8-ene,
9-(4-pyrazolyl)-4-azabicyclo[5.3.1]undec-8-ene,
2-(4-pyrazolyl)-6-azabicyclo[3.2.1]octane,
3-(4-pyrazolyl)-6-azabicyclo[3.2.1]octane,
4-(4-pyrazolyl)-6-azabicyclo[3.2.1]octane,
6-(4-pyrazolyl)-2-azabicyclo[3.2.1]octane,
7-(4-pyrazolyl)-2-azabicyclo[3.2.1]octane,
6-(4-pyrazolyl)-3-azabicyclo[3.2.1]octane,
6-(4-pyrazolyl)-2-azabicyclo[3.3.1]nonane,
7-(4-pyrazolyl)-2-azabicyclo[3.3.1]nonane,
8-(4-pyrazolyl)-2-azabicyclo[3.3.1]nonane,
6-(4-pyrazolyl)-3-azabicyclo[3.3.1]nonane,
7-(4-pyrazolyl)-3-azabicyclo[3.3.1]nonane,
4-(4-pyrazolyl)-8-azabicyclo[5.1.1]nonane,
3-(4-pyrazolyl)-8-azabicyclo[4.3.1]decane,
8-(4-pyrazolyl)-4-azabicyclo[5.2.1]decane,
and 9-(4-pyrazolyl)-4-azabicyclo[5.3.1]undecane.

Further representative compounds of the present invention include the following:
2-(4-isoxazolyl)-6-azabicyclo[3.2.1]oct-2-ene,
3-(4-isoxazolyl)-6-azabicyclo[3.2.1]oct-2-ene,
3-(4-isoxazolyl)-6-azabicyclo[3.2.1]oct-3-ene,
4-(4-isoxazolyl)-6-azabicyclo[3.2.1]oct-3-ene,
6-(4-isoxazolyl)-2-azabicyclo[3.2.1]oct-6-ene,
7-(4-isoxazolyl)-2-azabicyclo[3.2.1]oct-6-ene,
6-(4-isoxazolyl)-3-azabicyclo[3.2.1]oct-6-ene,
6-(4-isoxazolyl)-2-azabicyclo[3.3.1]non-6-ene,
7-(4-isoxazolyl)-2-azabicyclo[3.3.1]non-6-ene,
6-(4-isoxazolyl)-3-azabicyclo[3.3.1]non-6-ene,
7-(4-isoxazolyl)-3-azabicyclo[3.3.1]non-6-ene,
7-(4-isoxazolyl)-2-azabicyclo[3.3.1]non-7-ene,
8-(4-isoxazolyl)-2-azabicyclo[3.3.1]non-7-ene,
4-(4-isoxazolyl)-8-azabicyclo[5.1.1]non-3-ene,
3-(4-isoxazolyl)-8-azabicyclo[4.3.1]dec-3-ene,
8-(4-isoxazolyl)-4-azabicyclo[5.2.1]dec-8-ene,
9-(4-isoxazolyl)-4-azabicyclo[5.3.1]undec-8-ene,
2-(4-isoxazolyl)-6-azabicyclo[3.2.1]octane,
3-(4-isoxazolyl)-6-azabicyclo[3.2.1]octane,
4-(4-isoxazolyl)-6-azabicyclo[3.2.1]octane,
6-(4-isoxazolyl)-2-azabicyclo[3.2.1]octane,
7-(4-isoxazolyl)-2-azabicyclo[3.2.1]octane,
6-(4-isoxazolyl)-3-azabicyclo[3.2.1]octane,
6-(4-isoxazolyl)-2-azabicyclo[3.3.1]nonane,
7-(4-isoxazolyl)-2-azabicyclo[3.3.1]nonane,
8-(4-isoxazolyl)-2-azabicyclo[3.3.1]nonane,
6-(4-isoxazolyl)-3-azabicyclo[3.3.1]nonane,
7-(4-isoxazolyl)-3-azabicyclo[3.3.1]nonane,
4-(4-isoxazolyl)-8-azabicyclo[5.1.1]nonane,
3-(4-isoxazolyl)-8-azabicyclo[4.3.1]decane,
8-(4-isoxazolyl)-4-azabicyclo[5.2.1]decane,
and 9-(4-isoxazolyl)-4-azabicyclo[5.3.1]undecane.

Compounds resulting from substitution of $NCH_3$ for NH in any of the azabicyclic moieties in the foregoing representative compounds are also representative compounds of the present invention. In each of these compounds, individual stereoisomers thereof, mixtures thereof, including racemic mixtures, enantiomers, diastereomers, and tautomers thereof, and the pharmaceutically acceptable salts thereof, are intended to be within the scope of the present invention.

II. Methods of Preparing the Compounds

As illustrated in Scheme 1, compounds of the present invention are readily prepared by the Suzuki coupling (Oh-e et al., *J. Org. Chem.* 58: 2201 (1993); Lepifre et al., *Tetrahedron Lett.* 40(35): 6373 (1999)) of an appropriate heteroarylboronic acid (or ester) with a N-protected azabicyclic enol triflate (i.e., trifluoromethanesulfonate) or enol phosphate. The enol triflate or phosphate is, in turn, generated from the corresponding azabicyclic ketone, using various methods known to those skilled in the art of organic synthesis. For instance, treatment of the ketone with lithium diisopropylamide (LDA) generates the corresponding enolate, which can be reacted with any of various trifluoromethanesulfonating reagents, such as N-phenyltrifluoromethanesulfonimide or 2-(N,N-bis (trifluoromethanesulfonyl)amino-5-chloropyridine, to give the enol triflate. Likewise, treatment of the enolate with diphenyl chlorophosphate will give the corresponding enol phosphate (Nan and Yang, *Tetrahedron Lett.* 40(17): 3321 (1999)). Alternatively, the ketone can be treated with trifluoromethanesulfonic anhydride and 2,6-lutidine to generate the enol triflate. Typical Suzuki coupling conditions employ palladium tetrakis(triphenylphosphine), sodium carbonate, and lithium chloride in a mixture of water and dimethoxyethane. The corresponding nickel catalyzed reaction has been reported for enol phosphate substrates (Nan and Yang, *Tetrahedron Lett.* 40(17): 3321 (1999)).

In an alternative approach to coupling the heteroaryl group to the azabicycle (also shown in Scheme 1), the N-protected azabicyclic ketone can be reacted with a heteroaryl organometallic reagent (e.g., 3-lithiopyridine) to give a tertiary alcohol. Various methods of converting the alcohol into the alkene, either through the intermediacy of a halide derivative or not, can be employed. Such dehydration and dehydrohalogenation reactions are numerous and well known to those skilled in the art of organic synthesis.

In yet another approach to coupling the heteroaryl group to the azabicycle, a heteroaryl organometallic reagent (e.g., 3-pyridinyllithium or 3-pyridinylmagnesium bromide) can be reacted with certain azabicycloalkene precursors, particularly those in which there is an unsaturated, electron-withdrawing group (CN, —NO$_2$, —C(=O)NR'R", —C(=O)R', —C(=O)OR', —SO$_2$R', —SO$_2$NR'R") attached to one of the double bond carbons. Such systems (known to those skilled in the art as Michael acceptors) add nucleophilic reagents in a "conjugate" or "1,4" manner, such that the new bond is formed between aryl group and the double bond carbon which is in the "beta" position to the electron-withdrawing group. Such conjugate addition reactions are often catalyzed by transition metal salts (e.g., cuprous salts). In this case, the product of such a reaction is a compound of Formula 2, in which the electron-withdrawing group (substituent Z, in the formula) is attached to the azabicycle at the carbon adjacent to the one bearing the heteroaryl group. Properly chosen electron-withdrawing groups can be used to generate a double bond in conjugation with the heteroaryl group, thus producing a compound of Formula 1.

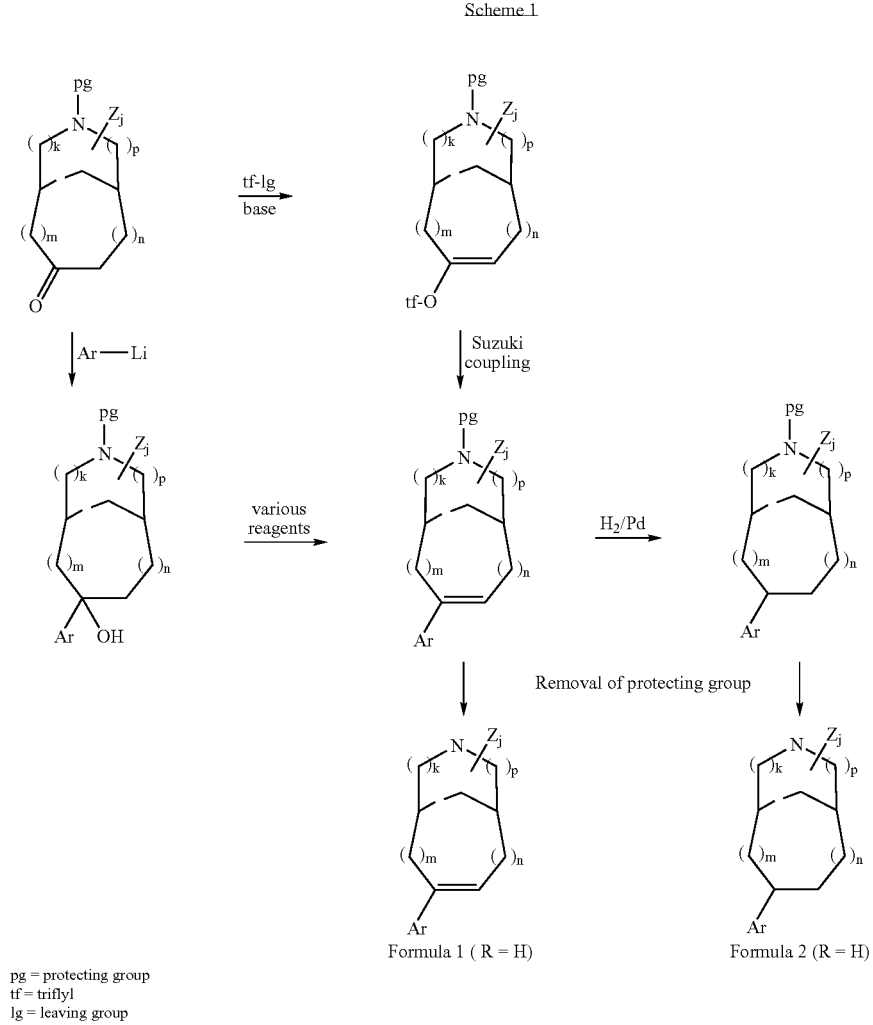

Scheme 1 pg = protecting group
tf = triflyl
lg = leaving group

The protecting groups employed are typically carbamates or amides, either of which may be removed by methods known to those skilled in the art (see Greene and Wuts, Protective Groups in Organic Synthesis 2$^{nd}$ ed., Wiley-Interscience Pub. (1991). Hydrogenation of the alkene can be performed before (or after) removal of the protecting group. Thus, compounds of both Formulas 1 and 2 are produced. Further elaboration of these materials can be accomplished, for instance by alkylating the secondary amine to give a tertiary amine. Thus, treatment of the secondary amine with formic acid and aqueous formaldehyde generates the corresponding N-methyl derivative. Similarly, treatment of the secondary amine with benzaldehyde and sodium cyanoborohydride generates the N-benzyl derivative. Various other techniques for accomplishing alkylations are known to those skilled in the art, such that a variety of alkyl and substituted alkyl groups can be installed at the nitrogen atom of the azabicycle.

The heteroarylboronic acids or esters required for Suzuki coupling are either commercially available or can be prepared by a number of methods known to those skilled in the art of organic synthesis. For instance, halogen-metal exchange of a heteroaromatic halide with an alkyllithium (such as n-butyllithium), and quenching the resulting heteroaryllithium with a borate ester produces the heteroarylboronic acid or ester (depending on reaction work-up conditions). Alternatively, a heteroaromatic halide can be treated with pinacolatoborane in the presence of a palladium catalyst to afford the pinacololboronic ester (Ishiyama et al., *J. Org. Chem.* 60: 7508 (1995); Murata et al., *J. Org. Chem.* 65: 164 (2000)).

It will be obvious to those skilled in the art that it may be desirable to obtain the compounds of the present invention in enantiomerically pure form. This can be achieved by introduction of a chiral auxiliary into the substrate. For example, derivatization of the secondary nitrogen, of a racemic compound of the Formula 1 or 2, with an enantiomerically pure carbamate or amide protecting group will generate a pair of diastereomeric compounds. The separation of these diastereomeric intermediates is typically achieved by crystallization or chromatography, affording the pure enantiomers when the chiral auxiliary is removed at a later stage.

Specific Ring Systems

The compounds according to Formulas 1 and 2, wherein k=n=0 and m=p=1, and the isomeric compounds according to Formulas 1 and 2, wherein k=m=1 and n=p=0, possess the 6-azabicyclo[3.2.1]octane core and are prepared from the same azabicyclic ketone intermediate, 6-azabicyclo[3.2.1]octan-3-one. Syntheses of various N-protected derivatives of this ketone have been reported (Carroll et al., *J. Chem. Soc. Perkin Trans.* I, 1375 (1991); Trost and Genet, *J. Am. Chem. Soc.* 98: 8516 (1976); Gensler et al., *J. Org. Chem.* 33: 2968 (1968); Furstoss et al., *J. Chem. Soc. Chem. Comm.* 30: 805 (1970); Winkler et al., *J. Am. Chem. Soc.* 123: 7429 (2001); Asaoka et al., *Heterocycles* 38: 2455 (1994); and Huffman et al., *J. Org. Chem.* 32: 697 (1967)). Most conveniently, the procedure of Carroll is employed (Scheme 2). Thus, iodolactonization of 3-cyclohexenecarboxylic acid and subsequent base-induced elimination gives the unsaturated lactone. Opening of the lactone with benzylamine affords the amide, which is reduced to the amino alcohol with lithium aluminum hydride. Oxidation of the allylic alcohol functionality with manganese dioxide gives directly the bicyclic product of an intramolecular Michael addition. It was found to be advantageous to exchange the benzyl protecting group for a carbamate, for example, t-butyl carbamate. This is accomplished by chloroformate dealkylation and subsequent reaction of the secondary amine with di-t-butyl dicarbonate. Thus prepared, the N-(t-butoxycarbonyl)-6-azabicyclo[3.2.1]octan-3-one is converted by previously described methods (enol triflate formation and Suzuki coupling) into compounds of the present invention. In this case, two isomeric enol triflates (and therefore, two isomeric Suzuki products) are formed, representing the two positional isomers of the double bond with respect to the nitrogen containing bridge. These are separable chromatographically.

Scheme 2

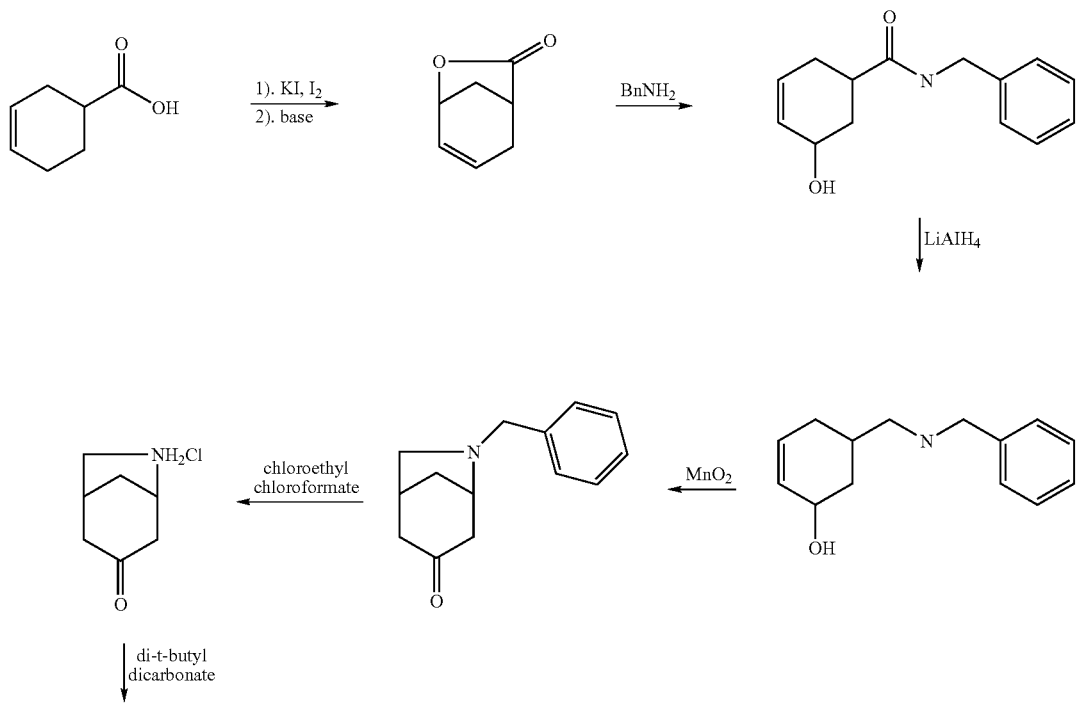

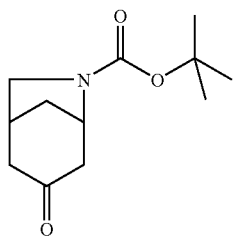

Bn = benzyl

The compounds according to Formulas 1 and 2, wherein k=m=0 and n=p=1, also possess the 6-azabicyclo[3.2.1]octane core, but are isomeric with the previous examples by virtue of the attachment between the azabicycle and the heteroaryl group. The ketone intermediate, N-protected 6-azabicyclo[3.2.1]octan-4-one, is prepared from the hydroxycyclohexenecarboxamide intermediate described in Scheme 2. Thus, as shown in Scheme 3, treatment of this intermediate with thionyl chloride or methanesulfonyl chloride converts the allylic alcohol into the allylic chloride or mesylate. Intramolecular alkylation is then achieved by treatment with a base (such as potassium t-butoxide), providing the desired 7-oxo-6-azabicyclo[3.2.1] oct-3-ene. Conversion of the alkene to the epoxide, followed by reduction of both the lactam and epoxide functionalities with lithium aluminum hydride provides N-benzyl-6-azabicyclo[3.2.1]octan-4-ol. Removal of the benzylic protecting group by hydrogenation with palladium on charcoal in the presence of di-t-butyl dicarbonate gave the t-butyl carbamate. Oxidation of the hydroxyl group is accomplished by either a chromium (VI) based oxidant or Swern conditions, to give the corresponding 6-azabicyclo[3.2.1]octan-4-one. This ketone is transformed, by methods previously described, into compounds of Formulas 1 and 2. For methods of producing other similar 6-azabicyclo[3.2.1]octane intermediates, useful in the synthesis of compounds of the present invention, see Weinreb et al., *Tet. Lett.* 41: 2333 (2000); Mazzocchi et al., *J. Org. Chem.* 46: 4530 (1981); Krow et al., *Syn. Comm.* 13: 575 (1983); Kuehne and Horne, *J. Org. Chem.* 40: 1287 (1974); and Waegell et al., *J. Org. Chem.* 43: 3746 (1978).

Scheme 3

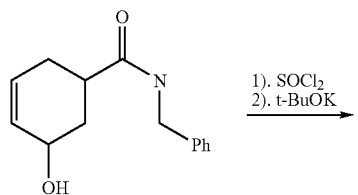

1). SOCl₂
2). t-BuOK

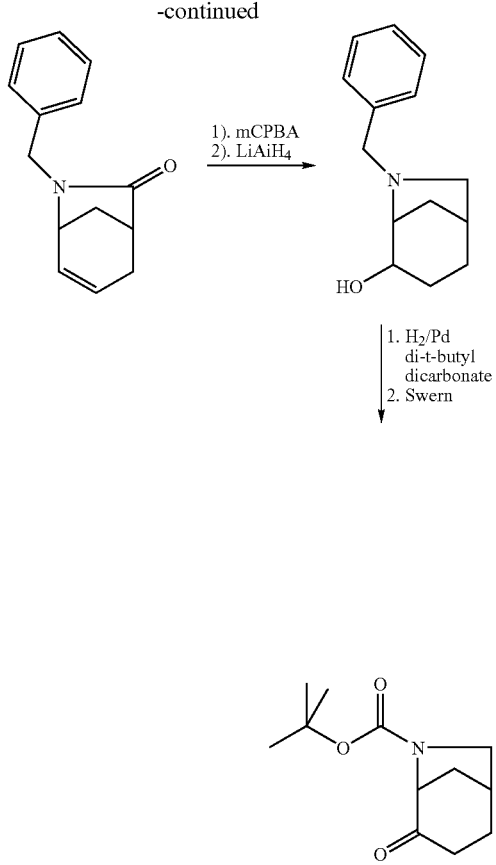

mCPBA = m-chloroperoxybenzoic acid

Compounds according to Formulas 1 and 2, wherein k=m=p=1 and n=0, possess the 3-azabicyclo[3.3.1]nonane core. The ketone intermediate, N-protected 3-azabicyclo[3.3.1]nonan-7-one, is known (Bok and Speckamp, *Tetrahedron* 35: 267 (1979)) and is conveniently prepared using the sequence illustrated in Scheme 4. Birch reduction of 5-methoxyisophthalic acid or 5-aminoisophthalic acid, followed by acidic hydrolysis of the resulting intermediates gives the saturated cyclohexanone-3,5-cisdicarboxylic acid. Esterification and protection of the ketone carbonyl as the ketal is followed by reduction to the diol. Mesylation, and treatment with ammonium hydroxide, results in formation of the bicyclic amine. Protection of the secondary amine as the ethyl carbamate and acidic deprotection of the ketal gives the desired ketone. This is converted into compounds of the present invention using methods already described.

Scheme 4

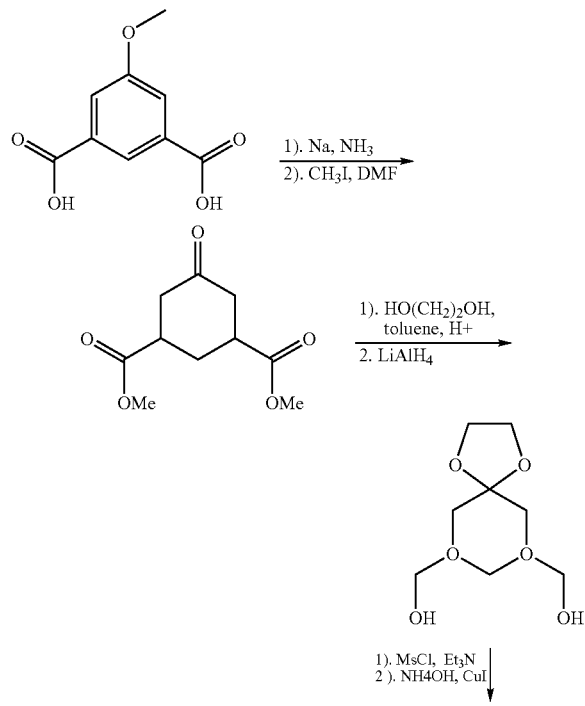

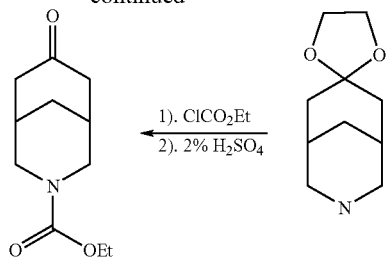

Preparation of compounds according to Formula 1 and 2, wherein k=p=1 and m=n=0, possess the 3-azabicyclo[3.2.1] octane core, and the synthesis of a ketone intermediate, 3-azabicyclo[3.2.1]octan-6-one, is shown in Scheme 5. Thus, Diels-Alder reaction of 2-chloroacrylonitrile and cyclopentadiene affords an adduct, which is then hydrolyzed under basic conditions and subjected to steam distillation to give the bicyclo [2.2.1]hept-5-en-2-one (Freeman et al., *J. Org. Chem.* 33: 2211 (1968); Greene et al., *J. Am. Chem. Soc.* 104: 5473 (1982)). Protection of the carbonyl group as the ketal, followed by ozonolytic cleavage and immediate reduction of the resulting dialdehyde gives the diol. Conversion of the diol into the bis-mesylate, followed by displacement with ammonia, then produces the desired azabicycle. Protection of the nitrogen as the ethyl carbamate and acidic cleavage of the ketal gives 3-azabicyclo[3.2.1]octan-6-one. This is converted into compounds of the present invention using methods already described.

Scheme 5

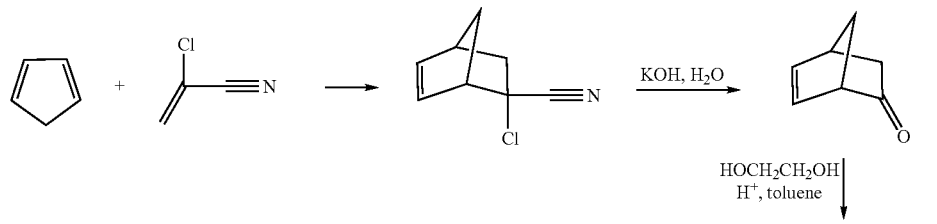

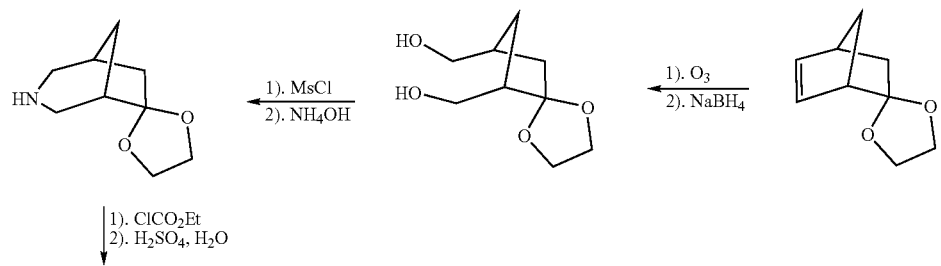

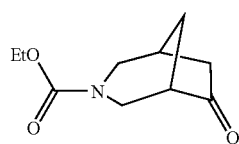

A variety of other azabicyclic ketones can be intermediates for the synthesis of compounds of the present invention. One example of such a ketone is 3-azabicyclo[3.3.1]nonan-6-one, which can be made according to one of the following literature methods: Oppolzer, *Tetrahedron* 41 (17): 3447 (1985); Speckamp et al., *Heterocycles* 12 (3): 343 (1979); Johnson et al., *J. Org. Chem.* 33: 3195 (1968) or Johnson et al., *J. Org. Chem.* 34: 3834 (1969). Another example of such a ketone is 6-azabicyclo[3.2.1]octan-2-one, which can be prepared according to the method of Bonjoch et al., *Tetrahedron: Asymmetry* 10(12): 2399 (1999). Another example is 2-azabicyclo[3.2.1]octan-7-one, which can be made by the method of Ikeda et al., *Heterocycles* 54(2): 747 (2001). Another example is 2-azabicyclo[3.3.1]nonan-6-one, which can be made by the method of Boger et al., *Tet. Lett.* 23(44): 4559 (1982).

III. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more compounds of Formulas 1 or 2 and/or pharmaceutically acceptable salts thereof. Chiral compounds can be employed as racemic mixtures or as pure enantiomers.

In one embodiment, the compounds described herein can be incorporated into pharmaceutical compositions and used to bring about smoking cessation, treat drug addiction, or treat or prevent obesity. In this embodiment, upon administration, the active ingredients interact with receptor sites within the body of the subject that control dopamine release.

In this embodiment, the ability of compounds to partially inhibit the release of dopamine is especially significant, as it indicates that the compounds can be useful in interrupting the dopamine reward system, and thus in treating disorders that are mediated by it. Such disorders include substance abuse, tobacco use and weight gain.

Thus, in this embodiment, the compounds are a useful alternative in treating dependencies on drugs of abuse including alcohol, amphetamines, barbiturates, benzodiazepines, caffeine, cannabinoids, cocaine, hallucinogens, opiates, phencyclidine and tobacco and the treatment of eating disorders, such as obesity that occurs following drug cessation, while reducing side effects associated with the use of psychomotor stimulants (agitation, sleeplessness, addiction, etc.).

In this embodiment, the compounds also advantageously affect the functioning of the CNS, in a manner which is designed to optimize the effect upon those relevant receptor subtypes that have an effect upon dopamine release, while minimizing the effects upon muscle-type receptor subtypes.

In certain circumstances, the compounds can be used as part of a pharmaceutical composition with other compounds intended to prevent or treat drug addiction, nicotine addiction, and/or obesity. In addition to effective amounts of the compounds described herein, the pharmaceutical compositions can also include various other components as additives or adjuncts. Exemplary pharmaceutically acceptable components or adjuncts which are employed in relevant circumstances include antidepressants, antioxidants, free-radical scavenging agents, peptides, growth factors, antibiotics, bacteriostatic agents, immunosuppressives, anticoagulants, buffering agents, anti-inflammatory agents, anti-pyretics, time-release binders, anaesthetics, steroids, vitamins, minerals and corticosteroids. Such components can provide additional therapeutic benefit, act to affect the therapeutic action of the pharmaceutical composition, or act towards preventing any potential side effects which can be imposed as a result of administration of the pharmaceutical composition.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions can be formulated in unit dose form, or in multiple or subunit doses. Preferred compositions are in liquid or semisolid form. Compositions including a liquid pharmaceutically inert carrier such as water or other pharmaceutically compatible liquids or semisolids can be used. The use of such liquids and semisolids is well known to those of skill in the art.

The compositions can also be administered via injection, i.e., intravenously, intramuscularly, subcutaneously, intraperitoneally, intraarterially, intrathecally; and intracerebroventricularly. Intravenous administration is the preferred method of injection. Suitable carriers for injection are well known to those of skill in the art and include 5% dextrose solutions, saline, and phosphate-buffered saline. The compounds can also be administered as an infusion or injection (e.g., as a suspension or as an emulsion in a pharmaceutically acceptable liquid or mixture of liquids).

The formulations can also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations can depend on the particular composition used and the particular subject receiving the treatment. These formulations can contain a liquid carrier that can be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, upon administration, the active ingredients interact with receptor sites within the body of the subject that affect the functioning of the CNS. More specifically, in treating a CNS disorder, preferable administration is designed to optimize the effect upon those relevant nicotinic acetylcholine receptor (nAChR) subtypes that have an effect upon the functioning of the CNS, while minimizing the effects upon muscle-type receptor subtypes. Other suitable methods for administering the compounds of the present invention are described in U.S. Pat. No. 5,604,231 to Smith et al., the contents of which are hereby incorporated by reference.

In certain circumstances, the compounds described herein can be employed as part of a pharmaceutical composition with other compounds intended to prevent or treat a particular disorder. In addition to effective amounts of the compounds described herein, the pharmaceutical compositions can also include various other components as additives or adjuncts. Exemplary pharmaceutically acceptable components or adjuncts which are employed in relevant circumstances include antioxidants, free-radical scavenging agents, peptides, growth factors, antibiotics, bacteriostatic agents, immunosuppressives, anticoagulants, buffering agents, anti-inflammatory agents, anti-pyretics, time-release binders, anesthetics, steroids, vitamins, minerals, and corticosteroids. Such components can provide additional therapeutic benefit, act to affect the therapeutic action of the pharmaceutical composition, or act towards preventing any potential side effects that can be imposed as a result of administration of the pharmaceutical composition.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating a CNS disorder, an effective amount of compound is an amount sufficient to pass across the blood-brain barrier of the subject, to bind to relevant receptor sites in the brain of the subject and to modulate the activity of relevant nAChR subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder. Preferably, the effective amount is sufficient to obtain the desired result, but insufficient to cause appreciable side effects.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate the activity of relevant CNS nAChRs (e.g., to effect neurotransmitter release), but the amount should be insufficient to induce effects on skeletal muscles and ganglia to any significant degree. The effective dose of compounds will of course differ from patient to patient, but in general includes amounts starting where CNS effects or other desired therapeutic effects occur but below the amount where muscular effects are observed.

For use in treating drug addiction, nicotine addiction and/or obesity, the effective dose of typical compounds generally requires administering the compound in an amount sufficient to decrease dopamine release, but the amount should be insufficient to induce effects on skeletal muscles and ganglia to any significant degree. A particular dose of compound effective in preventing and/or treating drug addiction, nicotine addiction and/or obesity (primarily but not necessarily the obesity associated drug or nicotine cessation) is essentially ineffective in eliciting activation of certain ganglionic-type nicotinic receptors at concentration higher than 5 times, preferably higher than 100 times, and more preferably higher than 1,000 times than those required for suppression of dopamine production and/or release. This selectivity of certain compounds described herein against those ganglionic-type receptors responsible for cardiovascular side effects is demonstrated by a lack of the ability of those compounds to activate nicotinic function of adrenal chromaffin tissue at concentrations greater than those required for suppression of dopamine production and/or release.

The compounds, when employed in effective amounts in accordance with the method described herein, are selective to certain relevant nAChRs, but do not interact significantly with receptors associated with undesirable side effects at concentrations at least greater than those required for modulating the release of dopamine or other neurotransmitters. By this is meant, for instance, that a particular dose of compound effective in preventing and/or treating a CNS disorder is substantially ineffective in eliciting activation of certain ganglionic-type nAChRs at concentration higher than 5 times, preferably higher than 100 times, and more preferably higher than 1,000 times than those required for modulation of neurotransmitter release. This selectivity of certain compounds described herein against those ganglionic-type receptors responsible for cardiovascular side effects is demonstrated by a lack of the ability of those compounds to activate nicotinic function of adrenal chromaffin tissue at concentrations greater than those required for modulation of dopamine release.

The compounds described herein, when employed in effective amounts in accordance with the methods described herein, can provide some degree of prevention of the progression of CNS disorders, ameliorate symptoms of CNS disorders, and ameliorate to some degree of the recurrence of CNS disorders. The effective amounts of those compounds are typically below the threshold concentration required to elicit any appreciable side effects, for example those effects relating to skeletal muscle. The compounds can be administered in a therapeutic window in which certain CNS disorders are treated and certain side effects are avoided. Ideally, the effective dose of the compounds described herein is sufficient to provide the desired effects upon the CNS but is insufficient (i.e., is not at a high enough level) to provide undesirable side effects. Preferably, the compounds are administered at a dosage effective for treating the CNS disorders but less than ⅕, and often less than ¹/₁₀, the amount required to elicit certain side effects to any significant degree.

Most preferably, effective doses are at very low concentrations, where maximal effects are observed to occur, with a minimum of side effects. Typically, the effective dose of such compounds generally requires administering the compound in an amount of less than 5 mg/kg of patient weight. Often, the compounds of the present invention are administered in an amount from less than about 1 mg/kg patent weight and usually less than about 100 µg/kg of patient weight, but frequently between about 10 µg to less than 100 µg/kg of patient weight. For compounds that do not induce effects on muscle-type nicotinic receptors at low concentrations, the effective dose is less than 5 mg/kg of patient weight; and often such compounds are administered in an amount from 50 µg to less than 5 mg/kg of patient weight. The foregoing effective doses typically represent that amount administered as a single dose, or as one or more doses administered over a 24-hour period.

For human patients, the effective dose of typical compounds generally requires administering the compound in an amount of at least about 1, often at least about 10, and frequently at least about 25 µg/24 hr/patient. For human patients, the effective dose of typical compounds requires administering the compound which generally does not exceed about 500, often does not exceed about 400, and frequently does not exceed about 300 µg/24 hr/patient. In addition, the compositions are advantageously administered at an effective dose such that the concentration of the compound within the plasma of the patient normally does not exceed 500 pg/ml, often does not exceed 300 pg/ml, and frequently does not exceed 100 pg/ml.

IV. Methods of Using the Compounds and/or Pharmaceutical Compositions

The compounds can be used to treat those types of conditions and disorders for which other types of nicotinic compounds have been proposed as therapeutics. See, for example, Williams et al., *Drug News Perspec.* 7(4):205 (1994), Arneric et al., *CNS Drug Rev.* 1 (1):1 (1995), Arneric et al., *Exp. Opin. Invest. Drugs* 5(1):79 (1996), Bencherif et al., *J. Pharmacol. Exp. Ther.* 279:1413 (1996), Lippiello et al., *J. Pharmacol. Exp. Ther.* 279:1422 (1996), Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); *Neuroscience* (1997), Holladay et al., *J. Med. Chem.* 40(28):4169 (1997), Bannon et al., *Science* 279: 77 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al., the disclosures of each of which are incorporated herein by reference in their entirety.

More particularly, the certain compounds can be used to treat those types of conditions and disorders for which nicotinic compounds with selectivity for the α7 nAChR subtype have been proposed as therapeutics. See, for example, Leonard et al., *Schizophrenia Bulletin* 22(3): 431 (1996), Freedman et al., *Biol. Psychiatry* 38(1): 22 (1995), Heeschen et al., *J. Clin. Invest.* 100: 527 (2002), Utsugisawa et al., *Molecular Brain Research* 106(1-2): 88 (2002), U.S. Patent Application 2002/0016371, Levin and Rezvani, *Current Drug Targets: CNS and Neurological Disorders* 1 (4): 423 (2002)), O'Neill et al., *Current Drug Targets: CNS and Neurological Disorders* 1(4): 399 (2002, Jeyarasasingam et al., *Neuroscience* 109(2): 275 (2002)), Xiao et al., *Proc. Nat. Acad. Sci. (US)* 99(12): 8360 (2002)), PCT WO 99/62505, PCT WO 99/03859, PCT WO 97/30998, PCT WO 01/36417, PCT WO 02/15662, PCT WO 02/16355, PCT WO 02/16356, PCT WO 02/16357, PCT WO 02/16358, PCT WO 02/17358, Stevens et al., *Psychopharm.* 136: 320 (1998), Dolle et al., *J. Labelled Comp. Radiopharm.* 44: 785 (2001) and Macor et al., *Bioorg. Med. Chem. Lett.* 11: 319 (2001) and references therein, the contents of each of which are hereby incorporated by reference in their entirety.

The compounds can also be used as adjunct therapy in combination with existing therapies in the management of the aforementioned types of diseases and disorders. In such situations, it is preferably to administer the active ingredients in a manner that minimizes effects upon nAChR subtypes such as those that are associated with muscle and ganglia. This can be accomplished by targeted drug delivery and/or by adjusting the dosage such that a desired effect is obtained without meeting the threshold dosage required to achieve significant side effects. The pharmaceutical compositions can be used to ameliorate any of the symptoms associated with those conditions, diseases, and disorders. Representative classes of disorders that can be treated are discussed in detail below.

Treatment of CNS Disorders

Examples of conditions and disorders that can be treated include neurological disorders and neurodegenerative disorders, and, in particular, CNS disorders. CNS disorders can be drug induced; can be attributed to genetic predisposition, infection or trauma; or can be of unknown etiology. CNS disorders comprise neuropsychiatric disorders, neurological diseases, and mental illnesses, and include neurodegenerative diseases, behavioral disorders, cognitive disorders, and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin.

Examples of CNS disorders that can be treated in accordance with the present invention include pre-senile dementia (early onset Alzheimer's disease), senile dementia (dementia of the Alzheimer's type), Lewy Body dementia, micro-infarct dementia, AIDS-related dementia, HIV-dementia, multiple cerebral infarcts, Parkinsonism including Parkinson's disease, Pick's disease, progressive supranuclear palsy, Huntington's chorea, tardive dyskinesia, hyperkinesia, mania, attention deficit disorder, anxiety, depression, dyslexia, schizophrenia, obsessive-compulsive disorders, Tourette's syndrome, mild cognitive impairment (MCI), age-associated memory impairment (AAMI), premature amnesic, and cognitive disorders which are age-related or a consequence of alcoholism, or immunodeficiency syndrome, or are associated with vascular disorders, with genetic alterations (such as, for example, trisomy 21) or with attention deficiencies or learning deficiencies, acute or chronic neurodegenerative conditions such as amyotrophic lateral sclerosis, multiple sclerosis, peripheral neurotrophies, and cerebral or spinal traumas. In addition, the compounds can be used to treat nicotine addiction and/or other behavioral disorders related to substances that lead to dependency (e.g., alcohol, cocaine, heroin and other opiates, psychostimulants, benzodiazepines, and barbiturates).

Schizophrenia is an example of a CNS disorder that is particularly amenable to treatment by modulating the (7 nAChR subtype. The compounds can also be administered to improve cognition and/or provide neuroprotection, and these uses are also particularly amenable to treatment with compounds, such as those compounds of the present invention that are specific for the (7 nAChR subtype.

Schizophrenic patients suffer from positive symptoms (hallucination) and negative symptoms (depression and cognitive deficiency). With respect to treatment of schizophrenia, modulation of the α7 receptor tends to be more important than modulation of the α4β2 receptor with respect to treating hallucination. However, modulation of the α4β2 receptor is useful for treating the negative symptoms associated schizophrenia (as well as those aggravated with conventional anti-schizophrenia compounds), such as mood alteration, attention deficit and cognitive deficiency.

Those compounds that bind to both receptors (or mixtures of compounds, where one binds to the α7 receptor and another binds to the α4β2 receptor) can be used to not only treat the positive and negative symptoms of schizophrenia, but also common side effects associated with conventional anti-schizophrenia treatments. The compounds can also provide a neuroprotective effect to these patients.

The disorders can be treated and/or prevented by administering to a patient in need of treatment or prevention thereof an effective treatment or preventative amount of a compound that provides some degree of prevention of the progression of a CNS disorder (i.e., provides protective effects), ameliorating the symptoms of the disorder, and ameliorating the recurrence of the disorder.

Anti-Inflammatory Uses

Excessive inflammation and tumor necrosis factor synthesis cause morbidity and even mortality in a variety of diseases. These diseases include, but are not limited to, endotoxemia, sepsis, rheumatoid arthritis, and irritable bowel disease. The nervous system, primarily through the vagus nerve, is known to regulate the magnitude of the innate immune response by inhibiting the release of macrophage tumor necrosis factor (TNF). This physiological mechanism is known as the "cholinergic anti-inflammatory pathway" (see, for example, Tracey, Nature 420: 853 (2002)).

The nicotinic acetylcholine receptor (7 subunit is required for acetylcholine inhibition of macrophage TNF release, and also inhibits release of other cytokines. Agonists (or, at elevated dosages, partial agonists) at the (7-specific receptor subtype can inhibit the TNF-modulated inflammatory response. Accordingly, those compounds described herein that are (7 agonists can be used to treat inflammatory disorders characterized by excessive synthesis of TNF (see also Wang et al., Nature 421: 384 (2003)).

Inflammatory conditions that can be treated or prevented by administering the compounds described herein include, but are not limited to, chronic and acute inflammation, psoriasis, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, Crohn's disease, ulcerative colitis, acute cholangitis, aphteous stomatitis, glomerulonephritis, lupus nephritis, thrombosis, and graft vs. host reaction. Fibromyalgia syndrome can also be treated with agonists of the (7 receptor.

Minimizing the Inflammatory Response Associated with Bacterial and/or Viral Infection Many bacterial and/or viral infections are associated with side effects brought on by the formation of toxins, and the body's natural response to the bacteria or virus and/or the toxins. Examples of such bacterial infections include anthrax, botulism, and sepsis. As discussed above, the body's response to infection often involves generating a significant amount of TNF and/or other cytokines. The over-expression of these cytokines can result in significant injury, such as septic shock, endotoxic shock, urosepsis, and toxic shock syndrome.

Cytokine expression is mediated by the (7 nAChR, and can be inhibited by administering agonists or partial agonists of these receptors. Those compounds described herein that are agonists or partial agonists of these receptors can therefore be used to minimize the inflammatory response associated with bacterial infection, as well as viral and fungal infections. Certain of the compounds themselves can also have antimicrobial properties.

These compounds can also be used as adjunct therapy in combination with existing therapies to manage bacterial, viral and fungal infections, such as antibiotics, antivirals and antifungals. Antitoxins can also be used to bind to toxins produced by the infectious agents and allow the bound toxins to pass through the body without generating an inflammatory response. Examples of antitoxins are disclosed, for example, in U.S. Pat. No. 6,310,043 to Bundle et al., incorporated herein by reference. Other agents effective against bacterial and other toxins can be effective and their therapeutic effect can be complimented by co-administration with the compounds described herein.

Analgesic Uses

The compounds can be administered to treat and/or prevent pain, including neurologic, neuropathic and chronic pain. The analgesic activity of compounds described herein can be demonstrated in models of persistent inflammatory pain and of neuropathic pain, performed as described in U.S. Published Patent Application No. 20010056084 A1 to Allgeier et al. (e.g., mechanical hyperalgesia in the complete Freund's adjuvant rat model of inflammatory pain and mechanical hyperalgesia in the mouse partial sciatic nerve ligation model of neuropathic pain).

The analgesic effect is suitable for treating pain of various genesis or etiology, in particular in treating inflammatory pain and associated hyperalgesia, neuropathic pain, and associated hyperalgesia, chronic pain (e.g., severe chronic pain, postoperative pain, and pain associated with various conditions including cancer, angina, renal or billiary colic, menstruation, migraine, and gout). Inflammatory pain can be of diverse genesis, including arthritis and rheumatoid disease, tenosynovitis, and vasculitis. Neuropathic pain includes trigeminal or herpetic neuralgia, diabetic neuropathy pain, causalgia, low back pain, and deafferentation syndromes such as brachial plexus avulsion.

An additional class of pains particularly suited to treatment with the present compounds are injury-related or "nociceptive" pains. Nicotine-induced antinociception appears to be a complex phenomenon that involves multiple nicotinic receptor subtypes depending on the pain type and sites of action. Based on available pharmacological data, however, it is evident that neuronal nAChRs are engaged; specifically, (4(2 neuronal subtypes have been implicated in thermal acute pain tests such as hot-plate (and tail-flick assays (which involves a spinal reflex). The (7 nAChR is also associated with modulating pain transmission in the CNS in a variety of species and pain tests, as shown by studies suggesting that activation of (7 receptors in the CNS elicits antinociceptive effects in an acute thermal pain model. See, for instance, Damaj, M. I., et al., The antinociceptive effects of α7 nicotinic agonists in an acute pain model. *Neuropharmacology* 39:2785-2791 (2000) (the disclosure of which is hereby incorporated herein by reference in its entirety), and references cited therein, which provide guidance regarding appropriate animal models for evaluating the compounds described herein, including an acute thermal pain model in mice.

Additional animal models for evaluating antinociceptive activities of the compounds herein or antinociceptive activity and behavioral effects characteristic of nicotinic ligands with selectivity for neuronal nAChRs are described, for instance, in Bannon, A. W., et al., ABT-594 [(R)-5-(2-azetidinylmethoxy)-2-chloropyridine]: a novel, orally effective antinociceptive agent acting via neuronal nicotinic acetylcholine receptors: II. In vivo characterization. *J. Pharmaco.I Exp. Ther.* 285:787-794 (1998) (the disclosure of which is hereby incorporated herein by reference in its entirety), including: a rat model of acute thermal (hot box) and persistent chemical (formalin test) pain; a rodent model for effects on motor function (to differentiate motor function from analgesic effects) and electroencephalogram (EEG; to detect morphine-like sedating side effects), and the use of opioid receptor antagonists and nAChR antagonists, such as mecamylamine, to show nAChR specificity. Further relevant animal models are described, for instance, in Damaj. M. I., et al., Antinociceptive and pharmacological effects of metanicotine, a selective nicotinic agonist. *J. Pharmacol. Exp. Ther.* 291:390-398 (1999) (the disclosure of which is hereby incorporated herein by reference in its entirety), including the following: rodent models for antinociceptive activity and behavioral effects of nicotinic ligands with selectivity for neuronal nAChRs: acute thermal (mouse tail-flick and hot-plate tests), mechanical (paw-pressure test in rats), and visceral [paraphenylquinone (PPQ)] pain tests; persistent and chronic pain (mouse formalin test and arthritic pain model, respectively); behavioral models (locomotor activity, drug discrimination, and body temperature measurement), for ascertaining nicotinic effects and evaluating a compound as a potential analgesic drug with fewer side effects than those presently available.

While not wishing to be bound to a particular theory, it is believed that some analgesia is associated with the α4β2 receptor, and some analgesia is associated with the α7 receptor. Accordingly, those compounds that bind to both receptors (or a combination of compounds that bind to both receptors) can offer a wider spectrum of analgesia than compounds that only bind to one of these receptors.

Inhibition of Neovascularization

The (7 nAChR is also associated with neovascularization. Inhibition of neovascularization, for example, by administering antagonists (or at certain dosages, partial agonists) of the (7 nAChR can treat or prevent conditions characterized by undesirable neovascularization or angiogenesis. Such conditions can include those characterized by inflammatory angiogenesis and/or ischemia-induced angiogenesis. Neovascularization associated with tumor growth can also be inhibited by administering those compounds described herein that function as antagonists or partial agonists of (7 nAChR.

Specific antagonism of (7 nAChR-specific activity reduces the angiogenic response to inflammation, ischemia, and neoplasia. Guidance regarding appropriate animal model systems for evaluating the compounds described herein can be found, for example, in Heeschen et al., *J. Clin. Invest.* 110(4): 527 (2002), incorporated herein by reference regarding disclosure of (7-specific inhibition of angiogenesis and cellular (in vitro) and animal modeling of angiogenic activity relevant to human disease, especially the Lewis lung tumor model (in vivo, in mice—see, in particular, pages 529, and 532-533).

Representative tumor types that can be treated using the compounds described herein include non-small cell lung cancer (NSCLC), ovarian cancer, pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, urinary tract carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma, tumors of the brain, tumors of the nerves, tumors of the eyes, tumors of the meninges, astrocytomas, gliomas, glioblastomas, retinoblastomas, neuromas, neuroblastomas, Schwannomas, meningiomas, solid tumors arising from hematopoietic malignancies (such as leukemias, chloromas, plasmacytomas, and the plaques and tumors of mycosis fungoides and cutaneous T-cell lymphoma/leukemia), and solid tumors arising from lymphomas.

The compounds can also be administered in conjunction with other forms of anti-cancer treatment, including co-administration with antineoplastic antitumor agents such as cisplatin, adriamycin, daunomycin, and the like, and/or anti-VEGF (vascular endothelial growth factor) agents, as such are known in the art.

The compounds can be administered in such a manner that they are targeted to the tumor site. For example, the compounds can be administered in microspheres, microparticles or liposomes conjugated to various antibodies that direct the microparticles to the tumor. Additionally, the compounds can be present in microspheres, microparticles or liposomes that are appropriately sized to pass through the arteries and veins, but lodge in capillary beds surrounding tumors and administer the compounds locally to the tumor. Such drug delivery devices are known in the art.

Treatment of Drug Addiction, Nicotine Addiction and/or Obesity

The compounds can be used to treat drug addiction, nicotine addiction and/or obesity, such as the obesity associated with drug cessation. The compounds can also be used as adjunct therapy in combination with existing therapies in the management of the aforementioned types of diseases and disorders. In such situations, it is preferable to administer the active ingredients to in a manner that optimizes effects upon dopamine production and/or secretion, while minimizing effects upon receptor subtypes such as those that are associated with muscle and ganglia. This can be accomplished by targeted drug delivery and/or by adjusting the dosage such that a desired effect is obtained without meeting the threshold dosage required to achieve significant side effects.

In this embodiment, the compounds have the ability to bind to, and in most circumstances, antagonize or partially antagonize one or more nicotinic receptors of the brain of the patient that modulate dopamine release, other than the (4(2 receptor, at concentrations at which the (4 (2 receptor is largely unaffected. As such, such compounds have the ability to express nicotinic pharmacology, and in particular, to act as dopamine antagonists.

Accordingly, in this embodiment, the compounds are effective at suppressing of dopamine production and/or release, and can be used to treat drug addiction, nicotine addiction, and/or obesity at effective at concentrations that are not sufficient to elicit any appreciable side effects, as is demonstrated by decreased effects on preparations believed to reflect effects on the cardiovascular system, or effects to skeletal muscle. As such, administration of the compounds provides a therapeutic window in which treatment of drug addiction, nicotine addiction and/or obesity is effected, and side effects are avoided. That is, an effective dose of a compound of the present invention is sufficient to provide the desired antagonistic effects on dopamine production and/or secretion, but is insufficient (i.e., is not at a high enough level) to provide undesirable side effects. Preferably, the compounds results in treatment of drug addiction, nicotine addiction and/or obesity upon administration of less ⅓, frequently less than ⅕, and often less than 1/10, that amount sufficient to cause any side effects to a significant degree.

Other Disorders

In addition to treating CNS disorders, inflammatory disorders, and neovascular disorders, and inhibiting the pain response, the compounds can be also used to prevent or treat certain other conditions, diseases, and disorders. Examples include autoimmune disorders such as Lupus, disorders associated with cytokine release, cachexia secondary to infection (e.g., as occurs in AIDS, AIDS related complex and neoplasia), as well as those indications set forth in PCT WO 98/25619. The compounds can also be administered to treat convulsions such as those that are symptomatic of epilepsy, and to treat conditions such as syphilis and Creutzfeld-Jakob disease.

Diagnostic Uses

The compounds can be used in diagnostic compositions, such as probes, particularly when they are modified to include appropriate labels. The probes can be used, for example, to determine the relative number and/or function of specific receptors, particularly the α4β2 or α7 receptor subtypes. The compounds of the present invention most preferably are labeled with a radioactive isotopic moiety such as $^{11}C$, $^{18}F$, $^{76}Br$, $^{123}I$ or $^{125}I$, as discussed in PCT WO 01/82979 to Bencherif et al.

The administered compounds can be detected using known detection methods appropriate for the label used. Examples of detection methods include position emission topography (PET) and single-photon emission computed tomography (SPECT). The radiolabels described above are useful in PET (e.g., $^{11}C$, $^{18}F$ or $^{76}Br$) and SPECT (e.g., $^{123}I$) imaging, with half-lives of about 20.4 minutes for $^{11}C$, about 109 minutes for $^{18}F$, about 13 hours for $^{123}I$, and about 16 hours for $^{76}Br$. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al. The compounds can be administered in formulation compositions that incorporate other ingredients, such as those types of ingredients that are useful in formulating a diagnostic composition. Compounds useful in accordance with carrying out the present invention most preferably are employed in forms of high purity. See U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality of selected nicotinic cholinergic receptor subtypes. In addition to humans, the compounds can also be administered to animals, such as mice, rats, dogs, and monkeys. SPECT and PET imaging can be carried out using any appropriate technique and apparatus. See Villemagne et al., In: *Neuronal Nicotinic Receptors: Pharmacology and Therapeutic Opportunities*, Arneric et al. (Eds.), 235-250 (1998) and U.S. Pat. No. 5,853,696 to Elmalch et al. for a disclosure of representative imaging techniques.

The radiolabeled compounds bind with high affinity to selective nAChR subtypes (e.g., α4β2 or α7) and preferably exhibit negligible non-specific binding to other nicotinic cholinergic receptor subtypes (e.g., those receptor subtypes associated with muscle and ganglia). As such, the compounds can be used as agents for noninvasive imaging of nicotinic cholinergic receptor subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labeled compound as described herein, and detecting the binding of that compound to selected nicotinic receptor subtypes (e.g., (7 receptor subtype). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth in U.S. Pat. No. 5,952,339 to Bencherif et al., the contents of which are hereby incorporated by reference.

In another aspect, the diagnostic compositions can be used in a method to monitor selective nicotinic receptor subtypes of a subject, such as a human patient. The method involves administering a detectably labeled compound as described herein to that patient, and detecting the binding of that compound to selected nicotinic receptor subtypes (e.g., the (7 receptor subtype).

The following examples are provided to further illustrate the present invention, and should not be construed as limiting thereof.

V. Biological Assays

Radioligand Binding at CNS nAChR (4(2 Subtype

Rats (female, Sprague-Dawley), weighing 150-250 g, were maintained on a 12 h light/dark cycle and were allowed free access to water and food supplied by PMI Nutrition International, Inc. Animals were anaesthetized with 70% $CO_2$, then decapitated. Brains were removed and placed on an ice-cold platform. The cerebral cortex was removed and placed in 20 volumes (weight: volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the suspension was homogenized by Polytron. The homogenate was centrifuged at 18,000×g for 20 min at 4(C and the resulting pellet was re-suspended in 20 volumes of ice-cold water. After 60 min incubation on ice, a new pellet was collected by centrifugation at 18,000×g for 20 min at 4(C. The final pellet was re-suspended in 10 volumes of buffer and stored at –20(C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 4 mg protein/ml. Protein was determined by the method of Lowry et al., *J. Biol. Chem.* 193:265 (1951), using bovine serum albumin as the standard.

The binding of [$^3H$]nicotine was measured using a modification of the methods of Romano et al., *Science* 210: 647 (1980) and Marks et al., *Mol. Pharmacol.* 30: 427 (1986). The [$^3H$]nicotine (Specific Activity=81.5 Ci/mmol) was obtained from NEN Research Products. The binding of [$^3H$]nicotine was measured using a 3 h incubation at 4(C. Incubations were conducted in 48-well micro-titre plates and contained about 400 (g of protein per well in a final incubation volume of 300 (L. The incubation buffer was PBS and the final concentration of [$^3H$]nicotine was 5 nM. The binding reaction was terminated by filtration of the protein containing bound ligand onto glass fiber filters (GF/B, Brandel) using a Brandel Tissue Harvester at 4(C. Filters were soaked in de-ionized water containing 0.33% polyethyleneimine to reduce non-specific binding. Each filter was washed with ice-cold buffer (3×1 ml).

Non-specific binding was determined by inclusion of 10 (M non-radioactive L-nicotine (Acros Organics) in selected wells.

The inhibition of [$^3$H]nicotine binding by test compounds was determined by including seven different concentrations of the test compound in selected wells. Each concentration was replicated in triplicate. $IC_{50}$ values were estimated as the concentration of compound that inhibited 50 percent of specific [$^3$H]nicotine binding. Inhibition constants (Ki values), reported in nM, were calculated from the $IC_{50}$ values using the method of Cheng et al., *Biochem. Pharmacol.* 22: 3099 (1973).

(7 Subtype

Rats (female, Sprague-Dawley), weighing 150-250 g, were maintained on a 12 h light/dark cycle and were allowed free access to water and food supplied by PMI Nutrition International, Inc. Animals were anaesthetized with 70% $CO_2$, then decapitated. Brains were removed and placed on an ice-cold platform. The hippocampus was removed and placed in 10 volumes (weight: volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 (M, was added and the tissue suspension was homogenized by Polytron. The homogenate was centrifuged at 18,000×g for 20 min at 4(C and the resulting pellet was re-suspended in 10 volumes of ice-cold water. After 60 min incubation on ice, a new pellet was collected by centrifugation at 18,000×g for 20 min at 4(C. The final pellet was re-suspended in 10 volumes of buffer and stored at −20(C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$ 8.1 mM $Na_2HPO_4$, 0.9 mM $CaCl_2$, 0.5 mM $MgCl_2$, Invitrogen/Gibco, pH 7.4) to a final concentration of approximately 2 mg protein/ml. Protein was determined by the method of Lowry et al., *J. Biol. Chem.* 193: 265 (1951), using bovine serum albumin as the standard.

The binding of [$^3$H]MLA was measured using a modification of the methods of Davies et al., *Neuropharmacol.* 38: 679 (1999). [$^3$H]MLA (Specific Activity=25-35 Ci/mmol) was obtained from Tocris. The binding of [$^3$H]MLA was determined using a 2 h incubation at 21(C. Incubations were conducted in 48-well micro-titre plates and contained about 200 μg of protein per well in a final incubation volume of 300 (L. The incubation buffer was PBS and the final concentration of [$^3$H]MLA was 5 nM. The binding reaction was terminated by filtration of the protein containing bound ligand onto glass fiber filters (GF/B, Brandel) using a Brandel Tissue Harvester at room temperature. Filters were soaked in de-ionized water containing 0.33% polyethyleneimine to reduce non-specific binding. Each filter was washed with PBS (3×1 ml) at room temperature. Non-specific binding was determined by inclusion of 50 (M non-radioactive MLA in selected wells.

The inhibition of [$^3$H]MLA binding by test compounds was determined by including seven different concentrations of the test compound in selected wells. Each concentration was replicated in triplicate. $IC_{50}$ values were estimated as the concentration of compound that inhibited 50 percent of specific [$^3$H]MLA binding. Inhibition constants (Ki values), reported in nM, were calculated from the $IC_{50}$ values using the method of Cheng et al., *Biochem. Pharmacol.* 22: 3099-3108 (1973).

Determination of Dopamine Release

Dopamine release was measured using striatal synaptosomes obtained from rat brain, according to the procedures set forth by Rapier et al., *J. Neurochem.* 54: 937 (1990). Rats (female, Sprague-Dawley), weighing 150-250 g, were maintained on a 12 h light/dark cycle and were allowed free access to water and food supplied by PMI Nutrition International, Inc. Animals were anaesthetized with 70% $CO_2$, then decapitated. The brains were quickly removed and the striata dissected. Striatal tissue from each of 2 rats was pooled and homogenized in ice-cold 0.32 M sucrose (5 ml) containing 5 mM HEPES, pH 7.4, using a glass/glass homogenizer. The tissue was then centrifuged at 1,000×g for 10 min. The pellet was discarded and the supernatant was centrifuged at 12,000×g for 20 min. The resulting pellet was re-suspended in perfusion buffer containing monoamine oxidase inhibitors (128 mM NaCl, 1.2 mM $KH_2PO_4$, 2.4 mM KCl, 3.2 mM $CaCl_2$, 1.2 mM $MgSO_4$, 25 mM HEPES, 1 mM ascorbic acid, 0.02 mM pargyline HCl and 10 mM glucose, pH 7.4) and centrifuged for 15 min at 25,000×g. The final pellet was resuspended in perfusion buffer (1.4 ml) for immediate use.

The synaptosomal suspension was incubated for 10 min at 37° C. to restore metabolic activity. [$^3$H]Dopamine ([$^3$H]DA, specific activity=28.0 Ci/mmol, NEN Research Products) was added at a final concentration of 0.1 μM and the suspension was incubated at 37° C. for another 10 min. Aliquots of tissue (50 μl) and perfusion buffer (100 μl) were loaded into the suprafusion chambers of a Brandel Suprafusion System (series 2500, Gaithersburg, Md.). Perfusion buffer (room temperature) was pumped into the chambers at a rate of 3 ml/min for a wash period of 8 min. Test compound (10 μM) or nicotine (10 μM) was then applied in the perfusion stream for 40 sec. Fractions (12 sec each) were continuously collected from each chamber throughout the experiment to capture basal release and agonist-induced peak release and to re-establish the baseline after the agonist application. The perfusate was collected directly into scintillation vials, to which scintillation fluid was added. [$^3$H]DA released was quantified by scintillation counting. For each chamber, the integrated area of the peak was normalized to its baseline.

Release was expressed as a percentage of release obtained with an equal concentration of L-nicotine. Within each assay, each test compound was replicated using 2-3 chambers; replicates were averaged. When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

Antagonism of dopamine release can also be evaluated using the assays described in Grady et al., "Characterization of nicotinic receptor mediated [3H]dopamine release from synaptosomes prepared from mouse striatum," *J. Neurochem.* 59: 848-856 (1992) and Soliakov and Wonnacott, "Voltage-sensitive $Ca^{2+}$ channels involved in nicotinic receptor-mediated [3H]dopamine release from rat striatal synaptosomes," *J. Neurochem.* 67:163-170 (1996).

Selectivity vs. Peripheral nAChRs

Interaction at the Human Muscle Subtype

Activation of muscle-type nAChR was established on the human clonal line TE671/RD, which is derived from an embryonal rhabdomyosarcoma (Stratton et al., *Carcinogen* 10: 899 (1989)). These cells express receptors that have pharmacological (Lukas, *J. Pharmacol. Exp. Ther.* 251: 175 (1989)), electrophysiological (Oswald et al., *Neurosci Lett.* 96: 207 (1989)), and molecular biological profiles (Luther et al., *J. Neurosci.* 9: 1082 (1989)) similar to the muscle-type nAChR.

TE671/RD cells were maintained in proliferative growth phase according to routine protocols (Bencherif et al., *Mol. Cell. Neurosci.* 2: 52 (1991) and Bencherif et al., *J. Pharma-*

*col. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}Rb^+$ efflux according to the method described by Lukas et al., *Anal. Biochem.* 175: 212 (1988). On the day of the experiment, growth media was gently removed from the well and growth media containing $^{86}Rubidium$ chloride ($10^6$ µCi/ml) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells were exposed to either 100 µM of test compound, 100 µM of L-nicotine (Acros Organics) or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 µM L-nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Rat Ganglionic Subtype

Activation of rat ganglion nAChR was established on the pheochromocytoma clonal line PC12, which is a continuous clonal cell line of neural crest origin, derived from a tumor of the rat adrenal medulla. These cells express ganglion-like neuronal nicotinic receptors (see Whiting et al., *Nature* 327: 515 (1987); Lukas, *J. Pharmacol. Exp. Ther.* 251: 175 (1989); Whiting et al., *Mol. Brain Res.* 10: 61 (1990)).

Rat PC12 cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well Nunc plates (Nunclon) and coated with 0.03% poly-L-lysine (Sigma, dissolved in 100 mM boric acid). Experiments were conducted when the cells reached 80% confluency.

Nicotinic acetylcholine receptor (nAChR) function was assayed using $^{86}Rb^+$ efflux according to a method described by Lukas et al., *Anal. Biochem.* 175: 212 (1988). On the day of the experiment, growth media was gently removed from the well and growth media containing $^{86}Rubidium$ chloride ($10^6$ µCi/ml) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells were exposed to either 100 µM of test compound, 100 µM of nicotine or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 µM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Human Ganglionic Subtype

The cell line SH-SY5Y is a continuous line derived by sequential subcloning of the parental cell line, SK-N-SH, which was originally obtained from a human peripheral neuroblastoma. SH-SY5Y cells express a ganglion-like nAChR (Lukas et al., *Mol. Cell. Neurosci.* 4: 1 (1993)).

Human SH-SY5Y cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}Rb^+$ efflux according to a method described by Lukas et al., *Anal. Biochem.* 175: 212 (1988). On the day of the experiment, growth media was gently removed from the well and growth media containing $^{86}Rubidium$ chloride ($10^6$ µCi/ml) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4), taking care not to disturb the cells. Next, cells were exposed to either 100 µM of test compound, 100 µM of nicotine, or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 µM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

VI. EXAMPLES

The following synthetic examples are provided to illustrate the present invention and should not be construed as limiting the scope thereof. In these examples, all parts and percentages are by weight, unless otherwise noted. Reaction yields are reported in mole percentage.

Example 1

Example No. 1 is the pair of isomers, 3-(3-pyridinyl)-6-azabicyclo [3.2.1]oct-2-ene dihydrochloride and 3-(3-pyridinyl)-6-azabicyclo[3.2.1] oct-3-ene dihydrochloride, which were prepared in accordance with the following techniques:

4-Iodo-6-oxabicyclo[3.2.1]octan-7-one

To a suspension of 3-cyclohexenecarboxylic acid (5.0 g, 40 mmol) in water (200 ml) was added, with vigorous stirring, sodium bicarbonate (9.90 g, 118 mmol). A solution of potassium iodide (39.0 g, 235 mmol) in water (125 ml) was prepared, and to this iodine (10 g, 40 mmol) was added to give a brown solution. This solution was added in one portion to the vigorously stirring solution of cyclohexenecarboxylate. The mixture was stirred at room temperature in the dark for 18 h. The resulting yellow solid was collected by filtration. The damp solid was dissolved in chloroform (150 ml) and washed with sodium thiosulfate solution (2×25 ml), and then with brine (25 ml). It was dried over magnesium sulfate, filtered and concentrated by rotary evaporation to afford iodolactone (8.5 g, 84%, m.p. 133-134(C).

6-Oxabicyclo[3.2.1]oct-3-en-7-one

To 4-iodo-6-oxabicyclo[3.2.1]octan-7-one (8.00 g, 31.7 mmol) in benzene (100 ml) was added 1,8-diazabicyclo [5.4.0]undec-7-ene (7.9 g, 32 mmol) under nitrogen, and the mixture was heated under reflux for 6 h. The white precipitate was filtered off from the cooled solution and washed with ether (100 ml). The combined filtrates were washed with water (50 ml), 1N HCl (50 ml), and brine (25 ml), and then dried over magnesium sulfate. The solvents were removed by rotary evaporation to afford the alkene as a light brown oil (2.6 g, 66%).

N-benzyl-5-hydroxycyclohex-3-enecarboxamide

To 6-oxabicyclo[3.2.1]oct-3-en-7-one (2.6 g, 21 mmol) in xylenes (50 ml) under nitrogen was added benzylamine (3.42 g, 32 mmol). The mixture was heated under reflux for 16 h, then cooled to room temperature. The heavy white precipitate was collected by filtration, and recrystallized from dichloromethane/hexane to give the amide as a white solid (3.8 g, 78%, m.p. 127-128(C).

5-(Benzylaminomethyl)cyclohex-2-enol

To a suspension of lithium aluminum hydride (1.50 g, 40.5 mmol) in dry THF (100 ml), cooled in an ice bath, was added drop-wise a solution of N-benzyl-5-hydroxycyclohex-3-enecarboxamide (4.6 g, 20 mmol) in THF (60 ml) over 30 min. The cold bath was removed and the reaction was heated under reflux for 16 h. Then the mixture was cooled in an ice bath and diluted with ether (200 ml), then carefully quenched with water (1.5 ml), 1N sodium hydroxide (4 ml) and water (1.5 ml), successively. After stirring for 45 min, the white suspension was filtered through a glass frit, and the residue was washed with ether. Removal of solvents by rotary evaporation gave the alcohol as a clear, colorless oil (3.8 g, 88%).

6-Benzyl-6-azabicyclo[3.2.1]octan-3-one

To a solution of 5-(benzylaminomethyl)cyclohex-2-enol (3.80 g, 17.5 mmol) in dry dichloromethane (150 ml) was added activated manganese dioxide (18.0 g, 210 mmol) in one portion. The mixture was stirred vigorously under nitrogen for 2 h. The yellow solution was filtered through Celite and the solids were washed with dichloromethane (2×50 ml). The combined filtrates were concentrated by rotary evaporation to give an orange oil, which solidified on brief standing. The solid was recrystallized from hot hexane/ether to afford the ketone as an off-white solid (2.6 g, 68%).

t-Butyl 3-oxo-6-azabicyclo[3.2.1]octane-6-carboxylate

To a solution of 6-benzyl-6-azabicyclo[3.2.1]octan-3-one (1.2 g, 5.6 mmol) in dry dichloromethane (20 ml), cooled in an ice bath under nitrogen, was added drop-wise chloroethyl chloroformate (Acros, 0.64 ml, 7.2 mmol). The mixture was stirred 10 min at 0(C, then warmed to room temperature and stirred 1.5 h. The mixture was concentrated to dryness by rotary evaporation and the residue was dissolved in methanol (15 ml). The resulting solution was heated under reflux for 2 h, then concentrated to dryness by rotary evaporation and the residue was re-suspended in dry dichloromethane (20 ml). The suspension was cooled in an ice bath, then triethylamine (2.1 ml, 15 mmol) was added, followed by di-t-butyl dicarbonate (1.31 g, 6.01 mmol). The mixture was allowed to warm to room temperature and stir over the weekend (64 h). The reaction mixture was diluted with dichloromethane and washed with water, 1N HCl, water, and brine (10 ml each). The organic layer was dried over magnesium sulfate, filtered, and concentrated by rotary evaporation to give a yellow oil, which solidified on standing to a waxy solid. The product contained minor impurities and was purified by column chromatography, using a hexane/ethyl acetate gradient (0-30% ethyl acetate) as eluent, to give the product as a pale yellow, waxy solid (0.80 g, 63%).

t-Butyl 3-trifluoromethanesulfonyloxy-6-azabicyclo [3.2.1]oct-2-ene-6-carboxylate and t-butyl 3-trifluoromethanesulfonyloxy-6-azabicyclo [3.2.1]oct-3-ene-6-carboxylate To a solution of dry diisopropylamine (0.15 ml, 1.1 mmol) in dry THF (15 ml), cooled to −78(C under nitrogen, was added drop-wise a solution of 2.4 M n-butyllithium in hexane (0.46 ml, 1.1 mmol). After 15 min, a solution of t-butyl 3-oxo-6-azabicyclo[3.2.1]octane-6-carboxylate (225 mg, 1 mmol) in THF (3 ml) was added drop-wise. After stirring 15 min at −78(C, 2-(N,N-bis(trifluoromethylsulfonyl) amino-5-chloropyridine (431 mg, 1.10 mmol) was added in one portion. The reaction was allowed to warm to around 0(C over 1.5 h, at which time it was quenched by addition of a saturated solution of sodium bicarbonate (25 ml). The mixture was extracted with ether (4×15 ml) and the organic extracts combined and washed with 1N HCl, water, saturated sodium bicarbonate solution and brine (10 ml each) and dried over magnesium sulfate. Filtration and concentration by rotary evaporation gave a viscous, orange oil. This was dissolved in chloroform, adsorbed onto 5 g silica gel, dried, and eluted on an ISCO combiflash system (10 g SiO$_2$ column, 20 ml/min flow, 0-50% ethyl acetate/hexane over 20 min). The fractions corresponding to the desired product (higher $R_f$, non-UV active) were pooled and concentrated by rotary evaporation to afford the mixture of enol triflates as a pale yellow oil (260 mg, 73%).

3-(3-Pyridinyl)-6-azabicyclo[3.2.1]oct-2-ene dihydrochloride and 3-(3-pyridinyl)-6-azabicyclo[3.2.1]oct-3-ene dihydrochloride To a solution of the mixture of enol triflates (1.0 g, 2.8 mmol) in dimethoxyethane (20 ml) was added a saturated solution of sodium carbonate (5 ml), lithium chloride (0.42 g, 10 mmol) and 3-pyridinylboronic acid (510 mg, 4.20 mmol). The reaction mixture was filled with nitrogen, then palladium tetrakis(triphenylphosphine) catalyst was added (200 mg). The reaction mixture was stirred vigorously and heated under reflux for 4 h. The dark mixture was filtered through a Celite pad into 50% aqueous ammonium hydroxide solution (25 ml). The mixture was extracted with ethyl acetate (2×25 ml), and then the organics were washed with brine (2×15 ml) and dried over sodium sulfate. Concentration by rotary evaporation gave a dark oil, which was purified by column chromatography, using hexane-ethyl acetate (2:1) as eluent, to afford a brown oil (750 mg). The oil was dissolved in methanol (5 ml) and was treated with 4 N HCl in dioxane (1 ml) at room temperature for 2 h. Removal of solvent by rotary evaporation left a residue, which was dissolved in methanol and treated with ammonium hydroxide, then concentrated by rotary evaporation. The resulting oil was triturated with chloroform and the extract was purified by column chromatography on an ISCO 10 g silica gel column, using a gradient of methanol/dichloromethane (0-10% methanol with 1% ammonium hydroxide) as eluent. This separated the two regioisomers.

The higher $R_f$ fractions were pooled, concentrated, treated with methanolic HCl, and concentrated to give 3-(3-pyridinyl)-6-azabicyclo [3.2.1]oct-2-ene dihydrochloride, (96 mg), m.p.=210-212° C.

The lower $R_f$ fractions were pooled, concentrated, treated with methanolic HCl, and concentrated to give 3-(3-pyridinyl)-6-azabicyclo [3.2.1]oct-3-ene dihydrochloride, (28 mg).

Example 2

Example No. 2 is 3-(3-pyridinyl)-6-azabicyclo[3.2.1]octane, which was prepared in accordance with the following techniques:

3-(3-pyridinyl)-6-azabicyclo[3.2.1]octane

To a solution of a mixture of t-butyl 3-(3-pyridinyl)-6-azabicyclo[3.2.1] oct-2-ene-6-carboxylate and t-butyl 3-(3-pyridinyl)-6-azabicyclo[3.2.1] oct-3-ene-6-carboxylate (150 mg) in methanol (5 ml) was added catalytic 10% Pd/C and the mixture was subjected to hydrogenolysis (45 psi) for 48 h. The reaction was filtered through Celite and concentrated by rotary evaporation, and then the residue was taken up in dichloromethane (1 ml) and treated with trifluoroacetic acid (2 ml). After 3 h, the mixture was concentrated to dryness by rotary evaporation, partitioned between water and dichloromethane, and the organic layer discarded. The aqueous layer was made basic with sodium hydroxide and extracted with dichloromethane. After drying over sodium sulfate, the filtered solution was concentrated to dryness by rotary evaporation and the residue purified by column chromatography, using a methanol/dichloromethane gradient (0-10% methanol with 1% ammonium hydroxide) as eluent. The product fractions were pooled and concentrated to give the desired product (20 mg). It was then re-chromatographed (same conditions) to give the free base (10 mg) as a brown oil.

Example 3

Example No. 3 is the pair of regioisomers, 3-(6-methoxy-3-pyridinyl)-6-azabicyclo[3.2.1]oct-2-ene dihydrochloride and 3-(6-methoxy-3-pyridinyl)-6-azabicyclo[3.2.1]oct-3-ene dihydrochloride, which were prepared in accordance with the following techniques:

3-(6-Methoxy-3-pyridinyl)-6-azabicyclo[3.2.1]oct-2-ene dihydrochloride and 3-(6-methoxy-3-pyridinyl)-6-azabicyclo[3.2.1]oct-3-ene dihydrochloride To a solution of a mixture of t-butyl 3-trifluoromethanesulfonyloxy-6-azabicyclo[3.2.1]oct-2-ene-6-carboxylate and t-butyl 3-trifluoromethanesulfonyloxy-6-azabicyclo [3.2.1]oct-3-ene-6-carboxylate (120 mg, 0.336 mmol) in dimethoxyethane (2 ml) was added a saturated solution of sodium carbonate (0.5 ml), lithium chloride (42 mg, 1 mmol) and 2-methoxy-5-pyridinylboronic acid 1,3-propanediol cyclic ester (96 mg, 0.5 mmol). The reaction flask was evacuated under high vacuum and filled with nitrogen three times, then palladium tetrakis(triphenylphosphine) catalyst was added (20 mg). The reaction mixture was stirred vigorously and heated under reflux for 2.5 h. The dark mixture was diluted with ethyl acetate (20 ml) and filtered through a Celite pad into 50% aq. ammonium hydroxide solution (20 ml). The mixture was extracted with ethyl acetate (2×15 ml) and then the combined organics were washed with brine (2×15 ml) and dried over magnesium sulfate. Concentration by rotary evaporation gave a dark oil, which was purified by column chromatography, using a hexane/ethyl acetate gradient (0-30% ethyl acetate) as eluent, to afford the product as a brown oil (65 mg, 63%). A solution of the resulting mixture of regioisomers in dioxane (1 ml) was treated with 4N HCl in dioxane (0.5 ml) at room temperature for 20 min. Removal of solvent by rotary evaporation left a residue, which was recrystallized from isopropanol-ether to give the product as a pale yellow foam (GC: 86% purity, 2 isomers 61% and 25% respectively).

Example 4

Example 4 Example No. 4 is the pair of regioisomers, 3-(5-phenoxy-3-pyridinyl)-6-azabicyclo[3.2.1]oct-2-ene dihydrochloride and 3-(5-phenoxy-3-pyridinyl)-6-azabicyclo[3.2.1]oct-3-ene dihydrochloride, which were prepared in accordance with the following techniques:

3-(5-Phenoxy-3-pyridinyl)-6-azabicyclo[3.2.1]oct-2-ene dihydrochloride and 3-(5-phenoxy-3-pyridinyl)-6-azabicyclo[3.2.1]oct-3-ene dihydrochloride To a solution of a mixture of t-butyl 3-trifluoromethanesulfonyloxy-6-azabicyco[3.2.1]oct-2-ene-6-carboxylate and t-butyl 3-trifluoromethanesulfonyloxy-6-azabicyco[3.2.1] oct-3-ene-6-carboxylate (144 mg, 0.40 mmol) in of dimethoxyethane (2 ml) was added a saturated solution of sodium carbonate (0.5 ml), lithium chloride (50 mg, 1.2 mmol) and 5-phenoxy-3-pyridinylboronic acid (128 mg, 0.60 mmol). The reaction flask was evacuated under high vacuum and filled with nitrogen three times, then palladium tetrakis (triphenylphosphine) catalyst was added (50 mg). The reaction mixture was stirred vigorously and heated under reflux for 2.5 h. The dark mixture was diluted with ethyl acetate (20 ml) and filtered through a Celite pad into 50% aq. ammonium hydroxide solution (20 ml). The mixture was extracted with ethyl acetate (2×15 ml) and then the combined organics were washed with brine (2×15 ml) and dried over magnesium sulfate. Concentration by rotary evaporation gave a dark oil, which was purified by column chromatography, using a hexane/ethyl acetate gradient (0-30% ethyl acetate) as eluent, to afford the product as a brown oil. A solution of the resulting pair of regioisomers in dioxane (1 ml) was treated with 4 N HCl in dioxane (0.5 ml) at room temperature for 20 min. Removal of solvent by rotary evaporation left a residue, which was recrystallized from isopropanol/ether to give a mixture of the desired pair of regioisomers (32 mg) as a pale yellow foam.

Example 5

Example No. 5 is the pair of isomers 6-methyl-3-(3-pyridinyl)-6-azabicyclo[3.2.1]oct-2-ene and 6-methyl-3-(3-pyridinyl)-6-azabicyclo [3.2.1]oct-3-ene, which were prepared in accordance with the following techniques:

6-Methyl-3-(3-pyridinyl)-6-azabicyclo[3.2.1]oct-2-ene and 6-methyl-3-(3-pyridinyl)-6-azabicyclo[3.2.1]oct-3-ene To a suspension of a mixture of 3-(3-pyridinyl)-6-azabicyclo[3.2.1]oct-2-ene dihydrochloride and 3-(3-pyridinyl)-6-azabicyclo[3.2.1]oct-3-ene dihydrochloride (50 mg, 0.18 mmol) in dichloroethane (3 ml) was added aqueous 40% formaldehyde (75 mg, 1 mmol), followed by sodium triacetoxyborohydride (215 mg, 1 mmol). The mixture was stirred overnight at room temperature and then concentrated by rotary evaporation. The residue was dissolved in methylene chloride and saturated sodium bicarbonate was added. The phases were separated and the organics was washed with brine, dried over magnesium sulfate, and concentrated by rotary evaporation. The residue was filtered through a plug of silica, eluting with methanol/dichloromethane (10% methanol with 1% ammonium hydroxide), to give a mixture of the desired pair of regioisomers (15 mg) as a pale yellow oil.

Example 6

Example No. 6 is the pair of isomers 3-(5-phenyl-3-pyridinyl)-6-azabicyclo[3.2.1]oct-2-ene dihydrochloride and 3-(5-phenyl-3-pyridinyl)-6-azabicyclo[3.2.1]oct-3-ene dihydrochloride, which were prepared in accordance with the following techniques:

3-(5-Phenyl-3-pyridinyl)-6-azabicyclo[3.2.1]oct-2-ene dihydrochloride and 3-(5-phenyl-3-pyridinyl)-6-azabicyclo[3.2.1]oct-3-ene dihydrochloride To a solution of a mixture of t-butyl 3-trifluoromethanesulfonyloxy-6-azabicyco[3.2.1]oct-2-ene-6-carboxylate and t-butyl 3-trifluoromethanesulfonyloxy-6-azabicyco[3.2.1]oct-3-ene-6-carboxylate (72 mg, 0.2 mmol) in dimethoxyethane (1 ml) was added a saturated solution of sodium carbonate (0.3 ml), lithium chloride (25 mg, 0.6 mmol) and 5-phenyl-3-pyridinylboronic acid (60 mg, 0.3 mmol). The reaction flask was evacuated under high vacuum and filled with nitrogen three times, then palladium tetrakis (triphenylphosphine) catalyst was added (23 mg). The reaction mixture was stirred vigorously and heated under reflux for 2.5 h. The dark mixture was diluted with ethyl acetate (20 ml) and filtered through a Celite pad into 50% aq. ammonium hydroxide solution (20 ml). The mixture was extracted with ethyl acetate (2×15 ml) and then the combined organics were washed with brine (2×15 ml) and dried over magnesium sulfate. Concentration by rotary evaporation gave a dark oil, which was purified by column chromatography, using a hexane/ethyl acetate gradient (0-30% ethyl acetate) as eluent, to afford the product as a brown oil. A solution of the resulting pair of regioisomers in dioxane (1 ml) was treated with 4 N HCl in dioxane (0.5 ml) at room temperature for 20 min. Removal of solvent by rotary evaporation left a residue, which was recrystallized from isopropanol/ether to give a mixture of the desired pair of regioisomers (11 mg) as a pale yellow foam.

Example 7

Example No. 7 is the pair of isomers 3-(5-isopropoxy-3-pyridinyl)-6-azabicyclo[3.2.1]oct-2-ene dihydrochloride and 3-(5-isopropoxy-3-pyridinyl)-6-azabicyclo[3.2.1]oct-3-ene dihydrochloride, which were prepared in accordance with the following techniques:

3-(5-Isopropoxy-3-pyridinyl)-6-azabicyclo[3.2.1]oct-2-ene dihydrochloride and 3-(5-isopropoxy-3-pyridinyl)-6-azabicyclo[3.2.1]oct-3-ene dihydrochloride To a solution of a mixture of t-butyl 3-trifluoromethanesulfonyloxy-6-azabicyco[3.2.1]oct-2-ene-6-carboxylate and t-butyl 3-trifluoromethanesulfonyloxy-6-azabicyco[3.2.1]oct-3-ene-6-carboxylate (120 mg, 0.336 mmol) in dimethoxyethane (2 ml) was added a saturated solution of sodium carbonate (0.5 ml), lithium chloride (42 mg, 1 mmol) and 5-isopropoxy-3-pyridinylboronic acid (130 mg, 0.5 mmol). The reaction flask was evacuated under high vacuum and filled with nitrogen three times, then palladium tetrakis (triphenylphosphine) catalyst was added (20 mg). The reaction mixture was stirred vigorously and heated under reflux for 2.5 h. The dark mixture was diluted with ethyl acetate (20 ml) and filtered through a Celite pad into 50% aq. ammonium hydroxide solution (20 ml). The mixture was extracted with ethyl acetate (2×15 ml) and then the combined organics were washed with brine (2×15 ml) and dried over magnesium sulfate. Concentration by rotary evaporation gave a dark oil, which was purified by column chromatography, using a hexane/ethyl acetate gradient (0-30% ethyl acetate) as eluent, to afford the product as a brown oil. A solution of the resulting regioisomers in dioxane (1 ml) was treated with 4 N HCl in dioxane (0.5 ml) at room temperature for 20 min. Removal of solvent by rotary evaporation left a residue, which was recrystallized from isopropanol/ether to give a mixture of the desired pair of regioisomers (35 mg) as a yellow foam.

Example 8

Example No. 8 is 4-(3-pyridinyl)-6-azabicyclo[3.2.1]oct-3-ene dihydrochloride, which was prepared in accordance with the following techniques:

6-Benzyl-6-azabicyclo[3.2.1]oct-3-en-7-one

To a solution of N-benzyl-5-hydroxycyclohex-3-enecarboxamide (3.0 g, 13 mmol) in chloroform (10 ml) was added drop-wise thionyl chloride (5.0 ml, 68 mmol). The mixture turned orange and foamed vigorously, then faded gradually to a nearly colorless solution over a 30 min period. The mixture was cautiously treated with water, and when foaming stopped, transferred to a separatory funnel. The chloroform layer washed with water, brine, dried over magnesium sulfate and concentrated to a pale yellow solid. The crude product was dissolved in THF (20 ml) and added to a solution of potassium t-butoxide (1.8 g, 15 mmol) in THF (30 ml). The mixture was stirred at room temperature overnight. The reaction mixture was diluted with ethyl acetate, washed with water and brine, dried over sodium sulfate and concentrated by rotary evaporation to an acrid-smelling yellow oil (200 mg). Purification by column chromatography, using a gradient of hexane/ethyl acetate (20-50% ethyl acetate) as eluent, gave the clean lactam as a pale yellow oil (1.4 g, 51%).

8-Benzyl-3-oxa-8-azatricyclo[4.2.1.0$^{2,4}$]nonan-7-one

To a solution of 6-benzyl-6-azabicyclo[3.2.1]oct-3-en-7-one (1.0 g, 4.7 mmol) in chloroform (50 ml) cooled in an ice bath was added mete chloroperbenzoic acid (1.22 g, 7.0 mmol) in 3 portions over 5 min. The reaction mixture was allowed to warm to room temperature and stirred overnight. The resulting clear solution was treated cautiously with dilute aqueous sodium thiosulfate solution to reduce any excess meta-chloroperbenzoic acid, and the layers separated. The organic layer was washed with saturated sodium bicarbonate, water and brine, and dried over sodium sulfate. The solvent was removed by rotary evaporation to give the epoxide as a viscous oil, which solidified on brief standing. It was used without further purification the next step.

6-Benzyl-6-azabicyclo[3.2.1]octan-4-ol

To a suspension of lithium aluminum hydride (185 mg, 4.87 mmol) in THF (50 ml) cooled to 0(C was added drop-wise a solution of 8-benzyl-3-oxa-8-azatricyclo[4.2.1.0$^{2,4}$]nonan-7-one (1.15 g, 5.02 mmol) in THF (5 ml). The reaction was allowed to stir overnight at room temperature, then cooled in an ice bath and diluted with ether (50 ml). The reaction was quenched cautiously with water (0.2 ml), 1 M sodium hydroxide (0.3 ml) and water (0.2 ml), successively. After stirring for 1 h, the suspension was filtered, and the filtrate was concentrated by rotary evaporation to give the amino alcohol as a viscous yellow oil (0.90 g, 83%).

t-Butyl 4-hydroxy-6-azabicyclo[3.2.1]octane-6-carboxylate

To a solution of 6-benzyl-6-azabicyclo[3.2.1]octan-4-ol (0.90 g, 4.2 mmol) in methanol (50 ml) was added 10% Pd/C (200 mg) and a few drops of 12 N HCl. The mixture was subjected to hydrogenolysis for 48 h (45 psi of hydrogen) on a Parr apparatus. The mixture was filtered through Celite and the filtrate was concentrated by rotary evaporation to yield a sticky yellow oil, which was then suspended in dichloromethane (25 ml) and cooled in an ice bath. Triethylamine (1.4 ml, 10 mmol) was added, followed by di-t-butyl dicarbonate (1.09 g, 5.00 mmol), and the mixture was stirred overnight. The reaction mixture was washed with water, 1 N HCl and brine (2×15 ml each), dried over magnesium sulfate and concentrated by rotary evaporation to a sticky solid. The residue was purified by column chromatography, using a hexane/ethyl acetate gradient (0-50% ethyl acetate) as eluent, to give the alcohol as a white solid (400 mg, 43%).

t-Butyl 4-oxo-6-azabicyclo[3.2.1]octane-6-carboxylate

To a solution of t-butyl 4-hydroxy-6-azabicyclo[3.2.1]octane-6-carboxylate (800 mg, 3.52 mmol) in dry dichloromethane (75 ml) was added Celite (2 g), sodium acetate (0.82 g, 10 mmol) and pyridinium chlorochromate (1.1 g, 5.1 mmol). The mixture was stirred under nitrogen for 66 h. The dark suspension was diluted with ether (50 ml) and filtered through a plug of silica gel to give a light brown solution. Removal of solvent by rotary evaporation and purification by column chromatography of the residue, using a methanol/dichloromethane gradient (0-10% methanol) as eluent, gave the ketone as a pale yellow oil (770 mg, 96%).

t-Butyl 4-trifluoromethanesulfonyloxy-6-azabicyclo [3.2.1]oct-3-ene-6-carboxylate To a solution of diisopropylamine (0.42 ml, 3.0 mmol) in dry THF (20 ml) was added 2.5 M n-butyllithium (1.2 ml, 3.0 mmol) drop-wise at −78(C. After 15 min, t-butyl 4-oxo-6-azabicyclo[3.2.1]octane-6-carboxylate in THF (5 ml) was added drop-wise. The pale orange reaction mixture was stirred at −78(C for 45 min, then treated with 2-(N,N-bis(trifluoromethylsulfonyl)amino-5-chloropyridine (0.82 g, 2.1 mmol) in one portion. The reaction was allowed to warm slowly to −10(C over 1.5 h. The reaction was quenched by the addition of saturated ammonium chloride solution (10 ml). The mixture was extracted with ethyl acetate (3×15 ml) and the combined extracts were washed with 1 N HCl, 10% potassium hydroxide solution, and brine (2×10 ml each) in succession. The dried extracts were filtered and concentrated by rotary evaporation, and the residue was purified by column chromatography, using a hexane/ethyl acetate gradient (0-50% ethyl acetate) as eluent, to give the triflate as a yellow oil (400 mg, 56%).

4-(3-pyridinyl)-6-azabicyclo[3.2.1]oct-3-ene dihydrochloride

To a solution of t-butyl 4-trifluoromethanesulfonyloxy-6-azabicyclo [3.2.1]oct-3-ene-6-carboxylate (100 mg, 0.28 mmol) in dimethoxyethane (2 ml) was added a saturated solution of sodium carbonate (0.5 ml), lithium chloride (36 mg, 0.84 mmol) and 3-pyridinylboronic acid 1,3-propanediol cyclic ester (68 mg, 0.42 mmol). The reaction mixture was evacuated under high vacuum and filled with nitrogen three times, then palladium tetrakis(triphenylphosphine) catalyst (20 mg) was added. The reaction mixture was stirred vigorously and heated under reflux for 0.5 h. The dark mixture was diluted with ethyl acetate (20 ml) and filtered through a Celite pad into 50% aqueous ammonium hydroxide solution (10 ml). The mixture was extracted with ethyl acetate (2×15 ml), the combined organics washed with brine (2×15 ml), and dried over magnesium sulfate. Concentration by rotary evaporation gave a dark oil, which was purified by column chromatography, using a hexane/ethyl acetate gradient as eluent (0-30% ethyl acetate), to afford the product as a colorless oil (60 mg, 75%). A solution of the oil in dioxane (1 ml) was treated with 4N HCl in dioxane (0.5 ml) at room temperature for 20 min. Removal of solvent by rotary evaporation left a residue, which was recrystallized from isopropanol/ether to give the dihydrochloride salt as a pale yellow powder (34 mg, 63%).

Example 9

Example No. 9 is 6-(3-pyridinyl)-3-azabicyclo[3.2.1]oct-6-ene dihydrochloride, which was prepared in accordance with the following techniques:

2-Chlorobicyclo[2.2.1]hept-5-ene-2-carbonitrile

To a solution of 2-chloroacrylonitrile (50.0 g, 571 mmol) in toluene (150 ml) was slowly added cyclopentadiene (37.7 g, 571 mmol). The reaction was stirred for 60 h at ambient temperature under a nitrogen atmosphere. The reaction was then concentrated by rotary evaporation to remove the majority of the toluene. The compound was purified by vacuum distillation (100-150° C., 15 mm Hg) to afford the nitrile as a white solid (49.7 g, 56.5%).

Bicyclo[2.2.1]hept-5-en-2-one

To a stirring solution of potassium hydroxide (85 g) in water (30 ml) was added drop-wise a solution of 2-chlorobicyclo[2.2.1]hept-5-ene-2-carbonitrile in DMSO (450 ml). The reaction turned red as the nitrile was added. The mixture was stirred for 48 h. Water (500 ml) was added, then distilled off (70-100° C., 15 mm Hg) which brought the ketone with it. This steam distillation was performed a second time (another 500 ml of water). The distilled fractions were combined, extracted with diethyl ether (3×200 ml), dried over sodium sulfate, filtered and concentrated. This compound was distilled once more (90° C., 15 mm Hg) to yield the ketone as a clear, colorless oil (26.6 g, 76%).

Bicyclo[2.2.1]hept-5-en-2-one ethylene ketal

To a stirring solution of bicyclo[2.2.1]hept-5-en-2-one (14.6 g, 135 mmol) in benzene (250 ml) was added p-toluenesulfonic acid (2.59 g, 13.6 mmol) and ethylene glycol (15.1 g, 271 mmol). The mixture was then refluxed for 60 h under nitrogen using a Dean Stark trap. After the reaction was cooled to ambient temperature, it was stirred with saturated sodium bicarbonate (100 ml) for 30 min. The layers were separated and the aqueous phase extracted with ethyl acetate (1×100 ml). The organic extractions were then combined, dried over sodium sulfate, filtered and concentrated to yield the ketal as a clear, colorless oil (18.1 g, 88.1%).

6,8-Bis(hydroxymethyl)-1,4-dioxaspiro[4.4]nonane

A solution of bicyclo[2.2.1]hept-5-en-2-one ethylene ketal (7.04 g, 46.3 mmol) in 30% methanol/dichloromethane (200 ml) was subjected to ozonolysis for 45 min (10 min past the point at which the reaction turned blue) at −78° C. Nitrogen gas was then passed through the solution until it again turned clear. At this point, sodium borohydride (5.25 g, 139 mmol) was added in one portion. The reaction was then slowly allowed to come to room temperature while stirring under nitrogen. After 18 h the reaction was concentrated by rotary evaporation. Then saturated ammonium chloride (25 ml) was added, and the solution extracted with chloroform (5×75 ml). The organic extracts were combined, dried over sodium sulfate, filtered and concentrated to yield the diol as a clear, colorless oil (5.66 g, 65.1%).

6,8-Bis(methylsulfonyloxymethyl)-1,4-dioxaspiro[4.4]nonane 6,8-Bis(hydroxymethyl)-1,4-dioxaspiro[4.4]nonane (8.18 g, 43.5 mmol) was dissolved in dichloromethane (200 ml) and chilled to 0° C. To the chilled solution was added 4-dimethylaminopyridine (0.53 g, 4.4 mmol) and distilled triethylamine (18.2 ml, 131 mmol). Then methanesulfonyl chloride (7.41 ml, 11.0 g, 95.7 mmol) was added drop-wise via syringe over 10 min and the reaction was allowed to come to ambient temperature and stir for 18 h under nitrogen. The reaction was quenched with saturated sodium bicarbonate (25 ml) and stirred for 30 min. After stirring, the layers were separated and the aqueous phase extracted with dichloromethane (2×50 ml). The organics were combined, dried over sodium sulfate, filtered and concentrated to yield a reddish brown oil (14.9, 99.4%).

3-Azabicyclo[3.2.1]octan-6-one ethylene ketal 6,8-Bis(methanesulfonyloxymethyl)-1,4-dioxaspiro[4.4]nonane (14.90 g, 43.3 mmol) was suspended in aqueous ammonia (35%, 150 ml) and heated for 18 h at 60° C. The reaction was cooled to ambient temperature and concentrated by rotary evaporation. The residue was treated with saturated sodium chloride solution (50 ml) and extracted with chloroform (3×50 ml). The organic extracts were combined, dried over sodium sulfate, filtered and concentrated to yield a brown oil (7.69 g, 100%).

Ethyl 6-oxo-3-azabicyclo[3.2.1]octane-3-carboxylate ethylene ketal

3-Azabicyclo[3.2.1]octan-6-one ethylene ketal (7.69 g, 45.5 mmol) was dissolved in methylene chloride (200 ml) and chilled to 0° C. To this solution was added triethylamine (6.34 ml, 91.0 mmol), then ethyl chloroformate (4.02 ml, 50.1 mmol) drop-wise. The reaction was warmed to ambient temperature and stirred for 18 h. Saturated sodium bicarbonate solution (100 ml) was added, and the organic layer was separated. The aqueous layer was saturated with sodium chloride and extracted with methylene chloride (1×100 ml). The organics were then combined, dried over sodium sulfate, filtered and concentrated. The crude brown residue was then distilled on a Kugelrohr apparatus (0.2 mm Hg, unknown temperature) to yield a clear, dark brown oil (6.72 g, 61.3%).

Ethyl 6-oxo-3-azabicyclo[3.2.1]octane-3-carboxylate

A 2% solution of aqueous sulfuric acid (100 ml) was added to ethyl 6-oxo-3-azabicyclo[3.2.1]octane-3-carboxylate ethylene ketal (6.72 g, 27.9 mmol) and the mixture was allowed to stir for 1 h. The mixture was then extracted with ethyl acetate (2×100 ml). The combined organic layers were dried over potassium carbonate, filtered, concentrated by rotary evaporation, and then distilled on a Kugelrohr apparatus (0.2 mm Hg, 132-162° C.) to yield a clear colorless oil (3.49 g, 64%).

Ethyl 6-hydroxy-6-(3-pyridinyl)-3-azabicyclo[3.2.1]octane-3-carboxylate

To a solution of 3-bromopyridine (1.04 g, 6.58 mmol) in dry diethyl ether (20 ml) at −78° C. was added 2.5 M n-butyllithium (2.63 ml, 6.6 mmol). The reaction was stirred for 30 min under nitrogen. The pyridinyllithium solution was then slowly transferred by cannula into a solution of ethyl 6-oxo-3-azabicyclo[3.2.1]octane-3-carboxylate (1.00 g, 5.07 mmol) in THF (10 ml) at −78° C. The reaction was stirred 4 h at −78° C. and then quenched with saturated aqueous ammonium chloride (10 ml). The reaction was then extracted with chloroform (3×25 ml), the combined extracts dried over sodium sulfate, filtered, and concentrated by rotary evaporation. Excess pyridine was removed by repeated azeotropic rotary evaporation with toluene to yield the desired product (1.20 g, 86%).

6-(3-pyridinyl)-3-azabicyclo[3.2.1]oct-6-ene

To ethyl 6-hydroxy-6-(3-pyridinyl)-3-azabicyclo[3.2.1] octane-3-carboxylate (1.10 g, 4.0 mmol) was added thionyl chloride (5 ml) and the mixture was heated to reflux for 1 h under nitrogen. Thionyl chloride was removed by azeotropic rotary evaporation with toluene to give a dark brown oil, which was suspended in a 20% solution of potassium hydroxide in ethanol (10 ml) and refluxed for 18 h. The reaction mixture was cooled to room temperature and concentrated by rotary evaporation. Then saturated sodium chloride solution (10 ml) was added. The mixture was filtered. The collected solids were washed with chloroform (25 ml), and the filtrate was extracted with chloroform (3×25 ml). The combined chloroform extracts were dried over sodium sulfate, filtered, concentrated by rotary evaporation, and distilled on a Kugelrohr apparatus to yield a light brown oil (350 mg, 47%).

6-(3-pyridinyl)-3-azabicyclo[3.2.1]oct-6-ene dihydrochloride

-(3-Pyridinyl)-3-azabicyclo[3.2.1]oct-6-ene (190 mg, 1.0 mmol) was dissolved in ethanol (5 ml), and 12 N HCl (2 ml) was added. The solution was sonicated for 3 min, and then concentrated by azeotropic rotary evaporation with ethanol (3×5 ml) to yield a fluffy solid. Then the salt was dissolved in hot isopropanol (2 ml), and diethyl ether was added until a milky solution formed. Cooling in the freezer produced a light brown solid. The solid was filtered, washed with diethyl ether, and dried under high vacuum to yield 6-(3-pyridinyl)-3-azabicyclo[3.2.1] oct-6-ene dihydrochloride, (230 mg, 87%, m.p. 192-195° C.).

Example 10

Example No. 10 is 3-methyl-6-(3-pyridinyl)-3-azabicyclo [3.2.1]oct-6-ene dihydrochloride, which was prepared in accordance with the following techniques:

3-Methyl-6-(3-pyridinyl)-3-azabicyclo[3.2.1]oct-6-ene dihydrochloride

Formic acid (98%, 5 ml) and formaldehyde (37% aqueous, 1 ml) were added to 6-(3-pyridinyl)-3-azabicyclo[3.2.1]oct-6-ene (38 mg, 0.2 mmol) and the solution was refluxed for 1 h under nitrogen. The reaction was then concentrated by rotary evaporation, and the residue was converted to a freebase with saturated bicarbonate solution (10 ml) and extracted with chloroform (4×5 ml). The combined extracts were dried over sodium sulfate, filtered and concentrated by rotary evaporation. The residue was purified by Kugelrohr distillation. The hydrochloride salt was formed by addition of 12 N HCl to a solution of the compound in ethanol (10 ml), followed by azeotropic rotary evaporation with ethanol (3×5 ml) to yield a light white foam (44.4 mg, 79%).

Example 11

Example No. 11 is 7-(3-pyridinyl)-3-azabicyclo[3.3.1] non-6-ene dihydrochloride, which was prepared in accordance with the following techniques:

Dimethyl 5-oxocyclohexane-1,3-dicarboxylate

To an suspension of 5-methoxyisophthalic acid (20.00 g, 102.0 mmol) in dry methanol (75 ml) was added anhydrous ammonia (750 ml) (the ammonia gas was liquefied at −78° C. directly into the flask). Sodium metal (6.8 g, 0.30 mol) was cut into small pieces and carefully added to the flask over one hour. The solution changed from a pink to a yellow brown color over the course of the sodium addition. After stirring for 1 h at −78° C., solid ammonium chloride (50 g) was added. The mixture was then warmed to ambient temperature over a period of 1 h. The pH of the reaction was then lowered to 2 with concentrated HCl. Saturated aqueous ammonium chloride (100 ml) was added and the reaction mixture was extracted with diethyl ether (6×50 ml). The combined ether extracts were dried over anhydrous sodium sulfate, filtered and concentrated by rotary evaporation. The residue was dissolved in DMF (30 ml), treated with $K_2CO_3$ (24.0 g, 174 mmol) and stirred for 1 h. Methyl iodide (26.69 g, 173.9 mmol) was added in one portion and the reaction was stirred overnight at ambient temperature. Brine (30 ml) was then added, and the reaction was extracted with ethyl acetate (4×50 ml). The combined organic extracts were dried over sodium sulfate, filtered, and concentrated by rotary evaporation. The viscous liquid residue was dissolved in hexanes, from which the ketodiester separated as clear colorless crystals (6.5 g, 32% yield).

Dimethyl 1,4-dioxaspiro[4.5]decane-7,9-dicarboxylate

To a solution of dimethyl 5-oxocyclohexane-1,3-dicarboxylate (6.0 g, 28 mmol) in toluene (50 ml) was added ethylene glycol (3.73 g, 56.6 mmol) and p-toluenesulfonic acid (65 mg). The reaction was refluxed overnight, using a Dean-Stark trap to remove the excess water. The reaction was worked up by removing the toluene by rotary evaporation, adding brine (10 ml) and extracting with ethyl acetate (3×40 ml). The combined extracts were dried over sodium sulfate, filtered and concentrated by rotary evaporation to give the desired product as a thick colorless liquid (6.0 g, 82%).

7,9-Bis(hydroxymethyl)-1,4-dioxaspiro[4.5]decane o a solution of dimethyl 1,4-dioxaspiro[4.5]decane-7,9-dicarboxylate (6.0 g, 23 mmol) in dry THF at 0° C. was added lithium aluminum hydride (4.67 g, 68.7 mmol) under argon. The reaction was then refluxed overnight. The reaction was cooled to 0° C., and diethyl ether (100 ml) was added followed by drop-wise addition of 5 N NaOH until the gray lithium aluminum hydride was converted to a white solid. The reaction mixture was then filtered through a Celite pad, which was then washed with diethyl ether (100 ml). The combined filtrates were dried over sodium sulfate, filtered and concentrated by rotary evaporation to give the alcohol as a viscous colorless liquid (6.3 g, 93%).

7,9-Bis(methylsulfonyloxymethyl)-1,4-dioxaspiro [4.5]decane

To a solution of 7,9-bis(hydroxymethyl)-1,4-dioxaspiro [4.5]decane (6.3 g, 21 mmol) in dry dichloromethane (100 ml) with triethylamine (8.90 ml, 63.8 mmol) was added methanesulfonyl chloride (4.11 ml, 53.2 mmol) drop-wise at 0° C. The reaction was allowed to come to ambient temperature and stir overnight. The reaction was quenched with saturated sodium bicarbonate (50 ml) and allowed to stir for 15 min. After separation, the aqueous layer was extracted with dichloromethane (1×50 ml). The combined extracts were dried over potassium carbonate, filtered and concentrated to give a dark brown liquid (7.3 g, 97%).

Ethyl 3-aza-7-oxobicyclo[3.3.1]nonane-3-carboxylate ethylene ketal

To a suspension of 7,9-bis(methylsulfonyloxymethyl)-1,4-dioxaspiro [4.5]decane (7.3 g, 20 mmol) in 30% $NH_4OH$ (50 ml) was added copper(I) iodide (20 mg). The reaction was then heated at reflux for 18 h. After the reaction mixture was concentrated by rotary evaporation, saturated sodium bicarbonate solution (20 ml) was added, followed by ethyl chloroformate (3.88 ml, 40.6 mmol). This mixture was then stirred overnight at ambient temperature under nitrogen. Then it was extracted with ethyl acetate (4×40 ml). These extracts were combined, dried over potassium carbonate, filtered and concentrated by rotary evaporation to give the a light brown liquid (4.5 g, 90%).

Ethyl 7-oxo-3-azabicyclo[3.3.1]nonane-3-carboxylate

Ethyl 7-oxo-3-azabicyclo[3.3.1]nonane-3-carboxylate ethylene ketal (4.40 g, 17.2 mmol) was combined with 2% aqueous $H_2SO_4$ (50 ml) and stirred for 4 h. Then the reaction mixture was extracted with ethyl acetate (4×30 ml). The combined extracts were dried over sodium sulfate, filtered and concentrated by rotary evaporation to yield a light yellow oil (3.20 g, 88.1%).

Ethyl 7-(trifluoromethylsulfonyloxy)-3-azabicyclo [3.3.1]non-6-ene-3-carboxylate Lithium diisopropylamide (LDA) was formed at −78° C. by adding 2.5 M n-butyllithium (3.3 ml, 8.2 mmol) to diisopropylamine (1.16 ml, 8.28 mmol) in THF (100 ml), followed by stirring for 30 min under nitrogen. The LDA was then transferred by cannula into a stirring solution of ethyl 7-oxo-3-azabicyclo[3.3.1]nonane-3-carboxylate (1.16 g, 5.49 mmol) in THF (50 ml) at −78° C. The solution was allowed to warm to −40° C. over 45 min, at which point 2-[N,N-bis (trifluoromethylsulfonyl) amino]-5-chloropyridine (4.32 g, 11.0 mmol) was added in one portion. The reaction was allowed to stir and warm to 0° C. over 2 h, at which point it was quenched with saturated sodium bicarbonate solution (100 ml). The layers were separated and the aqueous layer was extracted with ether (2×25 ml). The combined organics were then washed with 1 N HCl (100 ml), saturated solutions of sodium bicarbonate and brine (1×50 ml each), dried over sodium sulfate, filtered and concentrated by rotary evaporation. The residue was then purified by column chromatography, using a hexane/ethyl acetate gradient (20-40% ethyl acetate) as eluent, to obtain a light yellow oil (1.31 g, 69.7%).

Ethyl 7-(3-pyridinyl)-3-azabicyclo[3.3.1]non-6-ene-3-carboxylate

To a solution of ethyl 7-(trifluoromethylsulfonyloxy)-3-azabicyclo[3.3.1] non-6-ene-3-carboxylate (0.34 g, 1.0 mmol) in dimethoxyethane (8 ml) was added saturated sodium carbonate solution (2.5 ml), lithium chloride (127 mg, 3.0 mmol) and pyridinylboronic acid (123 mg, 1.00 mmol). The flask was alternately evacuated and filled with argon three times. Then palladium tetrakistriphenylphosphine (23 mg, 0.02 mmol) was added and the evacuate/fill procedure performed once again. The flask was then sealed under argon and the stirred reaction mixture was heated at 95° C. for 2 h. The mixture was cooled to room temperature and then diluted with ether (10 ml) and filtered through a Celite pad. The Celite was washed with 30% ammonium hydroxide (25 ml) and ether (50 ml). The combined filtrates were separated into organic and aqueous phases, and the aqueous layer was extracted with ether (1×25 ml). Chloroform (20 ml) was added to the combined organic layers, and the mixture was dried over sodium sulfate and filtered. Concentrated of the filtrate by rotary evaporation, followed by purification of the residue (207 mg) by column chromatography, using a gradient of chloroform/methanol (0 to 2% methanol) as eluent, gave a light yellow oil (90 mg, 33%).

7-(3-Pyridinyl)-3-azabicyclo[3.3.1]non-6-ene dihydrochloride 7-(3-pyridinyl)-3-azabicyclo[3.3.1]non-6-ene-3-carboxylic acid ethyl ester (90 mg, 0.03 mmol) was dissolved in concentrated 12 N HCl (10 ml) and refluxed overnight. The reaction was then concentrated by rotary evaporation, and the residue was converted to a free base with saturated sodium bicarbonate (~20 ml). The mixture was treated with saturated with sodium chloride (~3 g) and extracted with chloroform (3×10 ml). The combined organic extracts were dried over sodium sulfate, filtered and concentrated by rotary evaporation. The residue was purified by column chromatography, using methanol/chloroform (10% methanol with 1% ammonium hydroxide) as eluent, to yield 26.2 mg of the free base. Concentrated HCl (5 drops) was added to a solution of the free base in ethanol (10 ml). The excess HCl and residual water were removed by repeated azeotropic rotary evaporation with ethanol. The crude salt was dissolved in hot isopropanol (5 ml) and diluted with diethyl ether (1 ml). The solution turned cloudy and was allowed to slowly cool for 1 h. White crystals formed on the sides. The supernatant was decanted, and the solid was washed with a 20% ether/isopropanol solution and dried on a hi-vacuum pump. This gave 7-(3-pyridinyl)-3-azabicyclo[3.3.1]non-6-ene dihydrochloride as a white powder (14 mg, 16%, m.p. 219-221° C.).

Example 12

Example No. 12 is 7-(3-pyridinyl)-3-azabicyclo[3.3.1] nonane dihydrochloride, which was prepared in accordance with the following techniques:

7-(3-pyridinyl)-3-azabicyclo[3.3.1]nonane dihydrochloride 7-(3-pyridinyl)-3-azabicyclo[3.3.1]non-6-ene dihydrochloride (17.2 mg, 0.0629 mmol) was dissolved in methanol (10 ml), and 10% Pd/C (5 mg) was added. The mixture was hydrogenated for 3 h using a hydrogen-filled balloon. When the reaction was complete, the reaction was filtered through Celite, washed with methanol and concentrated by rotary evaporation to a light brown solid. This was dissolved in ethanol (10 ml) and treated with concentrated HCl (5 drops). The excess HCl and residual water were removed by repeated azeotropic rotary evaporation with ethanol. 7-(3-Pyridinyl)-3-azabicyclo[3.3.1] nonane dihydrochloride was isolated as a white solid (18.2 mg, 100%). GC-MS shows a 85:15 ratio of diastereomers.

Example 13

Example No. 13 is 3-methyl-7-(3-pyridinyl)-3-azabicyclo [3.3.1]non-6-ene, which was prepared in accordance with the following techniques:

3-Methyl-7-(3-pyridinyl)-3-azabicyclo[3.3.1]non-6-ene dihydrochloride 7-(3-pyridinyl)-3-azabicyclo[3.3.1]non-6-ene dihydrochloride (90 mg, 0.33 mmol) was dissolved in 37% aqueous formaldehyde (3 ml), and 98% formic acid (10 ml) was added. This mixture was refluxed for 1 h. The reaction was then cooled, concentrated by rotary evaporation, and treated with saturated sodium bicarbonate solution (15 ml). It was then extracted with chloroform (3×15 ml), and the extracts were dried over sodium sulfate, filtered and concentrated by rotary evaporation. Concentrated HCl (5 drops) was added to a solution of the free base in ethanol (10 ml). The excess HCl and residual water were removed by repeated azeotropic rotary evaporation with ethanol. 3-Methyl-7-(3-pyridinyl)-3-azabicyclo[3.3.1]non-6-ene dihydrochloride was isolated as a white, hygroscopic solid (116 mg, >100% due to moisture content).

Example 14

Example No. 14 is 6-methyl-4-(3-pyridinyl)-6-azabicyclo [3.2.1]oct-3-ene dihydrochloride, which was prepared in accordance with the following techniques:

6-Methyl-4-(3-pyridinyl)-6-azabicyclo[3.2.1]oct-3-ene dihydrochloride

To a suspension of 4-(3-pyridinyl)-6-azabicyclo[3.2.1]oct-3-ene dihydrochloride (90 mg, 0.35 mmol) in 15 mL of dichloromethane was added a solution of formaldehyde (37% aqueous, 0.15 mL, ~1.8 mmol). With vigorous stirring, solid sodium triacetoxyborohydride (300 mg, 1.4 mmol) was added in two portions. The reaction was allowed to stir overnight at ambient temperature. The reaction mixture was quenched by the addition of a sodium hydroxide solution (10% aqueous, approximately 1 mL), and the whole extracted with dichloromethane (2×10 mL). The organic extracts were washed successively with water and brine (10 mL each), and dried over sodium sulfate. Filtration and removal of solvent in vacuo gave a residue, which was dissolved in a small volume of methanol and treated with approximately 1 mL of 4M HCl in dioxane. The resulting solution was concentrated in vacua, and the residue taken up in a minimum amount of warm isopropanol. After cooling briefly, ether was added to the point of cloudiness, and the solution cooled slowly to ambient temperature. A sticky solid precipitate formed which resisted crystallization. Solvents were removed in vacuo, leaving the product as a hygroscopic, gummy mass (30 mg, 32%).

Example 15

Example No. 15 is 4-(5-methoxy-3-pyridinyl)-6-azabicyclo[3.2.1]oct-3-ene, which was prepared in accordance with the following techniques:

4-(5-Methoxy-3-pyridinyl)-6-azabicyclo[3.2.1]oct-3-ene

To a solution of t-butyl 4-trifluoromethanesulfonyloxy-6-azabicyclo [3.2.1]oct-3-ene-6-carboxylate (200 mg, 0.560 mmol) in dimethoxyethane (4 mL) was added a saturated solution of sodium carbonate (1 mL), lithium chloride (72 mg, 1.7 mmol) and 5-methoxy-3-pyridinylboronic acid (128 mg, 0.837 mmol). The reaction mixture was evacuated under high vacuum and filled with nitrogen thee times, then tetrakis (triphenylphosphine)palladium(0) catalyst (40 mg) was added. The reaction mixture was stirred vigorously and heated under reflux for 45 min. The dark mixture was diluted with ethyl acetate (20 mL) and filtered though a Celite pad into 14% aqueous ammonium hydroxide (10 mL). The mixture was extracted with ethyl acetate (2×15 mL), the combined organics washed with brine (2×15 mL), and dried over anhydrous magnesium sulfate. Concentration by rotary evaporation gave a dark oil, which was purified by column chomatography, using a hexane/ethyl acetate gradient (0-100% ethyl acetate) as eluent, to afford the product as a colorless oil (120 mg, 68%). A solution of the oil in dichloromethane (5 mL) was treated with trifluoroacetic acid (1 mL) at ambient temperature for 2 h. Removal of solvent by rotary evaporation left a residue, which was treated with a few drops of concentrated ammonium hydroxide. The water was removed by azeotropic evaporation with of ethanol (3×5 mL). The residue was taken up in dichloromethane and filtered though a cotton plug to give, after concentration, a yellow oil (30 mg, 100%).

Example 16

Example No. 16 is 6-methyl-4-(5-methoxy-3-pyridinyl)-6-azabicyclo [3.2.1]oct-3-ene, which was prepared in accordance with the following techniques:

6-Methyl-4-(5-methoxy-3-pyridinyl)-6-azabicyclo [3.2.1]oct-3-ene

A mixture of 4-(5-methoxy-3-pyridinyl)-6-azabicyclo [3.2.1]oct-3-ene (15 mg, 0.07 mmol), aqueous formaldehyde (37%, 0.25 mL) and 90% formic acid (1 mL) was heated at reflux for 1½ h. The mixture was concentrated under reduced pressure, and the remaining volatiles were removed by azeotropic evaporation with methanol (thee times). The residue was made basic with dilute aqueous sodium hydroxide and extracted into dichloromethane. The extracts were dried over anhydrous sodium sulfate, filtered and concentrated. The crude product was chromatographed on a silica gel column, eluting with 90:10:1 dichloromethane/methanol/concentrated ammonium hydroxide. Concentration of selected fractions gave the product as an oil (9.0 mg, 56%).

Example 17

Example No. 17 is 4-(3-methyl-5-isoxazolyl)-6-azabicyclo[3.2.1]oct-3-ene, which was prepared in accordance with the following techniques:

tert-Butyl 4-ethynyl-6-azabicyclo[3.2.1]oct-3-ene-6-carboxylate

To a solution of t-butyl 4-trifluoromethanesulfonyloxy-6-azabicyclo [3.2.1]oct-3-ene-6-carboxylate (1.8 g, 5.0 mmol) in 10 mL of toluene was added 20 mL of triethylamine, followed by trimethylsilylacetylene (0.49 g, 5.0 mmol). The mixture was degassed, placed under a nitrogen atmosphere, and copper iodide (50 mg) and bis (triphenylphosphine)palladium dichloride (100 mg) were added. The reaction mixture was heated under reflux for 16 h, then cooled and concentrated under reduced pressure. The residue was chromatographed on a silica gel column, using 0-50% ethyl acetate in hexane as eluent, to give tert-butyl 4-trimethylsilylethynyl-6-azabicyclo [3.2.1]oct-3-ene-6-carboxylate (900 mg, 58.9%). This was dissolved in 25 mL of methanol and treated with solid potassium carbonate (~1 g) with vigorous stirring. After 4 h, the mixture was concentrated to dryness in vacuo, and the residue was column chromatographed on silica gel, eluting with 2:1 hexane/ethyl acetate, to give a yellow oil (300 mg, 25.8% for two steps).

tert-Butyl 4-(3-methyl-5-isoxazolyl)-6-azabicyclo[3.2.1]oct-3-ene-6-carboxylate To a solution of acetaldoxime (65 mg, 1.1 mmol) in 15 mL of chloroform were added 2 drops of pyridine, followed by N-chlorosuccinimide (146 mg, 1.1 mmol). After stirring the cloudy mixture for 1 h at ambient temperature, tert-butyl 4-ethynyl-6-azabicyclo[3.2.1]oct-3-ene-6-carboxylate (233 mg, 1.00 mmol) was added in 2 mL of chloroform, followed by drop-wise addition of triethylamine (0.175 mL, 1.25 mmol). The mixture was stirred at ambient temperature for 4 h and then concentrated to dryness under reduced pressure. The residue was chromatographed on a silica gel column, with a gradient of 2:1 hexane/ethyl acetate to 2:1 ethyl acetate/hexane, to give first recovered starting material, then tert-butyl 4-(3-methyl-5-isoxazolyl)-6-azabicyclo[3.2.1]oct-3-ene-6-carboxylate (100 mg, 40%).

4-(3-Methyl-5-isoxazolyl)-6-azabicyclo[3.2.1]oct-3-ene

A solution of tert-butyl 4-(3-methyl-5-isoxazolyl)-6-azabicyclo[3.2.1] oct-3-ene-6-carboxylate (80 mg, 0.28 mmol) in 10 mL of dichloromethane was treated with trifluoroacetic acid (2 mL) with ice bath cooling. After stirring 2 h and warming to ambient temperature, the reaction mixture was concentrated to dryness under reduced pressure. The residue was made basic with 10% potassium hydroxide solution and extracted with chloroform (2×10 mL). The extracts were dried over anhydrous sodium sulfate, filtered and concentrated to give the desired product as a viscous oil (30 mg, 58%).

Example 18

Example No. 18 is 6-(3-pyridinyl)-3-azabicyclo[3.3.1]non-6-ene, which was prepared in accordance with the following techniques:

Cyclohex-3-enylmethylamine

To a stirred suspension of lithium aluminum hydride (3.70 g, 100 mmol) in 200 mL of THF, cooled in an ice bath, was added drop-wise a solution of cyclohexene-3-carbonitrile (10.7 g, 100 mmol) in 50 mL of THF. After addition was complete, the mixture was heated at reflux for 14 h. The mixture was cooled in an ice bath, diluted with 200 mL of ether, and quenched by careful sequential addition of 3.7 mL of water, 5.5 mL of 10% NaOH, and 4 mL of water. After stirring for 1 h, the mixture was filtered and concentrated to give the product amine, as a colorless liquid (10 g, 90%).

Ethyl cyclohex-3-en-1-ylmethylcarbamate

Cyclohex-3-enylmethylamine (10 g, 90 mmol) was dissolved in 200 mL of dichloromethane and cooled in an ice bath. Triethylamine (16.8 mL, 120 mmol) was added, followed by drop-wise addition of ethyl chloroformate (10.9 g, 0.100 mol). The mixture was stirred overnight at ambient temperature, then washed with water, dilute HCl, dilute aqueous sodium hydroxide, and brine (50 mL each). The organic layer was dried over anhydrous magnesium sulfate, filtered and concentrated under reduced pressure to give the crude carbamate (14 g, 85%).

Ethyl N-(hydroxymethyl)cyclohex-3-en-1-ylmethylcarbamate

A sample of ethyl cyclohex-3-en-1-ylmethylcarbamate (5.1 g, 28 mmol) in 500 mL of THF was treated with paraformaldehyde (16.7 g, 560 mmol), potassium carbonate (7.8 g, 56 mmol) and cesium carbonate (1.8 g, 5.6 mmol). The mixture was stirred vigorously and heated under reflux for 4 h. The mixture was cooled, filtered and concentrated under reduced pressure. The residue was column chromatographed on silica gel, using 3:1 hexane/ethyl acetate as eluent, to give a colorless oil (3.6 g, 61%).

Ethyl 3-azabicyclo[3.3.1]non-6-ene-3-carboxylate

To a stirred solution of ethyl N-(hydroxymethyl)cyclohex-3-en-1-ylmethylcarbamate (213 mg, 1.00 mmol) in 15 mL of dichloromethane, cooled in an ice bath, was added drop-wise boron trifluoride etherate (0.19 mL, 1.5 mmol). The initially cloudy reaction mixture slowly cleared. After it had become homogenous, it was warmed to ambient temperature and stirred for 1.5 h. The reaction was quenched by sequential addition of 5 mL of water and 5 mL of 10% KOH solution. The mixture was extracted with dichloromethane (2×20 mL), and the combined extracts were washed with brine (25 mL), dried over anhydrous sodium sulfate and concentrated under reduced pressure. The residue was column chromatographed on silica gel with 2:1 hexane/ethyl acetate to give the product as a colorless oil (145 mg, 74%).

Ethyl 6-hydroxy-3-azabicyclo[3.3.1]nonane-3-carboxylate

A solution of ethyl 3-azabicyclo[3.3.1]non-6-ene-3-carboxylate (2.50 g, 12.8 mmol) in 75 mL of THF was cooled in an ice bath and borane-THF (1M in THF, 19 mL, 19 mmol) was added drop-wise. The reaction was stirred at about 10(C for 3.5 h, then cooled in ice bath. A solution of sodium hydroxide (2.4 g, 60 mmol) in 10 mL water was added drop-wise, followed immediately by an additional 50 mL of THF and 10 mL of water. Hydrogen peroxide (30% aqueous, 8.5 g, 75 mmol) was then added, and the mixture stirred overnight at ambient temperature. The mixture was extracted with ether (2×50 mL), and the combined extracts were washed with water and brine (25 mL each). Drying over anhydrous magnesium sulfate, followed by filtration and concentration under reduced pressure, gave the product as a colorless, viscous oil (2.2 g, 80%).

Ethyl 6-oxo-3-azabicyclo[3.3.1]nonane-3-carboxylate

A solution of oxalyl chloride (1.31 mL, 15 mmol) in 50 mL of dichloromethane was cooled in a dry ice-acetone bath, and DMSO (1.4 mL, 20 mmol) was added drop-wise over 5 min. After 10 min, ethyl 6-hydroxy-3-azabicyclo[3.3.1]nonane-3-carboxylate (2.2 g, 10 mmol) in 10 mL dichloromethane was added over 5 min. The mixture was stirred for 20 min, and then triethylamine (6.3 mL, 45 mmol) was added slowly. The mixture was stirred for 1.5 h, gradually warming to −10° C. The reaction was quenched by addition of water (25 mL). The organic layer was separated, washed with brine (25 mL), dried over anhydrous sodium sulfate, filtered and concentrated under reduced pressure to give a yellow oil. This was chromatographed on a silica gel column, with 2% methanol in dichloromethane, to give the desired ketone (1.0 g, 45%). The chromatography also provided a sample of the isomeric ketone, ethyl 7-oxo-3-azabicyclo[3.3.1]nonane-3-carboxylate, and some un-reacted alcohol starting material.

Ethyl 6-trifluoromethanesulfonyloxy-3-azabicyclo [3.3.1]non-6-ene-3-carboxylate

A solution of LDA was generated by adding n-butyllithium (2.4 mL of 2.5 M, 6.0 mmol) to a solution of diisopropylamine (0.84 mL, 6.0 mmol) in 30 mL of THF at 0(C. A solution of ethyl 6-oxo-3-azabicyclo [3.3.1]nonane-3-carboxylate (633 mg, 3.00 mmol) in 5 mL of THF was then added drop-wise, at −78(C, to the LDA. After stirring 45 min and warming to −30(C, the solution was re-cooled to −78(C and treated with 2-(N,N-bis(trifluoromethanesulfonyl) amino-5-chloropyridine (1.77 g, 4.50 mmol). The dark brown reaction mixture was stirred for 3 h, warming slowly to ambient temperature, and was quenched by the addition of a saturated aqueous sodium bicarbonate. The mixture was extracted with ether (2×50 mL), and the ether extracts were washed with a dilute sodium carbonate solution, water and brine (50 mL each). The ether solution was then dried over anhydrous magnesium sulfate, filtered and concentrated under reduced pressure. The resulting crude product was column chromatographed on silica gel, with a 0-5% gradient of methanol in dichloromethane, to give the desired enol triflate (0.32 g, 31%).

Ethyl 6-(3-pyridinyl)-3-azabicyclo[3.3.1]non-6-ene-3-carboxylate

A mixture of ethyl 6-trifluoromethanesulfonyloxy-3-azabicyclo[3.3.1] non-6-ene-3-carboxylate (270 mg, 0.790 mmol) in 6 mL of dimethoxyethane, 1.5 mL of saturated sodium carbonate solution, 3-pyridineboronic acid (146 mg, 1.20 mmol) and lithium chloride (99 mg, 2.37 mmol) was degassed and placed under an argon atmosphere (5 min purge). Tetrakis(triphenyphosphine)palladium(0) (60 mg) was added, and the reaction mixture was heated at reflux for 4 h. It was then cooled and filtered though a plug of silica gel, eluting with ethyl acetate. Concentration of the filtrate and column chomatography of the residue, with a gradient of 0-5% methanol in dichloromethane, gave a yellow oil (130 mg, 60%).

6-(3-Pyridinyl)-3-azabicyclo[3.3.1]non-6-ene

A mixture of ethyl 6-(3-pyridinyl)-3-azabicyclo[3.3.1] non-6-ene-3-carboxylate (100 mg, 0.370 mmol) and 1.5 mL of concentrated HCl was heated under reflux for 16 h. The mixture was cooled in an ice bath and made basic by adding 5 M aqueous sodium hydroxide. The suspension was extracted with chloroform (3×5 mL), and the extracts were dried over anhydrous sodium sulfate, filtered and concentrated under reduced pressure. The residue was filtered though a plug of silica gel, eluting with 90:10:1 dichloromethane/methanol/concentrated ammonium hydroxide, to give the product as an oil (11 mg, 15%).

Example 19

Example 19 is 7-(5-isopropoxy-3-pyridinyl)-3-azabicyclo [3.3.1]non-6-ene hemigalactarate, which was prepared in accordance with the following techniques:

7-(5-Isopropoxy-3-pyridinyl)-3-azabicyclo[3.3.1] non-6-ene hemigalactarate

To a solution of ethyl 7-(trifluoromethylsulfonyloxy)-3-azabicyclo[3.3.1] non-6-ene-3-carboxylate (0.12 g, 0.35 mmol) in dimethoxyethane (3 mL) was added saturated sodium carbonate solution (1 mL), lithium chloride (0.04 g, 0.9 mmol) and 5-isopropoxy-3-pyridinylboronic acid (0.12 g, 0.66 mmol). The flask was alternately evacuated and filled with argon three times. Tetrakis(triphenylphosphine)palladium(0) (0.01 g, 0.01 mmol) was added, and the evacuation and argon fill was performed once again. The flask was sealed under argon, and the stirred reaction mixture was heated at 95° C. for 2 h. The mixture was cooled to ambient temperature, diluted with water (10 mL), and extracted with chloroform (3×5 mL). The chloroform extracts were dried over anhydrous sodium sulfate and filtered. Concentration of the filtrate by rotary evaporation, followed by purification of the residue by silica gel column chromatography, using a gradient of 0-2% methanol in chloroform as eluent, gave 0.16 g of a light yellow oil. This was dissolved in ethanol (20 mL) and added to a stirred 50% aqueous KOH solution (10 mL). The mixture was then refluxed for 6 days. The ethanol was evaporated, and brine (20 mL) was added to the residue. Three chloroform extracts (15 mL each) were then taken, dried ($Na_2SO_4$) and concentrated. The residue was column chromatographed on silica gel, using a gradient of 0-1% concentrated ammonium hydroxide in 85:15 chloroform/methanol, to yield the free base (36.1 mg, 0.14 mmol). This was then dissolved in 5 mL of isopropanol, to which galactaric acid (20 mg, 0.095 mmol) was then added. The cloudy suspension was both heated and stirred while water was added drop-wise to the suspension. When the solution turned clear, it was filtered hot and then slowly cooled to ambient temperature and stored overnight. When no crystallization occurred, the solution was concentrated 2.5 mL and kept at 0(C for 3 hours. The white precipitate was collected by suction filtration and washed with cold isopropanol. After high vacuum drying (ambient temperature, 6 h) 4.8 mg (9.4%) of 7-(5-isopropoxy-3-pyridinyl)-3-azabicyclo[3.3.1]non-6-ene hemigalactarate (m.p. 172(C) remained.

Example 20

Example 20 is 7-(5-phenyl-3-pyridinyl)-3-azabicyclo[3.3.1]non-6-ene hemigalactarate, which was prepared in accordance with the following techniques:

Ethyl 7-(5-phenyl-3-pyridinyl)-3-azabicyclo[3.3.1]non-6-ene-3-carboxylate

To a solution of ethyl 7-(trifluoromethylsulfonyloxy)-3-azabicyclo[3.3.1] non-6-ene-3-carboxylate (0.12 g, 0.35 mmol) in dimethoxyethane (3 mL) was added saturated sodium carbonate solution (1 mL), lithium chloride (0.04 g, 0.9 mmol) and 5-phenyl-3-pyridinylboronic acid (0.12 g, 0.7 mmol). The flask was alternately evacuated and filled with argon three times. Then tetrakis(triphenylphosphine)palladium(0) (0.01 g, 0.01 mmol) was added, and the evacuation and argon fill was performed once again. The flask was then sealed under argon, and the stirred reaction mixture was heated at 95(C for 2 h. The mixture was cooled to ambient temperature, diluted with water (10 mL) and extracted with chloroform (3×5 mL). The combined extracts were dried over sodium sulfate and filtered. Concentration of the filtrate by rotary evaporation, followed by purification of the residue by silica gel column chromatography, using a gradient of chloroform/methanol (0-2% methanol) as eluent, gave ethyl 7-(5-phenyl-3-pyridinyl)-3-azabicyclo[3.3.1]non-6-ene-3-carboxylate as a light yellow oil (0.12 g, 90%).

7-(5-Phenyl-3-pyridinyl)-3-aza-bicyclo[3.3.1]non-6-ene hemigalactarate

A solution of ethyl 7-(5-phenyl-3-pyridinyl)-3-azabicyclo[3.3.1]non-6-ene-3-carboxylate (0.10 g, 0.29 mmol) in ethanol (20 mL) was added to a stirred 50% aqueous KOH solution (10 mL). The mixture was then refluxed for 3 days. The ethanol was evaporated, and brine (20 mL) was added to the residue. Three chloroform extracts (15 mL each) were then taken, dried ($Na_2SO_4$) and concentrated. The residue was column chromatographed on silica gel, using a gradient of 0-2% concentrated ammonium hydroxide in 85:15 chloroform/methanol, to yield the free base (30.1 mg, 0.109 mmol). This was dissolved in 5 mL of isopropanol, to which galactaric acid (13 mg, 0.062 mmol) was added. The cloudy suspension was both heated and stirred while water was added drop-wise to the suspension. When the solution turned clear, it was filtered hot and slowly cooled to ambient temperature, at which temperature it was kept overnight. The precipitate was filtered off and washed with cold isopropanol. After high vacuum drying (ambient temperature, 6 h), the white solid weighed 23.3 mg (56.1%, m.p. 186(C).

Example 21

Example 21 is 7-(5-phenoxy-3-pyridinyl)-3-azabicyclo[3.3.1]non-6-ene hemigalactarate, which was prepared in accordance with the following techniques:

Ethyl 7-(5-phenoxy-3-pyridinyl)-3-azabicyclo[3.3.1]non-6-ene-3-carboxylate

To a solution of ethyl 7-(trifluoromethylsulfonyloxy)-3-azabicyclo[3.3.1] non-6-ene-3-carboxylate (0.13 g, 0.38 mmol) in dimethoxyethane (3 mL) was added saturated sodium carbonate solution (1 mL), lithium chloride (0.04 g, 0.9 mmol) and 5-phenoxy-3-pyridinylboronic acid (0.17 g, 0.79 mmol). The flask was alternately evacuated and filled with argon three times. Then, tetrakis(triphenylphosphine)palladium(0) (0.01 g, 0.01 mmol) was added, and the evacuation and argon fill was performed once again. The flask was sealed under argon, and the stirred reaction mixture was heated at 95(C for 2 h. The mixture was cooled to ambient temperature, diluted with water (10 mL), extracted with chloroform (3×5 mL). The extracts were dried over sodium sulfate and filtered. Concentration of the filtrate by rotary evaporation, followed by purification of the residue by silica gel column chromatography, using a gradient of 0-2% methanol in chloroform/as eluent, gave ethyl 7-(5-phenoxy-3-pyridinyl)-3-azabicyclo[3.3.1]non-6-ene-3-carboxylate as a light yellow oil (0.12 g, 87%).

7-(5-Phenoxy-3-pyridinyl)-3-aza-bicyclo[3.3.1]non-6-ene hemigalactarate

A solution of ethyl 7-(5-phenoxy-3-pyridinyl)-3-azabicyclo[3.3.1]non-6-ene-3-carboxylate (0.12 g, 0.33 mmol) in ethanol (20 mL) was added to a stirred 50% aqueous KOH solution (10 mL). The mixture was then refluxed for 3 days. The ethanol was evaporated, and brine (20 mL) was added to the residue. Three chloroform extracts (15 mL each) were then taken, dried ($Na_2SO_4$) and concentrated. The residue was column chromatographed on silica gel, using a gradient of 0-2% concentrated ammonium hydroxide in 85:15 chloroform/methanol, to yield the free base (54.1 mg, 0.185 mmol). This was dissolved in 5 mL of isopropanol, to which galactaric acid (20 mg, 0.095 mmol) was added. The cloudy suspension was both heated and stirred while water was added drop-wise to the suspension. When the solution turned clear, it was filtered hot and slowly cooled to ambient temperature, where it was kept overnight. The precipitate was filtered off and washed with cold isopropanol. After high vacuum drying (ambient temperature, 6 h), the white solid weighed 40.7 mg (55.5%, m.p. 176(C).

Example 22

Example 22 is 7-(5-methoxy-3-pyridinyl)-3-azabicyclo[3.3.1]non-6-ene hemigalactarate, which was prepared in accordance with the following techniques:

7-(5-Methoxy-3-pyridinyl)-3-azabicyclo[3.3.1]non-6-ene hemigalactarate

To a solution of ethyl 7-(trifluoromethylsulfonyloxy)-3-azabicyclo[3.3.1] non-6-ene-3-carboxylate (0.32 g, 0.93 mmol) in dimethoxyethane (8 mL) was added saturated sodium carbonate solution (2.5 mL), lithium chloride (0.12 g, 2.8 mmol) and 5-methoxy-3-pyridinylboronic acid (0.29 g, 1.9 mmol). The flask was alternately evacuated and filled with argon three times. Tetrakis(triphenylphosphine)palladium(0) (0.02 g, 0.02 mmol) was added, and the evacuation and argon fill was performed once again. The flask was sealed under argon, and the stirred reaction mixture was heated at 95(C for 2 h. The mixture was cooled to ambient temperature, diluted with water (10 mL) and extracted with chloroform (3×5 mL). The chloroform extracts were dried over sodium sulfate and filtered. Concentration of the filtrate by rotary evaporation, followed by purification of the residue by silica gel column chromatography, using a gradient of 0-2% methanol in chloroform, gave 0.41 g of a light yellow oil. This was dissolved in ethanol (40 mL) and added to a stirred 50% aqueous KOH solution (20 mL). The mixture was then refluxed for 16 h. The ethanol was evaporated, and brine (20 mL) was added to the residue. Three chloroform extracts (20 mL each) were then taken, dried ($Na_2SO_4$) and concentrated. The residue was dissolved in toluene (20 mL), concentrated again and column chromatographed on silica gel, using a gradient of 95:5:1 to 90:10:2 chloroform/methanol/concentrated ammonium hydroxide as eluent, to yield the free base (100 mg, 33%). A portion of this free base (40 mg, 0.17 mmol) was dissolved in isopropanol (3 mL) and treated with galactaric acid (20 mg, 0.095 mmol). The mixture was then swirled and heated as water was slowly added. When the mixture clarified, it was filtered hot and the filtrate cooled. After sitting at ambient temperature overnight, the mixture was filtered, to yield a white solid, which was washed with cold isopropanol and high vacuum dried (ambient temperature, 6 h) to yield 11.5 mg (7.9%, m.p. 162-164(C).

Example 23

Example 23 is 6-(5-phenoxy-3-pyridinyl)-3-azabicyclo[3.2.1]oct-6-ene trifluoroacetate, which was prepared in accordance with the following techniques:

Ethyl 6-hydroxy-6-(5-phenoxy-3-pyridinyl)-3-azabicyclo[3.2.1]octane-3-carboxylate To a solution of 3-bromo-5-phenoxypyridine (0.51 g, 2.0 mmol) in dry diethyl ether (15 mL) at −78° C. was added 2.5 M n-butyllithium (0.80 mL, 2.0 mmol). The reaction was stirred for 30 min under nitrogen at −78° C. and then slowly transferred by cannula into a solution of ethyl 6-oxo-3-azabicyclo[3.2.1]octane-3-carboxylate (0.20 g, 1.0 mmol) in THF (15 mL) at −78° C. The reaction was stirred 4 h at −78° C. and then warmed to ambient temperature overnight, at which time it was quenched with saturated aqueous ammonium chloride (20 mL). The mixture was then extracted with chloroform (2×10 mL), and the combined extracts were dried over sodium sulfate, filtered, and concentrated by rotary evaporation. Excess pyridine was removed by repeated azeotropic rotary evaporation with toluene, and the residue was chromatographed on a silica gel column (with 5% methanol in chloroform) to yield the desired product (0.31 g, 84%).

6-(5-Phenoxy-3-pyridinyl)-3-azabicyclo[3.2.1]oct-6-ene trifluoroacetate

To ethyl 6-hydroxy-6-(5-phenoxy-3-pyridinyl)-3-azabicyclo[3.2.1] octane-3-carboxylate (0.31 g, 0.84 mmol) at 0° C. was added triethylamine (0.47 mL, 3.4 mmol) and thionyl chloride (0.18 mL, 2.5 mmol). The mixture was heated at reflux for 18 h under nitrogen. The volatiles were removed by azeotropic rotary evaporation with toluene (2×10 mL) to give a dark brown oil, which was suspended in a 50% solution of potassium hydroxide (5 g) in ethanol (10 mL) and refluxed for 18 h. The reaction mixture was cooled to ambient temperature and concentrated by rotary evaporation. Then brine (10 mL) was added, and the mixture was filtered. The collected solids were washed with chloroform (25 mL), and the filtrate was extracted with chloroform (3×25 mL). The combined chloroform extracts were dried over sodium sulfate, filtered and concentrated by rotary evaporation. Preparative HPLC purification of the residue, using 0.1% trifluoroacetic acid in an acetonitrile/water gradient, gave the desired product as a trifluoroacetate salt (77 mg, 29%).

Example 24

Example 24 is 6-(5-phenyl-3-pyridinyl)-3-azabicyclo[3.2.1]oct-6-ene trifluoroacetate, which was prepared in accordance with the following techniques:

Ethyl 6-hydroxy-6-(5-phenyl-3-pyridinyl)-3-azabicyclo[3.2.1]octane-3-carboxylate To a solution of 3-bromo-5-phenylpyridine (0.23 g, 1.0 mmol) in THF (5 mL) at ambient temperature was added 2.0 M isopropylmagnesium chloride in THF (0.5 mL). The reaction was stirred for an hour under nitrogen. Then a solution of ethyl 6-oxo-3-azabicyclo[3.2.1]octane-3-carboxylate (0.21 g, 1.0 mmol) in THF (2 mL) was added. The mixture was stirred at ambient temperature overnight, concentrated and quenched with water (1 mL). The mixture was extracted with chloroform (2×10 mL), and the combined extracts were dried over magnesium sulfate, filtered, and concentrated by rotary evaporation. The compound was purified by silica gel column chromatography (1:1 ethyl acetate/hexane) to yield 50 mg of product (13%).

6-(5-Phenyl-3-pyridinyl)-3-azabicyclo[3.2.1]oct-6-ene trifluoroacetate

To ethyl 6-hydroxy-6-(5-phenyl-3-pyridinyl)-3-azabicyclo[3.2.1]octane-3-carboxylate (0.13 g, 0.37 mmol) at 0° C. was added triethylamine (0.30 mL, 1.2 mmol) and thionyl chloride (0.06 mL, 0.8 mmol). The mixture was heated at reflux for 18 h under nitrogen. The volatiles were removed by azeotropic rotary evaporation with toluene (2×20 mL) to give a dark brown oil, which was suspended in a 50% solution of potassium hydroxide in ethanol (10 mL) and refluxed for 18 h. The reaction mixture was cooled to ambient temperature and concentrated by rotary evaporation. Then brine (10 mL) was added, and the mixture was filtered. The collected solids were washed with chloroform (25 mL), and the filtrate was extracted with chloroform (3×25 mL). The combined chloroform extracts were dried over sodium sulfate, filtered, concentrated by rotary evaporation. Preparative HPLC purification of the residue, using 0.1% trifluoroacetic acid in an acetonitrile/water gradient, gave the desired product as a trifluoroacetate salt (59 mg, 43%).

Example 25

Example 25 is 6-(5-isopropoxy-3-pyridinyl)-3-azabicyclo[3.2.1]oct-6-ene trifluoroacetate, which was prepared in accordance with the following techniques:

Ethyl 6-hydroxy-6-(5-isopropoxy-3-pyridinyl)-3-azabicyclo[3.2.1] octane-3-carboxylate To a solution of 3-bromo-5-isopropoxypyridine (0.66 g, 3.1 mmol) in dry diethyl ether (15 mL) at −78° C. was added 2.5 M n-butyllithium (1.2 mL, 3.0 mmol). The reaction was stirred for 30 min under nitrogen at −78° C. and then slowly transferred by cannula into a solution of ethyl 6-oxo-3-azabicyclo[3.2.1]octane-3-carboxylate (0.30 g, 1.5 mmol) in THF (15 mL) at −78° C. The reaction was stirred 4 h at −78° C. and then warmed to ambient temperature overnight, at which time it was quenched with saturated aqueous ammonium chloride (20 mL). The reaction was then extracted with chloroform (2×10 mL), and the combined extracts were dried over sodium sulfate, filtered, and concentrated by rotary evaporation. Excess pyridine was removed by repeated azeotropic rotary evaporation with toluene, and the residue was chromatographed on a silica gel column (with 5% methanol in chloroform) to yield the desired product (0.34 g, 61%).

6-(5-Isopropoxy-3-pyridinyl)-3-azabicyclo[3.2.1] oct-6-ene trifluoroacetate

To ethyl 6-hydroxy-6-(5-isopropoxy-3-pyridinyl)-3-azabicyclo[3.2.1] octane-3-carboxylate (0.34 g, 1.0 mmol) at 0° C. was added triethylamine (0.57 mL, 4.1 mmol) and thionyl chloride (0.23 mL, 3.1 mmol). The mixture was heated to reflux for 18 h under nitrogen. The volatiles were removed by azeotropic rotary evaporation with toluene (2×10 mL) to give a dark brown oil, which was suspended in a 50% solution of potassium hydroxide in ethanol (10 mL) and refluxed for 18 h. The reaction mixture was cooled to ambient temperature and concentrated by rotary evaporation. Then brine (10 mL) was added, and the mixture was filtered. The collected solids were washed with chloroform (25 mL), and the filtrate was extracted with chloroform (3×25 mL). The combined chloroform extracts were dried over sodium sulfate, filtered, concentrated by rotary evaporation. Preparative HPLC purification of the residue, using 0.1% trifluoroacetic acid in an acetonitrile/water gradient, gave the desired product as a trifluoroacetate salt (60 mg, 47%) (mp 133-134° C.).

Example 26

Example 26 is the syntheses of the 5-substituted-3-pyridinylboronic acids that were not commercially available (i.e., 5-methoxy, 5-isopropoxy, 5-phenoxy and 5-phenyl). These were produced from the corresponding bromopyridines (the syntheses of which have been reported in U.S. Pat. No. 5,861,423 and PCT WO 99/65876) by the procedure of Li et al., reported in *J. Org. Chem.* 67(15):5394-5397 (2002). An example, the synthesis of the 5-methoxy-3-pyridinylboronic acid, is included here.

5-Methoxy-3-pyridinylboronic acid

Triisopropyl borate (29.3 mL, 128 mmol) was added over 2 min to a solution of 5-methoxy-3-bromopyridine (20.00 g, 106.4 mmol) in toluene (140 mL) and tetrahydrofuran (35 mL) at −40° C. To this solution was added 2.5 M n-BuLi (51.1 mL, 128 mmol) drop-wise over 35 min while maintaining the temperature at −40° C. After the addition was complete, the reaction was stirred an additional 30 min at −40° C. and then was warmed to −15° C. over one hour. Into the reaction was poured 1 N HCl (175 mL), and the mixture was stirred vigorously for 30 minutes. The layers were separated, and the organic washed once with water (15 mL). The aqueous phases were combined and neutralized (to pH 7) with 5 N NaOH, at which point the boronic acid precipitated out. The biphasic mixture was extracted with THF (3×150 mL). The organic phases were combined, dried over sodium sulfate, filtered, and concentrated to yield 15.36 g of 5-methoxy-3-pyridinylboronic acid as a light brown solid (94%).

Example 27

Example 27 is the pair of regioisomers, 3-(5-pyrimidinyl)-6-azabicyclo[3.2.1]oct-2-ene trifluoroacetate and 3-(5-pyrimidinyl)-6-azabicyclo[3.2.1]oct-3-ene trifluoroacetate, which was prepared in accordance with the following techniques:

3-(5-Pyrimidinyl)-6-azabicyclo[3.2.1]oct-2-ene trifluoroacetate and 3-(5-pyrimidinyl)-6-azabicyclo [3.2.1]oct-3-ene trifluoroacetate To a solution of a mixture of t-butyl 3-trifluoromethanesulfonyloxy-6-azabicyclo[3.2.1]oct-2-ene-6-carboxylate and t-butyl 3-trifluoromethanesulfonyloxy-6-azabicyclo [3.2.1]oct-3-ene-6-carboxylate (0.10 g, 0.30 mmol) in dimethoxyethane (2 mL) was added a saturated solution of sodium carbonate (0.80 mL), lithium chloride (26 mg, 0.62 mmol) and pyrimidine-5-boronic acid (74 mg, 0.59 mmol). The flask was alternately evacuated and filled with argon three times. Tetrakis(triphenylphosphine)palladium(0) (13 mg, 0.013 mmol) was added, and the evacuation and argon fill was performed once again. The reaction mixture was stirred vigorously and heated at reflux for 4 h. The dark mixture was partitioned between 5 M NaOH (1 mL) and chloroform (2 mL). The organic layer was collected and combined with a second chloroform (3 mL) extract of the aqueous layer. This combined chloroform extracts were dried over sodium sulfate, filtered and concentrated. The residue was combined with 10 mL of methanolic aqueous KOH (made by dissolving 35 g of KOH in a mixture of 25 mL of water and 100 mL of methanol) and refluxed overnight. The reaction mixture was cooled, and the volatiles were evaporated. Preparative HPLC purification of the residue, using 0.1% trifluoroacetic acid in an acetonitrile/water gradient, gave the desired product as a trifluoroacetate salt (41 mg, 45%).

Example 28

Assessment of Analgesic Effects of Compounds of Example 1

The compounds of Example 1 (administered as the dihydrochloride salt of a 3:1 mixture of 3-(3-pyridinyl)-6-azabicyclo[3.2.1]oct-2-ene and 3-(3-pyridinyl)-6-azabicyclo [3.2.1]oct-3-ene) were evaluated in this Example using a "hot plate" test in mice. Briefly, the compounds of Example 1 (0.03, 0.1 and 0.3 mg free base/kg) were subcutaneously administered five minutes before the hot plate test. Morphine (10 mg/kg) was subcutaneously administered at 15 minutes before the test. Each mouse was placed on a metallic hot plate maintained at 52±0.2° C. The nociceptive reaction latency, characterized by licking reflex of the forepaws or by jumping off the hot plate, was recorded. The cutoff was set to 30 seconds. At 0.03, 0.1 and 0.3 mg/kg, the compounds of Example 1 increased the nociceptive threshold by +72, +68 and +152%, respectively. The rise in the nociceptive reaction latency was significant for all doses. The results are tabulated below in Table 1.

TABLE 1

| Treatment | Dose (mg/kg) | n | Reaction Latency (sec) | % variation |
| --- | --- | --- | --- | --- |
| Saline | — | 10 | 11.2 ± 0.7 | — |
| Morphine | 10 | 10 | 29.4 ± 0.5* | 163 |
| Compounds of Example 1 | 0.03 | 10 | 19.3 ± 2.8* | 72 |
|  | 0.1 | 10 | 18.8 ± 2.2* | 68 |
|  | 0.3 | 10 | 28.2 ± 1.8* | 152 |

Results expressed as mean ± SEM
Vehicle (saline)
Dunnett's test: *indicates a significant difference in comparison with vehicle-treated "injured paw" group for $P < 0.05$ The time course of the analgesic effect of the compounds of Example 1 (0.1, 0.3 and 1.0 mg free base/kg) was also assessed using the hot plate test following oral administration. Each dose of the compounds was administered to separate groups of animals at either 5, 15, 30 or 60 minutes prior to hot plate assessment. Morphine (60 mg/kg) and vehicle were also orally administered to separate groups of animals either 5, 15, 30, or 60 minutes before the test. Each mouse was placed on a metallic hot plate maintained at 52±0.2° C. The nociceptive reaction latency, characterized by licking reflex of the forepaws or by jumping off the hot plate, was recorded. The cutoff was set to 30 seconds.

Morphine (60 mg/kg), at 15, 30 and 60 minutes after dosing, significantly increased nociceptive reaction latency in comparison with vehicle-control by +69%, +47% and +37%, respectively. The compounds of Example 1 (1.0 mg/kg), at 5 and 15 minutes after dosing, significantly increased the nociceptive reaction latency by +82% and +97%, respectively compared to vehicle controls. Lower doses failed to modify the nociceptive threshold when compared to the vehicle-treated group (data not shown).

A rat model of peripheral mononeuropathy (Bennett Model) was also used to evaluate the antihyperalgesic properties of the compounds.

Briefly, peripheral mononeuropathy was induced by loose ligation of the sciatic nerve in anaesthetized rats (pentobarbital; 45 mg/kg by intraperitoneal route). Fourteen days later, the nociceptive threshold was evaluated using a mechanical nociceptive stimulation (paw pressure test). An increasing pressure was applied onto the hindpaw of the animal until the nociceptive reaction (vocalization or paw withdrawal) was reached. The pain threshold (grams of contact pressure) was measured in hindpaws, both ipsilateral (injured side) and contralateral (non-injured side) to the site of sciatic ligation injury, at 10 minutes after the oral treatment for the compounds (1 mg/kg) and 60 minutes after dosing for morphine (60 mg/kg) and vehicle.

The results were expressed as a) the nociceptive threshold (mean±SEM) in grams of contact pressure for the injured paw and for the non-injured paw in the vehicle-treated group, and b) the percentage of variation of the nociceptive threshold calculated from the mean value of the vehicle-treated group.

In the vehicle-treated group, a statistically significant decrease in the nociceptive threshold was evidenced in injured paw as compared to the control paw, demonstrating a clear hyperalgesia in the rats. In the group treated with morphine (60 mg/kg), the nociceptive threshold was significantly increased in comparison to the vehicle-treated group (by +144%, 60 minutes after dosing). Ten minutes after being orally administered, 1 mg/kg of the compounds of Example 1 increased the nociceptive threshold in the injured paw to a lesser, but significant, extent (+20%, in comparison to the vehicle-treated group). No behavioral side-effects were observed following the dosing with the compounds. The results are tabulated below in Table 2.

TABLE 2

|  | Control Paw | Injured Paw | Injured Paw | Injured Paw |
|---|---|---|---|---|
| Test Article | Vehicle | Vehicle | Compounds of Example 1 | Morphine |
| Dose (mg/kg) | — | — | 1 | 60 |

TABLE 2-continued

|  | Control Paw | Injured Paw | Injured Paw | Injured Paw |
|---|---|---|---|---|
| Nociceptive threshold (g) | 310.0 ± 12.0 | 110.0 ± 9.5 | 132.0 ± 9.0* | 268.0 ± 18.9* |
| % Variation | — | — | 20 | 144 |

Results expressed as mean ± SEM

Vehicle (distilled water)

Dunnett's test: *indicates a significant difference in comparison with vehicle-treated "injured paw"group for P < 0.05

For additional details and further guidance regarding the test protocols, please see Bennett and Xie, *Pain,* 33:87-107 (1988); D'amour and Smith, *J. Pharmacol. Exp. Ther.,* 72:74-79 (1941); and Grossman et al., *J. Comp. Neurol.,* 206:9-16 (1982), all incorporated herein by reference.

Example 29

Summary of Biological Activity

The following compounds were evaluated using the techniques described above.

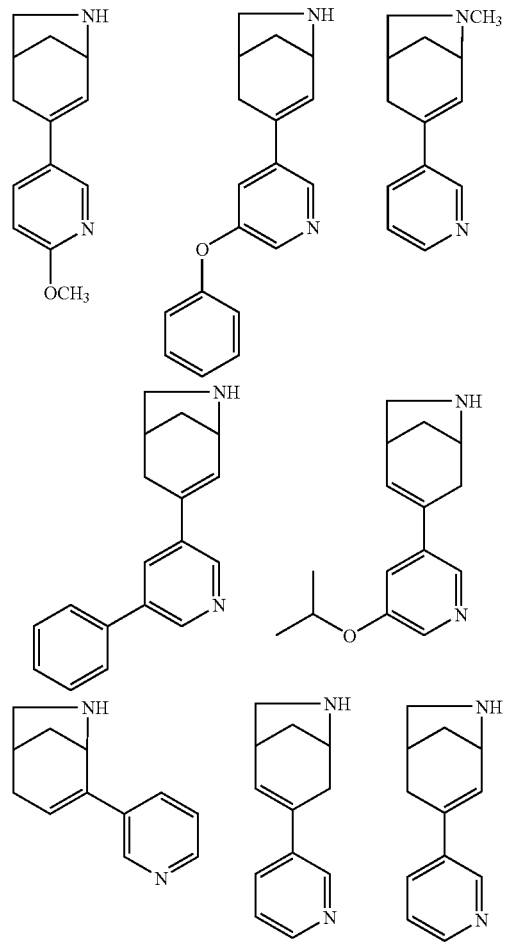

-continued

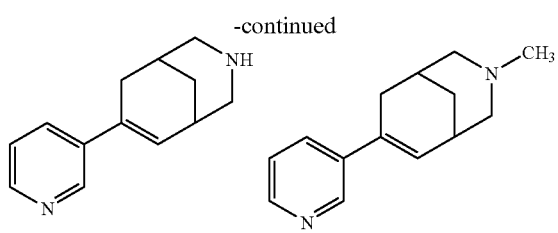

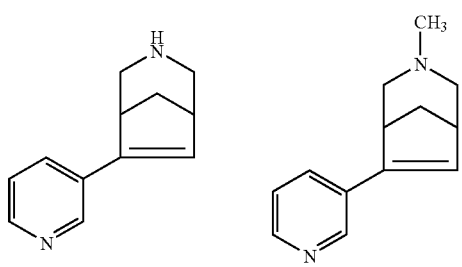

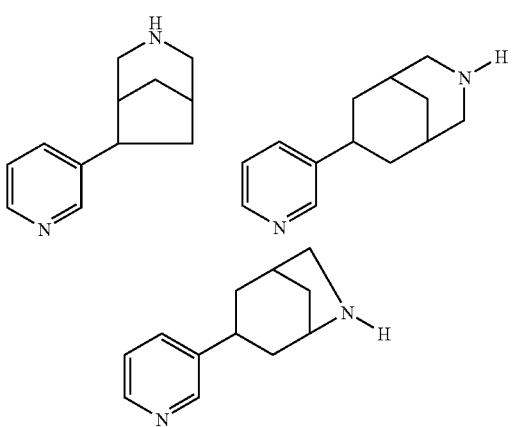

The biological data indicate that the compounds of the present invention have the ability to selectively bind with high affinity to the α7 (Ki values from 300 pM to 10 μM) and α4β2 (Ki values from 100 pM to 24 nM) receptors, as indicated by relatively low binding constants, and in some cases bind at concentrations well below those concentrations required for activation of muscle or ganglionic receptors. Thus, the data indicated that the compounds have the capability of being useful in treating CNS disorders involving nicotinic cholinergic systems.

Furthermore, the data indicate that certain of these compounds do not cause any appreciable side effects at muscle sites or ganglionic sites at concentrations effective for producing CNS effects or neurotransmitter release (as low as 30 nM for dopamine release), thus indicating a lack of undesirable side effects in subjects receiving administration of those compounds at dose ranges at which CNS effects and neurotransmitter release are elicited.

The foregoing is illustrative of the present invention and is not to be construed as limiting thereof. The invention is defined by the following claims, with equivalents of the claims to be included therein.

What is claimed is:

1. A compound of Formula 1 or 2:

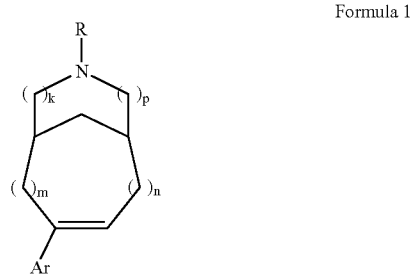

Formula 1

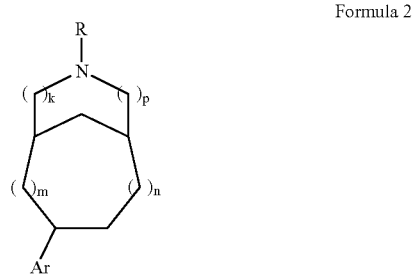

Formula 2 wherein k, and p are each 1, m and n are individually 0 or 1; provided that if m is 1, then n is 0, and if n is 1, then m is 0;
Ar is pyridine, optionally substituted at any position with a substituent Z;
Z is selected from the group consisting of lower alkyl, lower alkenyl, cycloalkyl, phenyl, benzyl, halo, —OR', —NR'R", —CF$_3$, —CN, —NO$_2$, —C≡CR', —SR', and —SO$_2$R';
where R' and R" are individually hydrogen, lower alkyl, cycloalkyl phenyl, or benzyl; and
R is hydrogen, unsubstituted lower alkyl, unsubstituted arylalkyl, unsubstituted alkoxycarbonyl, or unsubstituted aryloxycarbonyl;
or a pharmaceutically acceptable salt thereof.

2. The compound of claim 1, wherein Ar is 3-pyridinyl.

3. The compound of claim 1, having a structure as in Formula 2, wherein the carbon at which the azabicyclic ring is attached to the Ar moiety has R stereochemistry.

4. The compound of claim 1, having a structure as in Formula 2, wherein the carbon at which the azabicyclic ring is attached to the Ar moiety has S stereochemistry.

5. A compound selected from the group consisting of:

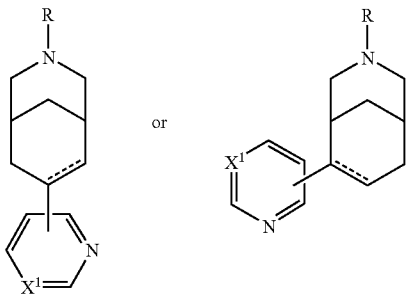

wherein:
X¹ is —CH— or —CZ—;
Z is selected from the group consisting of lower alkyl, lower alkenyl, cycloalkyl, phenyl, benzyl, halo, —OR', —NR'R", —CF₃, —CN, —NO₂, —C≡CR', —SR', and —SO₂R';
where R' and R" are individually hydrogen, lower alkyl, cycloalkyl phenyl, or benzyl;
R is hydrogen, unsubstituted lower alkyl, unsubstituted arylalkyl, unsubstituted alkoxycarbonyl, or unsubstituted aryloxycarbonyl; and
the hashed bond indicates the presence or absence of a double bond;
or a pharmaceutically acceptable salt thereof.

6. The compound of claim 1 wherein Ar is unsubstituted pyridine.

7. The compound of claim 1, wherein Ar is pyridine substituted with one or more Z, individually selected from the group consisting of lower alkyl, amino, phenyl, halo, and —OR', where R' is selected from lower alkyl or phenyl.

8. The compound of claim 7 wherein said lower alkyl is methyl or isopropyl.

9. The compound of claim 1 wherein the compound is of Formula 1.

10. The compound of claim 1 wherein the compound is of Formula 2.

11. A compound selected from the group consisting of:
6-(3-pyridinyl)-3-azabicyclo[3.3.1]non-6-ene,
7-(3-pyridinyl)-3-azabicyclo[3.3.1]non-6-ene,
6-(3-pyridinyl)-3-azabicyclo[3.3.1]nonane,
7-(3-pyridinyl)-3-azabicyclo[3.3.1]nonane,
6-(5-methoxy-3-pyridinyl)-3-azabicyclo[3.3.1]non-6-ene,
7-(5-methoxy-3-pyridinyl)-3-azabicyclo[3.3.1]non-6-ene,
6-(5-methoxy-3-pyridinyl)-3-azabicyclo[3.3.1]nonane,
7-(5-methoxy-3-pyridinyl)-3-azabicyclo[3.3.1]nonane,
6-(6-methoxy-3-pyridinyl)-3-azabicyclo[3.3.1]non-6-ene,
7-(6-methoxy-3-pyridinyl)-3-azabicyclo[3.3.1]non-6-ene,
6-(6-methoxy-3-pyridinyl)-3-azabicyclo[3.3.1]nonane,
7-(6-methoxy-3-pyridinyl)-3-azabicyclo[3.3.1]nonane,
6-(5-isopropoxy-3-pyridinyl)-3-azabicyclo[3.3.1]non-6-ene,
7-(5-isopropoxy-3-pyridinyl)-3-azabicyclo[3.3.1]non-6-ene,
6-(5-isopropoxy-3-pyridinyl)-3-azabicyclo[3.3.1]nonane,
7-(5-isopropoxy-3-pyridinyl)-3-azabicyclo[3.3.1]nonane,
6-(5-phenoxy-3-pyridinyl)-3-azabicyclo[3.3.1]non-6-ene,
7-(5-phenoxy-3-pyridinyl)-3-azabicyclo[3.3.1]non-6-ene,
6-(5-phenoxy-3-pyridinyl)-3-azabicyclo[3.3.1]nonane,
7-(5-phenoxy-3-pyridinyl)-3-azabicyclo[3.3.1]nonane,
6-(5-phenyl-3-pyridinyl)-3-azabicyclo[3.3.1]non-6-ene,
7-(5-phenyl-3-pyridinyl)-3-azabicyclo[3.3.1]non-6-ene,
6-(5-phenyl-3-pyridinyl)-3-azabicyclo[3.3.1]nonane,
7-(5-phenyl-3-pyridinyl)-3-azabicyclo[3.3.1]nonane,
6-(6-chloro-3-pyridinyl)-3-azabicyclo[3.3.1]non-6-ene,
7-(6-chloro-3-pyridinyl)-3-azabicyclo[3.3.1]non-6-ene,
6-(6-chloro-3-pyridinyl)-3-azabicyclo[3.3.1]nonane, and
7-(6-chloro-3-pyridinyl)-3-azabicyclo[3.3.1]nonane
or a pharmaceutically acceptable salt thereof.

12. 7-(3-pyridinyl)-3-azabicyclo[3.3.1]non-6-ene or pharmaceutically acceptable salt thereof.

13. The dihydrochioride salt of the compound of claim 12.

14. A pharmaceutical composition comprising a compound of claim 1 and a pharmaceutically acceptable carrier.

15. A pharmaceutical composition comprising a compound of claim 11 and a pharmaceutically acceptable carrier.

16. A pharmaceutical composition comprising a compound of claim 13 and a pharmaceutically acceptable carrier.

17. A pharmaceutical composition comprising a compound of claim 13 and a pharmaceutically acceptable carrier.

* * * * *